United States Patent
Kawai et al.

[11] Patent Number: 6,048,880
[45] Date of Patent: Apr. 11, 2000

[54] PYRIDYLFURAN AND PYRIDYLTHIOPHENE COMPOUNDS

[75] Inventors: Akiyoshi Kawai, Handa; Makoto Kawai, Aichi-ken, both of Japan

[73] Assignee: Pfizer Pharamaceuticals Inc., Japan

[21] Appl. No.: 09/003,108

[22] Filed: Jan. 6, 1998

[30] Foreign Application Priority Data

Jan. 6, 1997 [WO] WIPO ................ PCT/IB97/00002

[51] Int. Cl.[7] .............. C07D 405/04; C07D 405/14; A61K 31/4433; A61K 31/4436
[52] U.S. Cl. .............. 514/336; 514/340; 546/256; 546/280.4
[58] Field of Search .............. 546/256, 280.4; 514/336, 340

[56] References Cited

FOREIGN PATENT DOCUMENTS

WO98/02430 1/1998 WIPO.

OTHER PUBLICATIONS

Gilat, Sylvain L. et al., Light–triggered electrical and optical switching devices; *J. Chem. Soc., Chem. Commun.* vol. 18, pp. 1439–1442, (1993).

Ribereau, Pierre et al., "Synthesis of furylpyridines", *Chemical Abstracts*, vol. 82, No. 23, Jun. 9, 1975 (Abstract No. 156020k), see also C. R. Hebd. Seances Acad. Sci., (France) Ser., C, Vol. 280(5), pp. 293–296, (1975).

Oda, Kazuaki et al.: "Benzannulation of heteroaromatics by photoreaction of arenecarbothiamides with 2 methoxyfuran", *J. Chem. Soc., Chem. Commun.*, vol. 12, pp. 1477–1278, (1994).

Zhang, Yihua et al., "Pyridine–substituted hydroxythiophenes. II. Alkylation of 0–(2–, 3– and 4–pyridyl)–3–hydroxythiophenes", *J. Heterocyclic Chem.*, vol. 30(5), pp. 1293–1299, (1993).

Bacon, Edward R. et al., "Synthesis of 7–ethyl–4, 7–dihydro–4–oxo–2–(4–pyridinyl)thieno[2,3–b] pyridine–5–caboxylic acid", *J. Heterocyclic Chem.*, vol. 28(8), pp. 1953–1955, 1991).

Katritzky, Alan R. et al., "Aqueous high–temperature chemistry of carbo–and heterocycles. 14. Mercaptan and sulfonic acids", *Chemical Abstracts*, vol. 113(16), Oct. 15, 199, Abstract No. 135394d.

*Primary Examiner*—Alan L. Rotman
*Attorney, Agent, or Firm*—Peter C. Richardson; Paul H. Ginsburg; E. Victor Donahue

[57] ABSTRACT

A compound of the formula:

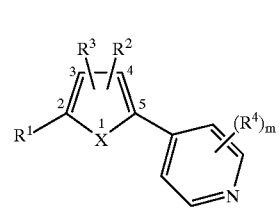

(I)

and its pharmaceutically effective salts, wherein $R^1$ and $R^2$ are independently selected from the following:

(a) hydrogen, halo, $R^5$—, $C_{2-6}$ alkenyl, $C_{2-6}$ alkynyl, hydroxy-$R^5$—, $R^5$—O—$R^5$—, or the like; (b) Ar—, Ar—$R^5$—, Ar—$C_{2-6}$ alkenyl, Ar—$C_{2-6}$ alkynyl, Ar—O—, Ar—O—$R^5$— or the like; (c) $R^5$—C(O)—, —$NO_2$, cyano, $NH_2$—C(O)—, $R^5$—NH—C(O)—, $(R^5)_2$—N—C(O)—, Ar—C(O)— or the like; and (d) $R^5$—C(O)—NH—, Ar—C(O)—NH— or the like; wherein Ar is optionally substituted aryl or heteroaryl such as phenyl and pyridyl; and wherein $R^5$ is optionally halo-substituted $C_{1-6}$ alkyl; $R^3$ is selected from the following: (e) cyano, formyl, tetrazolyl, triazolyl, imidazolyl, oxazolyl, thiazolyl, $R^5$—C(O)—, $C_{2-6}$ alkenyl-C(O)—, $C_{2-6}$ alkynyl-C(O)—, $R^5$—C(O)—$R^5$—, or the like; (f) $R^5$—C(O)—NH—, Ar—C(O)—NH—, or the like; (g) $R^5$—S—, $R^5$—S(O)—, $R^5$—NH—$S(O)_2$—, or the like; and (h) Ar—C(O)—, Ar—$R^5$—C(O)—, Ar—$C_{2-6}$ alkenylene-C(O)— or the like; or two of $R^1$, $R^2$ and $R^3$ together form a group of the formula —$A^1$—$B^1$—$A^2$— or —$A^1$—$B^1$—$A^3$—$B^2$—$A^2$— such as cyclic alkyl optionally substituted with oxo; $R^4$ is hydrogen, halo, $R^5$—C(O)— and the like; X is O, S, S(O) or $S(O)_2$; m is 0, 1, 2, 3 or 4. The present invention also provides processes for the preparation thereof, the use thereof in treating cytokine mediated diseases and/or cell adhesion molecule (CAM) mediated diseases and pharmaceutical compositions for use in such therapy.

8 Claims, No Drawings

PYRIDYLFURAN AND PYRIDYLTHIOPHENE COMPOUNDS

TECHNICAL FIELD

This invention relates to novel pyridylfuran and pyridylthiophene compounds, their pharmaceutically effective salts, processes for the preparation thereof, the use thereof in treating cytokine mediated diseases and/or cell adhesion molecule mediated diseases, and pharmaceutical compositions for use in such therapy.

BACKGROUND ART

Cytokines possess a multitude of regulatory and inflammatory effects. Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation.

There are many disease states in which excessive or unregulated IL-1 production is implicated in exacerbating and/or causing the disease. These include rheumatoid arthritis (RA), osteoarthritis (OA), endotoxemia and/or toxic shock syndrome, other acute and chronic inflammatory disease states such as the inflammatory reaction induced by endotoxin or inflammatory bowel disease (IBD), tuberculosis, atherosclerosis, muscle degeneration, cachexia, psoriatic arthritis, Reiter's syndrome, gout, traumatic arthritis, rubella arthritis and acute synovitis. Recent evidence also links IL-1 activity to diabetes.

Excessive or unregulated TNF production has been implicated in mediating or exacerbating a number of diseases including RA, rheumatoid spondylitis, OA, gouty arthritis and other arthritic conditions, sepsis, septic shock, endotoxic shock, gram negative sepsis, toxic shock syndrome, adult respiratory distress syndrome (ARDS), cerebral malaria, chronic pulmonary inflammatory disease, silicosis, pulmonary sarcoidosis, bone resorption diseases, reperfusion injury, graft vs. host reaction, allograft rejections, fever and myalgias due to infection such as influenza, cachexia secondary to infection or malignancy, cachexia, cancer, secondary to acquired immune deficiency syndrome (AIDS), ARC (AIDS related complex), keloid formation, diabetes, obesity, scar tissue formation, Crohn's disease, ulcerative colitis or pyresis. The concept of anti-TNF therapy has been validated by the demonstration that soluble TNF receptor and neutralizing monoclonal antibodies (MAbs) against TNF showed therapeutic efficacy in a variety of preclinical and clinical studies (e.g., Elliott, M. J. et al., *The Lancet,* 1994, 344, 1125. Dullemen, H. M. V. et al. Gastroenterology, 1995, 109, 129.)

Interleukin-8 (IL-8) is a chemotactic factor first identified and characterized in 1987. IL-8 is produced by several cell types including neutrophils, mononuclear cells, fibroblasts, endothelial cells, epithelial cells and keratinocytes. Elevated IL-8 levels have been reported in joint fluids in RA, gouty arthritis, psoriatic scale and ARDS. Its production from endothelial cells is induced by IL-1, TNF or lipopolysaccharide (LPS). IL-8 has been shown to have chemoattractant properties for neutrophils, T-lymphocytes and basophils. In addition, it promotes angiogenesis as well as neutrophil activation, including lysozomal enzyme release and respiratory burst. IL-8 has also been shown to increase the surface expression of Mac-1 (CD11b/CD18) on neutrophils, which may contribute to increased adhesion of the neutrophils to vascular endothelial cells. Many diseases are characterized by massive neutrophil infiltration. Conditions associated with an increased IL-8 production would benefit by compounds which suppress of IL-8 production.

Cellular movement and adhesion are a fundamental biological response to external stimuli. During an inflammatory response, leukocytes must leave the plasma compartment and migrate to the point of antigenic insult. The mechanism of this migratory event is a complex interplay between soluble mediators and membrane-bound cellular adhesion molecules. Soluble cellular chemotactic factors, which are produced in the damaged tissue by a variety of resident cells, set up a chemical concentration gradient out to the plasma compartment. Interaction of these factors with their receptors on leukocytes leads to a directional migration of the leukocytes toward increasing concentrations of the chemotactic factor. Simultaneously, various adhesion molecules are upregulated on the leukocyte which mediate the initial rolling on the endothelial tissue, binding to a specific ligand on the activated endothelial tissue, and finally migration between endothelial cells into the tissue. The steps in this cascade of events are mediated by the interaction of specific cell surface proteins, termed "cell adhesion molecules (CAM)". E-selectin (ELAM-1, endothelial leukocyte adhesion molecule-1), ICAM-1 (intercellular adhesion molecule-1), and VCAM-1 (vascular cell adhesion molecule-1) are three major adhesion molecules the expression of which on endothelial cells is upregulated upon treatment with inflammatory stimuli. ICAM-1 is expressed at low levels on resting endothelium and is markedly induced in response to cytokines such as IL-1, TNF and interferon-$\gamma$ (IFN-$\gamma$). VCAM-1 is not expressed in resting endothelium but is induced by IL-1, TNF and IL-4. Induction of both ICAM-1 and VCAM-1 occurs 4 to 6 hours after cytokine treatment and cell surface expression remains elevated for up to 72 hours after treatment with cytokines. On the other hand, induction of transcription of the E-selectin gene by cytokines such as IL-1 and TNF results in an increase in the expression on the surface of endothelial cells peaking approximately 4–6 hours after challenge, and returns toward a basal level of expression by 24 hours.

The concept of anti-CAM therapy has been validated by the demonstration that MAbs against ICAM-1 and antisense oligonucleotide against ICAM-1 showed therapeutic efficacy in a variety of preclinical and clinical studies (A. F. Kavanaugh et al., *Arthritis Rheum,* 1994, 37, 992; C. E. Haug et al., *Transplantation,* 1993, 55, 766; and J. E. Jr. Sligh et al., *Proc. Natl. Acad. Sci.,* 1993, 90, 8529). Further support comes from the reports of the in vivo activity of sLeX and related carbohydrates, which are antagonists of E-selectin mediated adhesion ( M. S. Mulligan et al., *Nature,* 1993, 364, 149–151). Thus, the potential therapeutic targets for CAM inhibitors range from, but are not limited to, RA, IBD and psoriasis to ischemia/reperfusion injury, autoimmune diabetes, organ transplantation, ARDS, tumor metastases and AIDS, as is evident from the many ongoing development activities. The regulation of the functions of CAM is of benefit in controlling, reducing and alleviating many of these disease states. There remains a need for compounds which are capable of inhibiting cytokine production and/or CAM expression. The pyridylfuran and pyridylthiophene compounds of the present invention are shown herein in an in vitro assay to inhibit cytokine production and/or CAM expression.

Japanese Kokai (laid-open) Publication Number H02-289548 discloses aryl substituted pyridine compounds as anti-ischemia agents. Japanese Kokai (laid-open) Publication Number H03-232884 discloses a variety of thiophene compounds as a herbicide.

BRIEF DISCLOSURE OF THE INVENTION

The present invention provides a compound of the formula:

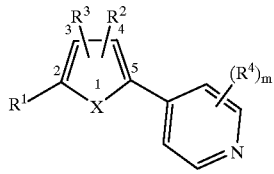

(I)

and its pharmaceutically effective salts, wherein $R^1$ and $R^2$ are independently selected from the following:

(a) hydrogen, halo, $R^5$—, $R^6$—, $C_{2-6}$ alkenyl, $C_{2-6}$ alkynyl, hydroxy-$R^5$—, $R^5$—O—, $R^5$—S—, hydroxy-$R^6$—, $R^5$—O—$R^5$—, mercapto-$R^5$—, $R^5$—S—$R^5$—, —NH$_2$, $R^5$—NH—, $R^6$—NH—, $(R^5)_2$—N— or heterocyclic group optionally substituted by one or two substituents selected from $C_{1-4}$ alkyl phenyl and pyridyl;

(b) Ar—, Ar—$R^5$—, Ar—$C_{2-6}$ alkenyl, Ar—$C_{2-6}$ alkynyl, Ar—O—, Ar—O—Ar—, Ar—O—Ar—O—, Ar—O—$R^5$—, Ar—$R^5$—O—, Ar—S—, Ar—$R^5$—S—, Ar—NH—, $(Ar)_2$—$R^5$—, Ar—$R^5$—NH—, Ar—$R^5$—N($R^5$)— or $(Ar)_2$—N—;

(c) $R^5$—C(O)—, —NO$_2$, cyano, NH$_2$—C(O)—, $R^5$—NH—C(O)—, $(R^5)_2$—N—C(O)—, Ar—C(O)—, (Ar—$R^5$)$_2$—N—C(O)—, Ar—$R^5$—C(O)—, Ar—NH—C(O)—, Ar—$R^5$—NH—C(O)—, $R^5$—S(O)$_2$— or $R^5$—S(O)—; and (d) $R^5$—C(O)—NH—, Ar—C(O)—NH—, Ar—$R^5$—C(O)—NH— or H$_2$N—C(O)—NH—;

wherein Ar is aryl or heteroaryl optionally substituted with one or two substituents selected from $C_{1-4}$ alkyl, halo-substituted $C_{1-4}$ alkyl, halo-substituted $C_{1-4}$ alkoxy, $C_{1-4}$ alkylthio, nitro, hydroxy, amino and halo; and wherein $R^5$ is $C_{1-6}$ alkyl optionally substituted by up to four (preferably up to three) halogen atoms and $R^6$ is $C_{3-8}$ cycloalkyl optionally substituted by up to four (preferably up to three) halogen atoms;

$R^3$ is selected from the following:

(e) $R^6$, $R^5$, cyano, formyl $R^5$—C(O)— $R^6$—C(O)—, $C_{2-6}$ alkenyl-C(O)—, $C_{2-6}$ alkynyl-C(O)—, $R^5$—C(O)—$R^5$—, $R^6$—C(O)—$R^5$—, $R^5$—C(O)—$R^6$—, $R^6$—C(O)—$R^6$—, $C_{2-6}$ alkenyl-C(O)—$R^5$—, $C_{2-6}$ alkynyl-C(O)—$R^5$—, $R^5$—C(O)—$C_{2-6}$ alkenylene—, $R^5$—C(O)—$C_{2-6}$ alkynylene—, $R^5$—O—C(O)—$R^5$—, $R^6$—O—C(O)—$R^5$—, $R^5$—O—C(O)—$C_{2-6}$ alkenylene—, $R^5$—O—C(O)—$C_{2-6}$ alkynylene—, $R^5$—S—C(O)—, $R^5$—O—C(O)—, H$_2$N—C(O)—, H$_2$N—C(O)—$R^5$—, $R^5$—NH—C(O)—, $R^6$—NH—C(O)—, $R^5$—NH—C(O)—$R^5$—, $R^6$—NH—C(O)—$R^5$—, $(R^5)_2$—N—C(O)—, $(R^5)_2$—N—C(O)—$R^5$—, H$_2$N—C(O)—$C_{2-6}$ alkenylene—, $R^5$—NH—C(O)—$C_{2-6}$ alkenylene—, $R^6$—NH—C(O)—$C_{2-6}$ alkenylene—, $(R^5)_2$—N—C(O)—$C_{2-6}$ alkenylene—, $R^5$—O—$R^5$—O—, $R^5$—O—$R^5$—, HO—$R^5$—, $R^5$—O—$R^6$—, HO—$R^6$— or Ar;

(f) $R^5$—C(O)—NH—, Ar—C(O)—NH—, Ar—$R^5$—C(O)—NH—, —NH$_2$, $R^5$—NH—, $(R^5)_2$—N—, —$R^6$—NH$_2$, —$R^5$—NH$_2$, $R^5$—NH—$R^5$—, $R^6$—NH—$R^5$—, $R^5$—NH—$R^6$—, $(R^5)_2$—N—$R^5$—, H$_2$N—C(O)—NH—, $R^5$—NH—C(O)—NH—, $(R^5)_2$—N—C(O)—NH—, Ar—NH—C(O)—NH—, $(Ar)_2$—N—C(O)—NH—, HO—N=C($R^5$)—, HO—N=C—, HO—N=CH—$R^5$—, HO—N=CH—$R^6$—, $R^5$—C(O)—O—N=CH—, $R^5$O—N=CH—, $R^6$O—N=CH—, $R^5$O—N=C($R^5$)—, $R^5$O—N=C($R^5$)—, $R^5$O—N=C($R^6$)—, $R^5$O—N=CH—$R^5$—, $R^6$O—N=CH—$R^5$—, $R^5$O—N=CH—$R^6$—, $R^6$O—N=CH—$R^6$—, HO—NH—, $R^5$O—NH—, HO—N($R^5$)—, $R^5$O—N($R^5$)—, HO—NH—$R^5$—, $R^5$O—NH—$R^5$—, HO—N($R^5$)—$R^5$— or $R^5$O—N($R^5$)—$R^5$—;

(g) $R^5$—S—, Ar—S—, $R^5$—S(O)—, $R^5$—NH—S(O)$_2$—, $R^5$—S(O)$_2$—, —S(O)$_2$NH$_2$, —S(O)NH$_2$, $R^5$—NH—S(O)—, Ar—S(O)—, Ar—$R^5$—S(O)—, Ar—S(O)$_2$—, $C_{2-6}$ alkenyl—S(O)$_2$—, $C_{2-6}$ alkynyl—S(O)$_2$—, Ar—$R^5$—S(O)$_2$—, Ar—NH—S(O)$_2$—, Ar—$R^5$NH—S(O)$_2$—, Ar—NH—S(O)— or Ar—$R^5$—NH—S(O)—; and (h) Ar—C(O)—, Ar—$R^5$—C(O)—, Ar—C(O)—$R^5$—, Ar—C(O)—$R^6$—, Ar—C(O)—$C_{2-6}$ alkenylene—, Ar—$R^5$—C(O)—, Ar—$R^5$—C(O)—$R^5$—, Ar—$R^5$—C(O)—$C_{2-6}$ alkenylene—, Ar—$C_{2-6}$ alkenylene-C(O)—, Ar—$C_{2-6}$ alkynylene-C(O)—, Ar—$C_{2-6}$ alkenylene-C(O)—$R^5$—, Ar—$C_{2-6}$ alkynylene-C(O)—$R^5$—, Ar—O—$R^5$—C(O)—, Ar—S—$R^5$—C(O)—, Ar—$R^5$—S—C(O)—, Ar—NH—C(O)—, Ar—$R^5$—NH—C(O)—, $(Ar)_2$—$C_{2-6}$ alkenylene-C(O)—, $(Ar)_2$—$C_{2-6}$ alkynylene-C(O)—, $(Ar)_2$—$R^5$—S—C(O)—, $(Ar)_2$—N—C(O)— or $(Ar)_2$—$R^5$—NH—C(O)—;

wherein Ar, $R^5$ and $R^6$ are as defined above; or two of $R^1$, $R^2$ and $R^3$ together form a group of the formula —$A^1$—$B^1$—$A^2$— or —$A^1$—$B^1$—$A^3$—$B^2$—$A^2$— which, together with the carbon atoms to which $A^1$ and $A^2$ are attached, defines a ring having 4 to 8 ring atoms, the ring optionally being substituted with acetyl, —C(O)—OH, —C(O)—NH$_2$, —C(O)—O$R^5$, —C(O)—NH$R^5$, hydroxy, $R^5$—, $C_{1-4}$ alkoxy, $R^5$—NH—, $R^6$—NH—, $(R^5)_2$N—, piperidino, piperazino, pyrrolidino or Ar, wherein $A^1$ and $A^2$ are independently a direct bond or $C_{1-6}$ alkylene and $A^3$ is $C_{1-4}$ alkylene and $B^1$ and $B^2$ are independently a direct bond, O, S, S(O), S(O)$_2$, C(O) or N$R^5$;

$R^4$ is selected from the following:

(i) hydrogen, halo, $R^5$—, hydroxy-$R^5$— or $R^5$—O—$R^5$—; and (j) $R^5$—C(O)—, $R^5$—O—C(O)— or $R^5$—NH—C(O)—; or two of $R^4$ which are attached to adjacent carbon atoms on the pyridine ring complete a fused benzene ring, the benzene ring being optionally substituted with one or two substituents selected from $C_{1-4}$ alkyl, halo-substituted $C_{1-4}$ alkyl, halo-substituted $C_{1-4}$ alkoxy, nitro, hydroxy, amino and halo; wherein $R^5$ is as defined above;

X is O, S, S(O) or S(O)$_2$;

m is 0, 1,2,3 or4; and the nitrogen atom of the pyridyl ring attached to the 5-position of the furan or the thiophene ring is optionally replaced by a N oxide group.

The present invention also relates to a pharmaceutical composition for treating a disorder or condition selected from AIDS, ARC, arthritis, asthma, bone resorption disease, cachexia, cardiovascular disease including atherosclerosis, cerebral malaria, Crohn's disease, diabetes, fever or myalgia due to infection, gout, graft versus host reaction, inflammation of organs, inflammatory bowel disease, keloid formation, psoriasis, pulmonary inflammatory disease, respiratory distress syndrome, reperfusion injury, rhinitis, scar tissue formation, sepsis, septic shock, silicosis, toxic shock syndrome, transplant rejection, ulcerative colitis, and other disorders and conditions that are cytokine- or CAM-mediated, in a mammal, comprising an amount of the compound of formula (I), or a pharmaceutically effective salt thereof, that is effective in treating such disorder or condition, and a pharmaceutically acceptable carrier.

The invention also relates to a method of treating a disorder or condition selected from AIDS, ARC, arthritis, asthma, bone resorption disease, cachexia, cardiovascular disease including atherosclerosis, cerebral malaria, Crohn's disease, diabetes, fever or myalgia due to infection, gout, graft versus host reaction, inflammation of organs, inflammatory bowel disease, keloid formation, psoriasis, pulmonary inflammatory disease, respiratory distress syndrome, reperfusion injury, rhinitis, scar tissue formation, sepsis, septic shock, silicosis, toxic shock syndrome, transplant rejection, ulcerative colitis, and other disorders or conditions that are cytokine- or CAM-mediated, in a mammal, comprising administering to a mammal in need of such treatment an amount of a compound of formula (I), or a pharmaceutically effective salt thereof, that is effective in treating such a disorder or condition.

The invention also relates to a pharmaceutical composition for treating a disorder or condition, the treatment of which can be effected or facilitated by reducing or inhibiting a cytokine mediator or CAM mediator of said disorder or condition in a mammal, comprising an amount of a compound of formula (I), or a pharmaceutically effective salt thereof, that is effective in treating such disorder or condition, and a pharmaceutically acceptable carrier.

The invention also relates to a method for treating a disorder or condition, the treatment of which can be effected or facilitated by reducing or inhibiting a cytokine mediator or CAM mediator of said disorder or condition in a mammal, comprising administering to a mammal in need of such treatment an amount of a compound of formula (I), or a pharmaceutically effective salt thereof, that is effective in treating such disorder or condition.

DETAILED DESCRIPTION OF THE INVENTION

The term "treating" as used herein refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

As used herein, the term "alkyl" means straight or branched chain saturated radicals of 1 to 12 carbon atoms. More preferred alkyl radicals are lower alkyl radicals having one to about 6 atoms, including, but not limited to methyl, ethyl, n-propyl, isopropyl, n-butyl, isobutyl, secondary-butyl, tertiary-butyl, and the like.

As used herein, the term "cycloalkyl" means carbocyclic saturated radicals, of 3 to 8 carbon atoms, including, but not limited to cyclopropyl, cyclobutyl, cyclopentyl, cyclohexyl, and the like.

As used herein, the term "alkenyl" means straight or branched chain unsaturated radicals of 2 to 12 carbon atoms. More preferred alkenyl radicals are lower alkenyl radicals having one to about 6 atoms, including, but not limited to ethenyl, 1-propenyl, 2-propenyl (allyl), isopropenyl, 2-methyl-1-propenyl, 1-butenyl, 2-butenyl, and the like. The double bonds of these substituents are preferably separated from the remaining part of the compound I by at least one saturated carbon atom. There may be mentioned also by way of example vinyl, prop-2-en-1-yl, 2-methylprop-2-en-1-yl, but-2-en-1-yl and but-3-en-1-yl.

As used herein, the term "halosubstituted alkyl" refers to an alkyl radical as described above substituted with one or more halogens included, but not limited to, chloromethyl, fluoromethyl, difluoromethyl, trifluoromethyl, 2,2,2-trichloroethyl, and the like.

As used herein, the term "alkenylene" means a straight or branched hydrocarbon chain spacer radical having one double bond including, for example, —CH=CH—, —CH=CHCH,—, —CH=CHCH(CH$_3$)—, and the like.

As used herein, the term "alkynyl" is used herein to mean straight or branched hydrocarbon chain radicals having one triple bond including, but not limited to, ethynyl, propynyl, butyyl and the like.

As used herein, the term "alkynylene" means a straight or branched hydrocarbon chain spacer radical having one triple bond including, for example, —C≡C—, —C—≡CCH$_2$—, —C≡CCH(CH$_3$)—, and the like.

As used herein, the term "aryl" means aromatic radicals such as phenyl, naphthyl, tetrahydronaphthyl, indane and biphenyl, and the like.

As used herein, the term "heterocyclic" means saturated heteroatom-containing ring-shaped radicals, where the heteroatoms may be selected from nitrogen, sulfur and oxygen. Examples of saturated heterocyclic radicals include saturated 3 to 6-membered heteromonocyclic groups containing 1 to 4 nitro-en atoms [e.g. pyrrolidinyl, imidazolidinyl, piperidino, piperidinyl, piperazinyl, etc.]; saturated 3 to 6-membered heteromonocyclic groups containing 1 to 2 oxygen atoms and 1 to 3 nitrogen atoms [e.g. morpholino, morpholinyl, etc.]; saturated 3 to 6-membered heteromonocyclic groups containing 1 to 2 sulfur atoms and 1 to 3 nitrogen atoms [e.g. thiazolidinyl, etc.].

As used herein, the term "heteroaryl" means unsaturated heterocyclic radicals. Examples of heteroaryl radicals include unsaturated 5 to 6 membered heterocyclic groups containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g. 4H-1,2,4-triazolyl, 1H-1,2,3-triazolyl, 2H-1,2,3-triazolyl, etc.], tetrazolyl [1H-tetrazolyl, 2H-tetrazolyl, etc.], unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], unsaturated 3 to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5 to 6-membered heteromonocyclic groups containing 1 to 2 oxygen atoms and 1 to3 nitrogen atoms, for example, oxazolyl, isoxazolyl, oxadiazolyl [e.g., 1,2,4-oxadiazolyl, etc.]; unsaturated condensed heterocyclic groups containing 1 to 2 oxygen atoms and 1 to 3 nitrogen atoms [e.g., benzoxazolyl, etc.]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, etc.]; unsaturated condensed heterocyclic groups containing 1 to 2 sulfur atoms and 1 to 3 nitrogen atoms [e.g., benzothiazolyl, etc.], and the like. The term also means radicals where heterocyclic radicals are fused with aryl radicals. Examples of such fused bicyclic radicals include benzofuran, benzothiophene, and the like.

As used herein, the term "halo" means fluoro, chloro, bromo and iodo.

As used herein, the term "N oxide group" means a group represented by the following formula:

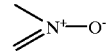

As used herein, the term "equivalent of $R^{2a}$—C(O)—CH$_2$—R$^7$" means compounds with similar reactivity to $R^{2a}$—C(O)—CH$_2$—R$^7$, or compounds which can be transformed to $R^{2a}$—C(O)—CH$_2$—R$^7$ in situ, such as enamine equivalent $R^{2a}$ C(NH$_2$)=CH—R$^7$, or enotether equivalent $R^{2a}$C(OR$^{3a}$)=CH—R$^7$.

In the formula (I), a substituent of substituted R$^6$ (for example, hydroxy-R$^6$—, carboxy-R$^6$—, R$^6$—O—R$^6$—, etc.) may be attached to any carbon atom of the R$^6$.

In the group "(Ar)$_2$—R$^6$—", two of Ar may be the same or different from each other, and may be attached to a same carbon atom or different carbon atoms of R$^6$.

A preferred group of compounds of this invention includes the compound of the formula (I) wherein the heterocyclic group is selected from piperidino, piperidinyl, piperazinyl, pyrrolidinyl, imidazolidinyl and morpholino; and the aryl or heteroaryl group is selected from phenyl, naphthyl, pyridyl, quinolyl, thienyl, furyl, pyrrolyl, indolyl, benzothienyl and benzofuryl.

Also, a preferred group of compounds of this invention includes the compound of the formula (I) wherein R$^1$ is selected from group (a), (b) and (c); R$^2$ is selected from group (a), (b) and (c); R$^3$ is selected from group (e), (f), (g) and (h); and R$^4$ is selected from group (i); or two of R$^1$, R$^2$ and R$^3$ together form a group of the formula —A$^1$—B$^1$—A$^2$— or —A$^1$—B$^1$—A$^3$—B$^2$—A$^2$—; X is O or S; and m is 0, 1 or 2.

A further preferred compound of the invention includes the compound of formula (I) wherein R$^1$ is Ar—O—, Ar—O—Ar—O—, Ar—R$^5$—N(R$^5$)—, R$^5$—S(O)$_2$—, R$^5$—S(O)—, hydrogen, R$^5$—S—, R$^5$—O—, a heterocyclic group selected from piperidino, piperidinyl, piperazinyl and morpholino, the heterocyclic group being optionally substituted by one or two of C$_{1-4}$ alkyl, phenyl or pyridyl, halo, R$^5$—, R$^5$—C(O)— or Ar optionally substituted with C$_{1-4}$ alkyl, hydroxy, nitro, C$_{1-4}$ alkylthio, halo-substituted C$_{1-4}$ alkyl, C$_{1-4}$ alkoxy or halo, R$^2$ is hydrogen, halo, R$^5$—, Ar— or R$^5$—C(O)—, wherein the aryl or heteroaryl ring of Ar is optionally substituted with C$_{1-4}$ alkyl, hydroxy, nitro or halo; R$^3$ is R$^5$—, R$^5$—C(O)—, Ar, R$^5$—NH—C(O)—, R$^5$—C(O)—NH—, cyano, formyl, R$^5$—O—C(O)—R$^5$—, R$^5$—O—C(O)—, H$_2$N—C(O)—, H$_2$N—C(O)—R$^5$—, HO—N=CH—, R$^5$O—N=CH—, R$^5$—C(O)—O—N=CH—, HO—NH—R$^5$—, Ar—C(O)— or Ar—S(O)$_2$—; R$^2$ and R$^3$ are at the 4 and 3-positions of the furan or the thiophene ring, respectively; or two of R$^1$, R$^2$ and R$^3$ together form a group of the formula —A$^1$—B$^1$—A$^2$— or —A$^1$—B$^1$—A$^3$—B$^2$—A$^2$— which, together with the carbon atoms to which A$^1$ and A$^2$ are attached, defines a ring having 5 to 7 ring atoms, the ring optionally being substituted with acetyl, hydroxy, R$^5$—, C$_{1-4}$ alkoxy, wherein A$^1$ and A$^2$ are independently a direct bond or C$_{1-6}$ alkylene and A$^3$ is C$_{1-4}$ alkylene and B$^1$ and B$^2$ are independently a direct bond, O, S, S(O) or C(O); and m is 0.

A further preferred compound of the invention includes the compound of formula (I) wherein R$^1$ is hydrogen, fluoro, chloro, C$_{1-4}$ alkyl, C$_{1-4}$ alkylthio, C$_{1-4}$ alkyl-C(O)—, phenoxy optionally substituted with one or two fluorine atoms, piperidino, piperazinyl optionally substituted by C$_{1-4}$ alkyl, morpholino, halophenoxyphenoxy, phenyl-C$_{1-4}$ alkyl-N (C$_{1-4}$ alkyl)—, C$_{1-4}$ alkyl-S(O)$_2$—, phenyl, pyridyl or thienyl, wherein the phenyl, pyridyl or thienyl is optionally substituted with C$_{1-4}$ alkyl, C$_{1-4}$ alkylthio, C$_{1-4}$ alkoxy, hydroxy, trifluoromethyl, fluoro or chloro; R$^2$ is hydrogen, chloro, fluoro, C$_{1-4}$ alkyl, phenyl, pyridyl or C$_{1-4}$ alkyl-C(O)—; R$^3$ is C$_{1-4}$ alkyl, fluoro-C$_{1-4}$ alkyl, difluoro-C$_{1-4}$ alkyl, cyano, C$_{1-4}$ alkyl-O—C(O)—C$_{1-4}$ alkyl, C$_{1-4}$ alkyl-O—C(O)—, H$_2$N—C(O)—, H$_2$N—C(O)-C$_{1-4}$ alkyl, C$_{1-4}$ alkyl-NH—C(O)—, C$_{1-4}$ alkyl-C(O)—O—N=CH—, C$_{1-4}$ alkyl-O—N=CH—, HO—NH—C$_{1-4}$ alkyl, HO—N=C—, pyrrolyl—S(O)$_2$—, phenyl-C(O)—, formyl, C$_{1-4}$ alkyl-C(O)—, phenyl, pyridyl, C$_{1-4}$ alkyl-NH—C(O)— or C$_{1-4}$ alkyl-C(O)—NH—; —A$^1$—B—A$^2$— is C$_{1-6}$ alkylene-C(O)—C$_{1-6}$ alkylene. C$_{1-6}$ alkylene-C(O)— or —S—CH (acetyl)-C$_{1-4}$ alkylene; and —A$^1$—B$^1$—A$^3$—B$^2$13 A$^2$— is C$_{1-6}$ alkylene-S—C(O)—.

A particularly preferred compound of the invention includes the compound of formula (I) wherein R$^1$ is chloro, methyl, ethyl, phenyl, 4-pyridyl, isopropyl, isobutyl, acetyl, hydrogen, 4-methoxyphenyl, 4-chlorophenyl, 4-trifluorophenyl, 4-fluorophenyl, thienyl, 4-methylthiophenyl, morpholino, 4-methylpiperazinyl, N-benzyl-N-methylamino, phenoxy, 3-(4-fluorophenoxy)-phenoxy, methyl-S(O)$_2$—, methylthio, piperidino, 2-fluorophenyl, 2-fluorophenoxy, 2,5-difluorophenoxy or 4-fluorophenoxy; R$^2$ is hydrogen, methyl, ethyl, acetyl, pyridyl or phenyl; R$^3$ is methyl, ethyl, pyridyl, acetyl, propanoyl, acetamino, methylaminocarbonyl, 1-hydroxyethyl, methoxycarbonyl, pyrrolinine-1-sulfonyl, cyano, phenyl-C(O)—, formyl, HO—N=C—, CH$_3$—C(O)—(CH$_2$)$_2$—, (CH$_3$)$_2$N—C(O)—(CH$_2$)$_2$—, ethoxy-C(O)—(CH$_2$)$_2$—, methylamino-C(O)—, CH$_3$—C(O)—O—N=CH—, H$_2$N—C(O)—, isopropoxy-C(O)—, CH$_3$O—N=CH—, difluoromethyl, fluoromethyl, HO—NH—CH$_2$— or H$_2$N—C(O)—(CH$_2$)$_2$—; —A$^1$—B—A$^2$— is selected form —(CH$_2$)$_3$—C(O)—, —(CH$_2$)$_2$—C(CH$_3$)$_2$—C(O)—, —C(CH$_3$)$_2$—(CH$_2$)$_2$—C(O)—, —(CH$_2$)$_4$—C(O)—, —(CH$_2$)$_2$—C(O)—, —S—CH(acetyl)-CH(CH $_3$)— and —C(O)—(CH$_2$)$_2$—; and —A$^1$—B$^1$—A$^3$—B$^2$—A$^2$— is —CH$_2$—CH(CH$_3$)—O—C(O)—.

A particularly preferred compound of the invention also includes the compound of formula (I) wherein R$^1$ is chloro, methyl, ethyl, phenyl, 4-pyridyl, isopropyl, isobutyl or acetyl; R$^2$ is hydrogen, methyl, ethyl or acetyl; R$^3$ is methyl, ethyl, pyridyl, acetyl or propanoyl; and —A$^1$—B—A$^2$— is —(CH$_2$)$_2$—C(O)— or —(CH$_2$)$_3$—C(O)—.

Among the compounds of the formula (I), particularly preferred individual compounds are one of the following:

3-acetyl-2,4-dimethyl-5-(4-pyridyl)furan;

3-methyl-4-oxo-2-(4-pyridyl)-4,5,6,7-tetrahydrobenzofuran;

3-acetyl-4-methyl-2-phenyl-5-(4-pyridyl)furan;

3-acetoamino-2,4-dimethyl-5-(4-pyridyl)furan;

2,4-dimethyl-3-methylaminocarbonyl-5-(4-pyridyl) furan;

4-oxo-2-(4-pyridyl)-3,5,5-trimethyl-4,5,6,7-tetrahydrobenzofuran;

4-oxo-2-(4-pyridyl)-3,7,7-trimethyl-4,5,6,7-tetrahydrobenzofuran;

3-methyl-4-oxo-2-(4-pyridyl)cyclohepteno(b)furan;

3-acetyl-2-isobutyl-4-methyl-5-(4-pyridyl)furan hydrochloride;

6,7-dihydro-3,6-dimethyl-2-(4-pyridyl)-furo[3,2-c]pyran-4-one;

3-ethyl-7,7-dimethyl-4-oxo-2-(4-pyridyl)-4,5,6,7-tetrahydrobenzofuran;

7,7-dimethyl-3-phenyl-4-oxo-2-(4-pyridyl)-4,5,6,7-tetrahydrobenzofuran;

2-acetyl-4-methyl-3,5-di(4-pyridyl)thiophene;

2-acetyl-3-methyl-4,5-di(4-pyridyl)thiophene;

3-acetyl-4-methyl-2,5-di(4-pyridyl)thiophene;

4-oxo-2-(4-pyridyl)-4,5,6,7-tetrahydro-benzo(b)thiophene;

3-acetyl-5-chloro-4-methyl-2-(4-pyridyl)thiophene;

3-acetyl-2,4-dimethyl-5-(4-pyridyl)thiophene;

3-acetyl-4-methyl-2-phenyl-5-(4-pyridyl)thiophene;

3-methyl-4-oxo-2-(4-pyridyl)-4,5,6,7-tetrahydrobenzothiophene;

2,5-di(4-pyridyl)-3-(1-hydroxyethyl)-4-methylthiophene;

1,3-di(4-pyridyl)-5,6-dihydro-4H-cyclopenta(c)thiophen-4-one;

2,5-di(4-pyridyl)-3-methoxycarbonylthiophene;

3-acetyl-2,5-di(4-pyridyl)thiophene;

2,5-di(4-pyridyl)-3-(pyrrolidine-1-sulfonyl)thiophene;

2,5-di(4-pyridyl)-3-ethyl-4-methylthiophene dihydrochloride;

4-acetyl-3-methyl-2-(4-pyridyl)thiophene;

3-acetyl-2-(4-methoxyphenyl)-4-methyl-5-(4-pyridyl)thiophene hydrochloride;

3-cyano-2,5-di(4-pyridyl)thiophene;

3-acetyl-2-(4-chlorophenyl)-4-methyl-5-(4-pyridyl)thiophene hydrochloride;

3-acetyl-4-methyl-2-(4-trifluoromethylphenyl)-5-(4-pyridyl)thiophene hydrochloride;

3-acetyl-2-(4-fluorophenyl)-4-methyl-5-(4-pyridyl)thiophene;

3-benzoyl-2,5-di(4-pyridyl)thiophene;

2,5-di(4-pyridyl)-4-methylthiophene-3-carbaldehyde;

3-acetyl-4-methyl-5-(4-pyridyl)-2-(3-thienyl)thiophene;

3-acetyl-4-methyl-5-(4-pyridyl)-2-(4-methylthiophenyl)thiophene;

3-acetyl-2-(4-morpholino)-5-(4-pyridyl)thiophene;

3-acetyl-2-(4-methylpiperazin-1-yl)-5-(4-pyridyl)thiophene;

2,5-di(4-pyridyl)-4-methylthiophene-3-carbaldehyde oxime dihydrochloride;

3-acetyl-2-(N-benzyl-N-methylamino)-5-(4-pyridyl)thiophene hydrochloride;

1,3-di(4-pyridyl)-4,5,6,7-tetrahydrobenzo(c)thiophen-4-one;

3-acetyl-2-phenoxy-5-(4-pyridyl)thiophene;

2-acetyl-3,4-dimethyl-5-(4-pyridyl)thieno[2,3-b]thiophene;

3-acetyl-2-{3-(4-fluorophenoxy)phenoxy}-5-(4-pyridyl)thiophene hydrochloride;

1-chloro-3-(4-pyridyl)-4,5,6,7-tetrahydrobenzo(c)thiophen-4-one;

3-methanesulfonyl-1-(4-pyridyl)-4,5,6,7-tetrahydrobenzo(c)thiophen4-one;

3-methylthio-1-(4-pyridyl)-4,5,6,7-tetrahydrobenzo(c)thiophen-4-one;

[2,5-di-(4-pyridyl)3-thienyl]butan-3-one;

N,N-dimethyl-3-[2,5-di-(4-pyridyl)3-thienyl]propionamide;

3-acetyl-2-(1-piperidino)-5-(4-pyridyl)thiophene;

ethyl 3-[2,5-di-(4-pyridyl)3-thienyl]propionate dihydrochloride;

N-methyl-{2,5-di(4-pyridyl)thiophen-3-yl}carboxamide;

3-(2-fluorophenyl)-1-(4-pyridyl)-5,6-dihydro-4H-cyclopenta(c)thiophene-4-one;

1-chloro-3-(4-pyridyl)-5,6-dihydro-4H-cyclopenta(c)thiophene-4-one;

O-acetyl-2,5-di(4-pyridyl)-4-methylthiophene-3-carbaldehyde oxime;

3-acetyl-2-(2-fluorophenoxy)-5-(4-pyridyl)thiophene;

3-acetyl-2-(2,5-difluorophenoxy)-5-(4-pyridyl)thiophene;

3-(4-fluorophenyl)-1-(4-pyridyl)-5,6-dihydro-4H-cyclopenta(c)thiophene-4-one;

2,5-di(4-pyridyl)-3-thiophenecarboxamide;

3-(isopropyloxycarbonyl)-2,5-di(4-pyridyl)thiophene;

O-methyl-2,5-di(4-pyridyl)-4-methylthiophene-3-carbaldehyde oxime dihydrochloride;

3-acetyl-2-(4-fluorophenoxy)-5-(4-pyridyl)thiophene;

1-(4-pyridyl)-3-(3-pyridyl)-5,6-dihydro-4H-cyclopenta(c)thiophene-4-one;

3-difluoromethyl-2,5-di(4-pyridyl)-4-methylthiophene;

2,5-di(4-pyridyl)-3-fluoromethyl-4-methylthiophene;

1-(4-pyridyl)-3-(4-trifluoromethylphenyl)-5,6-dihydro-4H-cyclopenta(c)thiophene-4-one;

1-(4-fluorophenyl)-3-(4-pyridyl)-5,6-dihydro-4H-cyclopenta(c)thiophene-4-one;

3-(N-benzyl-N-methylamino)-1-(4-pyridyl)-5,6-dihydro-4H-cyclopenta(c)thiophene-4-one;

[2,5-di(4-pyridyl)-4-methylthiophen-3-yl]methylhydroxylamine trihydrochloride; and 3-[2,5-di-(4-pyridyl)3-thienyl]propionamide.

Among the compounds of the formula (I), the most preferred individual compounds are one of the following:

3-acetyl-2,4-dimethyl-5-(4-pyridyl)furan;

3-methyl-4-oxo-2-(4-pyridyl)-4,5,6,7-tetrahydrobenzofuran;

4-oxo-2-(4-pyridyl)-3,7,7-trimethyl-4,5,6,7-tetrahydrobenzofuran;

3-ethyl-7,7-dimethyl-4-oxo-2-(4-pyridyl)-4,5,6,7-tetrahydrobenzofuran;

3-acetyl-4-methyl-2,5-di(4-pyridyl)thiophene;

1,3-di(4-pyridyl)-5,6-dihydro-4H-cyclopenta(c)thiophen-4-one;

2,5-di(4-pyridyl)-3-methoxycarbonylthiophene;

3-acetyl-2,5-di(4-pyridyl)thiophene;

2,5-di(4-pyridyl)-3-ethyl-4-methylthiophene dihydrochloride;

3-acetyl-2-(4-chlorophenyl)-4-methyl-5-(4-pyridyl)thiophene hydrochloride;

3-acetyl-4-methyl-2-(4-trifluoromethylphenyl)-5-(4-pyridyl)thiophene hydrochloride;

3-acetyl-2-(4-fluorophenyl)-4-methyl-5-(4-pyridyl)thiophene, 3-benzoyl-2,5-di(4-pyridyl)thiophene;

2,5-di(4-pyridyl)-4-methylthiophene-3-carbaldehyde;

2,5-di(4-pyridyl)-4-methylthiophene-3-carbaldehyde oxime dihydrochloride;

1,3-di(4-pyridyl)-4,5,6,7-tetrahydrobenzo(c)thiophen-4-one;

3-methylthio-1-(4-pyridyl)-4,5,6,7-tetrahydrobenzo(c)thiophen-4-one;

[2,5-di-(4-pyridyl)3-thienyl]butan-3-one;

N,N-dimethyl-3-[2,5-di-(4-pyridyl)3-thienyl]propionamide;

O-acetyl-2,5-di(4-pyridyl)-4-methylthiophene-3-carbaldehyde oxime;

3-(isopropyloxycarbonyl)-2,5-di(4-pyridyl)thiophene;

O-methyl-2,5-di(4-pyridyl)-4-methylthiophene-3-carbaldehyde oxime dihydrochloride;

3-difluoromethyl-2,5-di(4-pyridyl)-4-methylthiophene;
2,5-di(4-pyridyl)-4-fluoromethyl-4-methylthiophene;
[2,5-di(4-pyridyl)-4-methylthiophen-3-yl]
methylhydroxylamine trihydrochloride; and
3-[2,5-di-(4-pyridyl)3-thienyl]propionamide.

General Synthesis

The compounds of this invention can be prepared by a variety of synthetic routes. Representative procedures are outlined as follows.

1. Synthesis of Pyridylfurans and Pyridyithiophenes by Palladium Catalyzed Cross Coupling The compounds of formula (I) can be prepared by using the method of Stille or Suzuki (for example, Snieckus V. et al., *J Org. Chem.*, 1995, 60, 292, Stille, J. K. *Angew. Chem. Int. Ed. Engl.*, 1986, 25, 508, Mitchell, M. B. et al., *Tetrahedron Lett.*, 1991, 32, 2273, Matteson, D. S., Tetrahedron, 1989, 45, 1859).

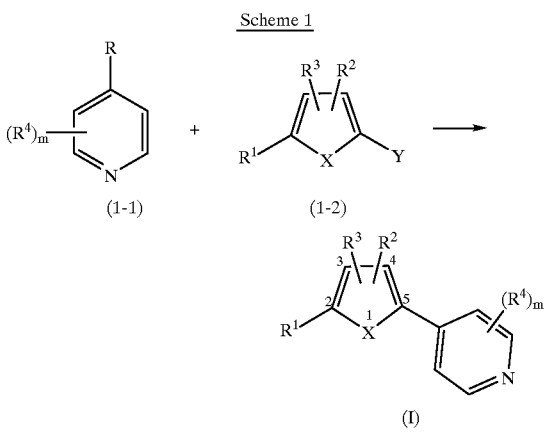

Scheme 1

(wherein R is an organometallic group such as trialkylstannyl, dialkylboronyl, boric acid or zinc halide such as zinc chloride, zinc bromide or zinc iodide; $R^1$, $R^2$, $R^3$, $R^4$ and X are as already defined above; and Y is halo such as Cl, Br or I)

As shown in Scheme 1, the pyridylfuran and pyridylthiophene compounds (I) can be prepared by a reaction of compound (1-1) with furyl or thienyl halides (1-2), in the presence of a catalyst, preferably tetrakis (triphenylphosphine)palladium or bis(triphenylphosphine) palladium(II) chloride, in the inert solvent such as benzene, toluene, xylene, tetrahydrofuran, dioxane, dimethylformamide, preferably dioxane under suitable conditions. The thiophene oxide (I, X=S(O)) or thiophene dioxide (I, X=S(O)$_2$) compounds can be also prepared by a reaction of compound (1-1) with thiophene oxide halide (1-2, X=S(O)) or thiophene dioxide halide (1-2, X=S(O)$_2$) in a similar reaction condition.

The reaction of trialkyl(4-pyridyl)stannane (1-1) with furyl or thienyl halides (1-2) may be carried out in an inert solvent such as benzene, toluene, xylene, tetrahydrofuran, dioxane, dimethylformamide, preferably dioxane, typically in the presence of lithium chloride and a catalyst. The catalyst may be selected from those typically employed for the so-called Stille reaction (for example, tetrakis (triphenylphosphine)palladium or bis(triphenylphosphine) palladium(II) chloride). The reaction may be run at a temperature in a range from 20 to 160° C., preferably 60 to 130° C., for 10 minutes to 5 days, usually 30 minutes to 15 hours.

The reaction of dialkyl(4-pyridyl)borane (1-1) with furyl or thienyl halides (1-2) may be carried out in an inert solvent such as benzene, toluene, tetrahydrofuran, preferably toluene, typically in the presence of a base such as potassium hydroxide, triethylamine, sodium ethoxide, sodium acetate or quaternary ammonium halide, preferably potassium hydroxide. The catalyst may be selected from those typically employed for the so-called Suzuki reaction (for example, tetrakis(triphenylphosphine)palladium or bis (triphenyyphosphine)palladium(II) chloride). The reaction is run at a temperature in the range from 20 to 160° C., preferably 60 to 130° C. for 10 minutes to 5 days, usually 30 minutes to 15 hours.

The reaction of 4-pyridineboronic acid (1-1) with furyl or thienyl halides (1-2) may be carried out in a solvent such as benzene, toluene, dimethoxyethane, dimethylformamide, preferably dimethoxyethane, typically in the presence of a base such as potassium hydroxide, triethylamine, sodium bicarbonate, preferably sodium bicarbonate, or a combination of water and above compounds, preferably water and dimethoxyethane. The catalyst may be selected from those typically employed for the so-called Suzuki reaction (for example, tetrakis(triphenylphosphine)palladium, bis (triphenylphosphine)palladium(II) chloride, or {bis (diphenylphosphino)butane}palladium(II) chloride). The reaction is run at a temperature in the range from 20 to 160° C., usually 60 to 130° C. for 10 minutes to 5 days, usually 30 minutes to 15 hours.

The procedures and conditions to carry out these coupling reactions are known to those in the art, and described in several technical literatures. For example, the procedures of Gronowitz, S. et al. and Snieckus, V. et al. for alkylstannanes are described in *J. Het. Chem.*, 1990, 27, 2165, and *J. Org. Chem.*, 1995, 60, 292; the procedure of Terashima, M. et al. for alkyl boranes is in Heterocycles, 1984, 22, 265 and 2471, and in *Chem. Pharm. Bull.*, 1983, 31, 4573; and the procedures of Fischer, F. C., Mitchel, M. B. et al. and McKillop, A. et al. for boric acids are in *J. Red. Trav. Chim. Pays-Bays*, 1965, 84, 439, *Tetrahedron Lett.*, 1991, 32, 2273, and *Tetrahedron*, 1992, 48, 8117.

The 4-organometallopyridines (1-1) (R=Sn, B or Zn) can be prepared according to the procedure of the above literatures. The requisite furyl or thienyl halides (1-2) are either commercially available or can be prepared from the corresponding furans and thiophenes by halogenation known in the art. The furans and thiophenes for halogenation are either commercially available or can be prepared by using methods known in the art, for example, Paal-Knorr's method, Feist-Benary's method. Knorr's method and Hinsberg's method (*Tetrahedron*, 1995, 51, 13271).

The compounds of formula (1-2) ($R^1$=alkylamino, arylamino, or cyclic amino) can be prepared by a reaction of compound (1-3) with an appropriate alkylamine, arylamine or cyclic amine such as piperidine, piperazine, or morpholine, without solvent as shown in Scheme 2. This reaction proceeds at a temperature in the range from 20 to 250° C. preferably 80 to 150° C. for 10 minutes to 3 days, usually 30 minutes to 15 hours. This reaction may also be carried out in the presence of a catalyst, preferably tetrakis (triphenylphosphine)palladium or bis(tri-o-tolylphosphine) palladium(II) chloride, in the inert solvent such as benzene, toluene, xylene, tetrahydrofuran, dioxane, dimethylformamide, preferably dioxane under suitable conditions. The procedures and conditions to carry out these coupling reactions are known to those in the art. (for example, Buchwald, S. L. et al., *Angew. Chem. Int. Ed. Engl.*, 1995, 34, 1348.) This reaction can be applied to (1-4) for the synthesis of (I) as shown in Scheme 3.

Scheme 2

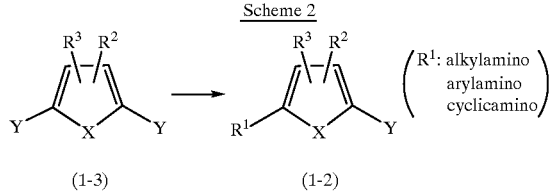

(1-3) → (1-2)  (R¹: alkylamino, arylamino, cyclicamino)

Scheme 3

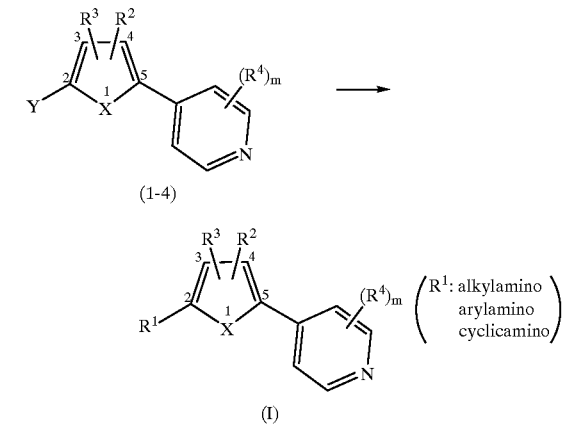

(1-4) → (I)  (R¹: alkylamino, arylamino, cyclicamino)

As shown in Scheme 4, the compounds of formula (1-2) (R¹=alkoxy, aryloxy, alkylthio, arylthio) can be prepared by a reaction of compound (1-3) with an appropriate alcohol or thiol such as alkylalcohol, alkylthiol, phenol or thiophenol and an appropriate base such as sodium hydride, potassium hydride, sodium hydroxide, preferably sodium hydride in the presence of a catalyst such as copper metal, copper(I) iodide, and copper(I) bromide, preferably copper(I) iodide in the inert solvent such as dimethylformamide, dimethylacetamide, N-methylpyrrolidone, dimethylsulfoxide, benzene, toluene, xylene, tetrahydrofuran, dioxane, preferably dimethylformamide. This reaction proceeds at a temperature in the range from 20 to 250° C., preferably 80 to 150° C. for 10 minutes to 3 days, usually 30 minutes to 15 hours. This reaction can be applied to (1-4) for the synthesis of (I) as shown in Scheme 5.

Scheme 4

(1-3) → (1-2)  (R¹: alkyloxy, aryloxy, alkylthio, arylthio)

Scheme 5

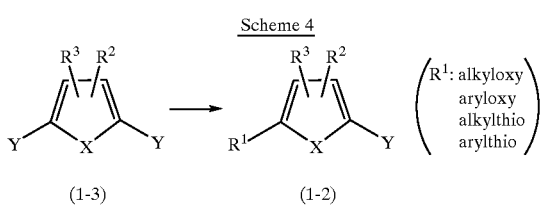

(1-4) → (I)  (R¹: alkyloxy, aryloxy, alkylthio, arylthio)

As apparent to one skilled in the art, the compound (I) can be also obtained from a reaction of the compound (1-1) wherein R is halo and the compound (1-2) wherein Y is replaced by an organometallic group such as $Me_3Sn-$, $Bu_3Sn-$, $Et_2B-$, $(HO)_2B-$ or zinc halide. The replacement of a halogen atom by the organometallic group can be carried out by the halogen-metal exchange, followed by a reaction of appropriate reagents such as trimethyltin chloride, tributyltin chloride, diethyl methoxyborane or trimethyl borate.

Unless indicated otherwise, the pressure of each of the above reactions is not critical. Generally, the reactions will be conducted at a pressure of about one to about three atmospheres, preferably at ambient pressure (about one atmosphere).

2. Synthesis of Pyridylfurans and Pyridylthiophenes by Paal-Knoll or Knorr's method The compounds of formula (I) can be prepared by using the method of Paal-Knoll or Knorr as shown in Scheme 6.

Scheme 6

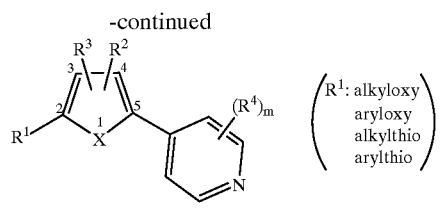

(2-1) →

(2-2)

(2-1) →

(2-3)

Pyridylfurans (2-2) can be prepared by the intramolecular cyclization of 1,4-dione (2-1) with acid catalyst such as $H_2SO_4$, $P_2O_5$, $ZnCl_2$, $Ac_2O$, $TiCl_4$, PPA, and the like, preferably PPA. Pyridylthiophenes (2-3) can be prepared by the reaction of 1,4-dione (2-1) with $P_2S_3$, $P_2S_5$, $H_2S$, and the like.

Unless indicated otherwise, the pressure of each of the above reactions is not critical. Generally, the reactions will be conducted at a pressure of about one to about three atmospheres, preferable at ambient pressure (about one atmosphere).

As the pyridylfuran and pyridylthiophene compounds of this invention may possess at least one asymmetric center, they are capable of occurring in various stereoisomeric forms or configurations. Hence, the compounds can exist in separated (+)- and (−)-optically active forms, as well as in racemic or (±)-mixtures thereof. The present invention includes all such forms within its scope. Individual isomers can be obtained by known methods, such as optically selective reaction or chromatographic separation in the preparation of the final product or its intermediate.

Insofar as the pyridylfuran and pyridylthiophene compounds of this invention are basic compounds, they are capable of forming a wide variety of different salts with various inorganic and organic acids.

The acids which are used to prepare the pharmaceutically acceptable acid addition salts of the aforementioned pyridylfuran and pyridylthiophene base compounds of this invention of formula (I) are those which form non-toxic acid addition salts, i.e., salts containing pharmaceutically acceptable anions, such as chloride, bromide, iodide, nitrate, sulfate or bisulfate, phosphate or acid phosphate, acetate, lactate, citrate or acid citrate, tartrate or bi-tartrate, succinate, maleate, fumarate. gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate))salts among others.

The pharmaceutically acceptable salts of the present invention also include alkali or alkaline earth metal salts such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Quaternary salts obtained from compounds of the invention and $C_{1-4}$ alkyl halide are also included. The other pharmaceutically acceptable salts which can be used in the present invention are described in *J. Pharmaceutical Sciences*, 1977, 66, 1–19. These salts can be prepared by conventional procedures.

Method of Treatment

The compounds (I) of this invention prepared as mentioned above inhibit inflammatory stimuli-induced cytokine production such as tumor necrosis factor alpha (TNF-α) and interleukin-1β (IL-1β), and are useful in the treatment or alleviation of various cytokine-mediated diseases such as asthma, arthritis, inflammatory bowel disease (IBD), sepsis, septic shock, rhinitis, inflammation of organs (e.g. hepatitis), AIDS and various inflammatory diseases. Furthermore, the compounds of this invention inhibit inflammatory stimuli-induced synthesis of proteins that regulate adhesion of leukocytes to other leukocytes and to other cell types and have potential use in the treatment of inflammatory and immune disorders such as arthritis and IBD; cardiovascular diseases, psoriasis and transplant rejection.

The pyridylfuran and pyridylthiophene compounds of formula (I) of this invention, or their pharmaceutically effective salts, can be administered via either the oral, parenteral (e.g., intravenous, intramuscula or subcutaneous) or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. For example, a dosage level that is in the range of from 0.06 mg to 2 mg per kg of body weight per day is most desirably employed for the treatment of inflammation. The compound of the invention can be administered either in a single daily dose or divided doses (e.g., 2–4 times/day).

The compounds (I) of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The ability of the compounds of the formula (I) to inhibit TNFα biosynthesis and CAMs expression may be demonstrated in vitro by the following procedures.

Method for Determining the Inhibition of TNFα Biosynthesis and CAM Expression

1. Cells and Cell Culture:

L929 cells are grown in minimum essential medium (MEM) (Gibco BRL NY) supplemented with 10% FCS, 50 U/mL penicillin and 50 μg/mL streptomycin. Human umbilical vein endothelial cells (HUVECs) are obtained from Morinaga and grown in endothelial growth medium (E-GM UV, Kurabou, Japan) supplemented with 10% fetal calf serum (FCS, Biowhitakker, Walkersville, Md.), 10 ng/mL EGF, 1 μg/mL hydrocortisone, and 1:100 dilution of bovine brain extract (Kurabou, Japan) in 5% $CO_2$ at 37° C. Cells of a human promyelocytic cell line, HL-60, are grown in RPMI-1640 (Nissui Seiyaku, Tokyo, Japan) supplemented with 10% FCS plus penicillin (50 U/mL) and streptomycin (50 μg/mL).

The ability of the compounds of the formula (I) to inhibit TNFα biosynthesis may be demonstrated in vitro by the following procedure 2.

2. TNFα production:

Human peripheral blood mononuclear cells (HPBMNC) are isolated from heparinized human whole blood by Ficoll-Paque (Pharmacia, Sweden) density centrifugation, washed with Ca-Mg free phosphate-buffered saline (PBS, Nissui Seiyaku, Tokyo, Japan), suspended in RPMI 1640 containing 10% FCS and plated into 48 well plates (Falcon, Becton Dickinson, N.J.) at $2 \times 10^6$ cells/well. Monocytes (HMo) are allowed to adhere to the plate by incubating at 37° C. for 1 hour, then the supernatant is aspirated and refilled with fresh RPMI-1640 medium containing 1% FCS.

Test compounds are prepared as 100 mM dimethyl sulfoxide (DMSO) stock solutions and diluted with media to obtain final testing concentrations. HMo are incubated at 37° C. for 4 hours in the presence of LPS (*E. coli.* 055:B5, Difco, Mich.) (10 μg/mL) with the test compounds in dose ranges of about 0.1 μM~100 μM. The assay is run in a volume of 200 μL/well. Supernatants are subjected to quantitation of TNFα by an L929 cell cytotoxicity assay or by TNF enzyme immuno assay.

L929 cell cytotoxicity assay: On the day of the experiment, L929 cells are detached by trypsin treatment, washed with MEM and resuspended with 1% FCS-containing MEM. L929 cells ($8 \times 10^5$ cells/well) in a volume of 50 μL are plated into flat-bottomed 96 well plates (Corning, N.Y.) and incubated with 50 μL of serially diluted supernatants in the presence of a final concentration of 0.5 μg/mL of actinomycin D (Wako, Japan) at 37° C. in 5% $CO_2$ for 18 hours. After incubation, the culture medium is removed and viable cells are stained with 0.2% crystal violet dissolved in 20% ethanol. The cells are washed with tap water and air-dried at room temperature. Resulting crystal violet is dissolved in 100 μl of 100% methanol and the optical density is determined at 595 nm on a BIO-RAD plate reader (Richmond, Calif.). The concentration of TNFα is determined using human recombinant TNFα (Wako, Japan) as a standard.

TNFα enzyme immuno assay: TNFα levels in culture supernatants are determined by the *TiterZyme* TNFα EIA kit (PerSeptive Biosystems, Mass.), following the instruction manual. Briefly, diluted sample are added onto the 96 well plates precoated with anti-TNFα monoclonal antibody and incubated at 37° C. for 2 hours. After washing wells, anti-TNF polyclonal antibody is added, followed by goat anti-rabbit horseradish peroxidase conjugate. 3,3',5,5'-Tetramethylbenzidine (TMB) is used as the substrate. The reaction is stopped by the addition of 1N-HCl, and the optical density is determined at 450 nm on a BIO-RAD plate reader.

Percent inhibition is determined by comparing the absorbance of vehicle treated cells with drug treated cells. Linear regression analysis of the means of the inhibition values are used to determine the $IC_{50}$.

Some compounds prepared in the Working Examples as described below were tested by this method, and showed an $IC_{50}$ value of 100 nM to 10 μM with respect to inhibition of TNFα biosynthesis.

The ability of the compounds of the formula (I) to inhibit CAM 15 expression may be demonstrated in vitro by the following procedures 3 and 4.

3. Cell ELISA:

Test compounds are diluted with media to obtain final testing concentrations. HUVECs ($1.2 \times 10^4$/well) grown in flat-bottomed, 96 well culture plates (Corning, N.Y.) are stimulated with human TNFα (3 U/mL, Wako, Tokyo, Japan) in the presence or absence of test compounds. Cells are incubated for 6 hours, then washed in PBS, fixed in 4% paraformaldehyde for 15 minutes, washed and stored for 1–3 days at 4° C. in PBS.

Adhesion molecules are detected using ELISA. Cells are incubated with a primary murine antibody to either ICAM-1 (0.5 μg/mL) (BBA#3, R&D Systems) or E-selectin (0.5 μg/mL) (BBA#1, R&D Systems) at room temperature for 2 hours. Anti-mouse Ig, peroxidase-linked species-specific F(ab')$_2$ fragment (from sheep) (Amersham; 1:2500 dilution) is used as the second antibody, followed by the addition of peroxidase substrate, o-phenylenediamine (2.2 mM) and hydrogen peroxide (3.9 mM). The absorbance of each well is read with a Bio-Rad plate reader at 490 nm, and the background at 655 nm is subtracted. The absorbance of nonstimulated HUVECs is subtracted from the absorbance values of TNFα-stimulated cells. Percent inhibition is determined by comparing the absorbance values of vehicle treated cells with that of drug treated cells. Linear regression analysis of the means of the inhibition values are used to determine the $IC_{50}$.

Some compounds prepared in the Working Examples as described below were tested by this method, and showed an $IC_{50}$ value of 100 nM to 10 μM with respect to inhibition of the CAM expression.

4. Cell Adhesion Assay:

HL-60 cells are induced to differentiate into granulocyte-like cells by 1.25% DMSO in RPMI-1640 supplemented with 10% heat-inactivated FCS for 5–6 days. The cells are then incubated with 300 μM of a fluorescent dye, 5(6)-carboxyl fluorescein diacetate, for 30 minutes at 37° C. and washed three times with Hank's solution. HUVECs ($1.2 \times 10^4$/well) grown in 96 well plates are simultaneously treated with the test compounds which are diluted with media to obtain final testing concentrations and 30 U/mL TNFα for 6 hours. Labeled cells ($5 \times 10^5$/well) are added to TNFα-stimulated HUVECs in a final volume of 0.1 mL, gently washed four times with warm Hank's solution, and remaining cells are lysed with 1% Nonidet P-40. The number of adherent cells are determined by measuring the fluorescence intensity using a Fluoroscan II (excitation at 485 nm and emission at 538 nm). Percent inhibition is determined by comparing the fluorescence intensity of vehicle treated cells with that of drug treated cells. Linear regression analysis of the means of the inhibition values are used to determine the $IC_{50}$s.

Some compounds prepared in the Working Examples as described below were tested by this method, and showed an $IC_{50}$ value of 100 nM to 10 μM with respect to inhibition of the adhesion of HL-60 to HUVECs stimulated by TNFα.

The following representative examples are illustrative of the invention and are not intended as a restriction on the scope of the invention.

EXAMPLES

The present invention is illustrated by the following examples. However, it should be understood that the invention is not limited to the specific details of these examples. Melting points were taken with a Buchi micro melting point apparatus and uncorrected. Mass spectra were recorded on a JEOL JMS-AM120. Infrared Ray absorption spectra (IR) were measured by a Shimazu infrared spectrometer (IR-470). $^1H$ and $^{13}C$ nuclear magnetic resonance spectra (NMR) were measured in $CDCl_3$ by a JEOL NMR spectrometer (JNNI-GX270, 270 MHz) unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad. Coupling constants (J) are recorded in hertz. The following abbreviations are used: MeOH for methanol, EtOH for ethanol, DMSO for dimethylsulfoxide, DMF for N,N-dimethylformamide, THF for tetrahydrofuran, HCl for hydrogen chloride or $CH_2Cl_2$ for dichloromethane, $MgSO_4$ for magnesium sulfate, $NaHCO_3$ for sodium bicarbonate.

Example 1

3-Acetyl-2,4-dimethyl-5-(4-pyridyl)furan

3-Acetyl-5-bromo-2,4-dimethylfuran (Step 1)

A mixture of 3-acetyl-2,4-dimethylfuran (commercially available from Aldrich Chemical Co., Inc., 1 g, 7.24 mmol), N-bromosuccinimide (NBS; 1.3 g, 7.3 mmol), and 2,2'-azobisisobutyronitrile (AIBN; 3 mg) in benzene (10 mL) was heated at reflux temperature for one hour. After cooling, water (50 mL) was added to the mixture. The whole was extracted with benzene (50 mL), the organic layer washed with water, brine, dried over $MgSO_4$, and concentrated in vacuo. Chromatographic purification of the residue eluting with ethyl acetate-hexane (1:10) provided the subtitle compound (1.38 g, 88% yield) as a pale yellow oil.

$^1H$-NMR ($CDCl_3$) δ 2.55 (s, 3H), 2.43 (s, 3H), 2.14 (s, 3H).

3-Acetyl-2,4-dimethyl-5-(4-pyridyl)furan (Step 2)

To a stirred solution of 3-acetyl-5-bromo-2,4-dimethylfuran (0.8 g, 3.69 mmol) in dimethoxyethane (DME; 11 mL) was added water (4 mL), $NaHCO_3$ (0.93 g, 11 mmol), 4-pyridineboronic acid [prepared according to the method of Fischer F. C. et al., *J. Red. Trav. Chim. Pays-Bays*, 1965, 84, 439.] (0.5 g, 4.06 mmol) and bis(triphenylphosphine)palladium(II)chloride (0.26 g, 0.37 mmol) at room temperature under nitrogen. The mixture was heated at reflux temperature for 8 hours, and cooled down to room temperature. 4-Pyridineboronic acid (0.5 g, 4.07 mmol) and bis(triphenylphosphine)palladium(II)chloride (1.48 g, 2.11 mmol) were additionally added to the reaction mixture, and heated at reflux temperature for 3.5 hours. After cooling, the reaction mixture was filtered through celite pad. The filtrate was diluted with ethyl acetate (50 mL), and the whole was washed with water (30 mL). The aqueous layer was extracted with ethyl acetate (30 mL), and the combined organic layers were washed with brine (50 mL), dried over $MgSO_4$, and concentrated in vacuo. The resulting residue was purified by flash chromatography eluting with ethyl acetate-hexane (5:1) to give the title compound (0.25 g, 31% yield).

mp: 65–66.5° C.

$^1H$—NMR ($CDCl_3$) δ 8.63 (d, J=6.2 Hz, 2H), 7.48 (d, J=6.2 Hz, 2H). 2.65 (s, 3H), 2.50 (s, 3H), 2.47 (s, 3H).

Anal. Calcd. for $C_{13}H_{13}NO_2$: C, 72.54; H, 6.09; N, 6.51. Found: C, 72.58; H, 5.98; N, 6.15.

Example 2

3-Methyl-4-oxo-2-(4-pyridyl)-4,5,6,7-tetrahydrobenzofuran

3-Methyl-4-oxo-4,5,6,7-tetrahydrobenzofuran (step 1)

A mixture of 1,3-cyclohexanedione (3.36 g, 30 mmol), acetol (hydroxyacetone; 2.22 g, 30 mmol), and zinc chloride (4.09 g, 30 mmol) in ethanol (10 mL) was heated at reflux temperature for 3 hours. After cooling, the mixture was dissolved in ethyl acetate (100 mL). The whole was washed with water (100 mL), brine (100 mL), dried over $MgSO_4$, and concentrated in vacuo. The residue was purified by flash chlomatography eluting with ethyl acetate - hexane (1:10) to give the subtitle compound (1.69 g, 38% yield).

$^1H$—NMR ($CDCl_3$) δ 7.06 (d, J=0.8 Hz, 1H), 2.83 (t, J=6.2 Hz, 2H), 2.46 (dd, J=6.6 Hz, 6.2 Hz, 2H), 2.19 (d, J=0.8 Hz, 3H), 2.15 (t, J=6.6 Hz, 2H).

2-Bromo-3-methyl-4-oxo-4,5,6,7-tetrahydrobenzofuran (step2)

The subtitle compound was prepared according to the procedure of example 1 using 3-methyl-4-oxo-4,5,6,7-tetrahydrobenzofuran instead of 3-acetyl-2,4-dimethylfuran in step 1.

$^1H$—NMR ($CDCl_3$) δ 2.83 (t, J=6.6 Hz, 2H), 2.47 (t, J=6.6 Hz, 2H), 2.20-2.12 (m, 2H), 2.15 (s, 3H).

3-Methyl-4-oxo-2-(4-pyridyl)-4,5,6,7-tetrahydrobenzofuran (step 3)

The title compound was prepared according to the procedure of example 1using 2-bromo-3-methyl-4-oxo-4,5,6,7-tetrahydrobenzofuran instead of 3-acetyl-5-bromo-2,4-dimethylfuran in step 2.

mp: 136–138° C.

$^1H$—NMR ($CDCl_3$) δ 8.63 (dd, J=4.7 Hz, 1.8 Hz, 2H), 7.50 (dd, J=4.7 Hz, 1.8 Hz, 2H), 2.94 (t, J=6.2 Hz, 2H), 2.56 (s, 3H), 2.55-2.50 (m, 2H), 2.26-2.16 (m, 2H).

Anal. Calcd. for $C_{14}H_{13}NO_2$: C, 73.99; H, 5.77; N, 6.16. Found: C, 73.80; H, 5.75; N, 6.07.

Example 3

3-Acetyl-4-methyl-2-phenyl-5-(4-pyridyl)furan

N,O-dimethyl-4-methyl-2-phenylfuran-3-hydroxamate

A mixture of 2-phenyl-4-methylfuran-3-carboxylic acid (Hanson et al, *J. Chem. Soc.*, 1965, 5986) (1.01 g. 5 mmol), N,O-dimethylhydroxylamine hydrochloride (0.54 g, 5.5 mmol), 1-ethyl-3-(3-dimethylaminopropyl)carbodiimide (1.05 g, 5.5 mmol), and triethylamine (0.56 g, 5.5 mmol) in $CH_2Cl_2$ (20 mL) was stirred overnight. $CH_2Cl_2$ (100 mL) was added to the mixture, and the whole was washed with water, brine, dried over $MgSO_4$, and concentrated in vacuo. Chromatographic purification of the residue eluting with ethyl acetate-hexane (3:1) provided the subtitle compound (0.57 g, 47% yield).

$^1H$—NMR ($CDCl_3$) δ 7.67-7.62 (m, 2H), 7.41-7.23 (m, 4H), 3.47 (br. s, 3H), 3.31 (br. s, 3H), 2.05 (s, 3H).

3-acetyl-4-methyl-2-phenylfuran

To a stirred solution of N,O-dimethyl-4-methyl-2-phenylfuran-3-hydroxamate (0.57 g, 2.33 mmol) in THF (12 mL) was added 1M solution of methylmagnesium bromide in THF (2.4 mL, 2.4 mmol) at room temperature. The mixture was heated at reflux temperature for 3 hours. After cooling, 2N HCl solution was added, and the whole was extracted with ethyl acetate (30 mL×2). The combined organic layers were washed with water, brine, dried over $MgSO_4$, and concentrated in vacuo. Chromatographic purification of the residue eluting with hexane-ethyl acetate (10:1) provide the subtitle compound (0.15 g, 32% yield).

$^1$H—NMR (CDCl$_3$) δ 7.58-7.53 (m, 2H), 7.47-7.42 (m, 2H), 7.27-7.22 (m, 2H), 2.25 (s, 3H), 2.18 (d,J=1.1 Hz, 3H).

3-Acetyl-5-bromo-4-methyl-2-phenylfuran

The subtitle compound was prepared according to the procedure of example 1 using 3-acetyl-4-methyl-2-phenylfuran instead of 3-acetyl-2,4-dimethylfuran in step 1.

3-Acetyl-4-methyl-2-phenyl-5-(4-pyridyl)furan

The title compound was prepared according to the procedure of example 1 using 3-acetyl-5-bromo-4-methyl-2-phenylfuran instead of 3-acetyl-5-bromo-2,4-dimethylfuran in step 2.

mp: 108–110° C.

$^1$H—NMR (CDCl$_3$) δ 8.65 (dd, J=4.8 Hz, 1.8 Hz, 2H), 7.64-7.59 (m, 2H), 7.57 (dd, J=4.8 Hz, 1.8 Hz, 2H), 7.51-7.47 (m, 3H), 2.45 (s, 3H), 2.31 (s, 3H).

Anal. Calcd. for C$_{18}$H$_{15}$NO$_2$: C, 77.96; H, 5.45; N, 5.05. Found: C, 77.82; H, 5.41; N, 5.00.

Example 4 and 5

3-Acetoamino-2,4-dimethyl-5-(4-pyridyl)furan and 2,4-dimethyl-3-methylaminocarbonyl-5-(4-pyridyl)furan 2-4-Dimethyl-3-(1-hydroxylminoethyl)-5-(4-pyridyl)furan To a stirred solution of 3-acetyl-2,4-dimethyl-5-(4-pyridyl)furan (0.5 g, 2.33 mM) in EtOH (10 mL) and pryidine (2 mL) was added hydroxylamine hydrochloride (0.2 g, 2.79 mM) at room temperature. After stirring overnight, volatiles were removed by evaporation. Ethyl acetate (100 mL) and water (70 mL) were added, and partitioned. The organic layer was washed with water, brine, dried over MgSO$_4$, and concentrated in vacuo. The resulting solid was triturated to give the subtitle compound (0.45 g, 84% yield).

$^1$H—NMR (CDCl$_3$) δ 9.70 (br.s, 1H), 8.60-8.57 (m, 2H), 7.50-7.47 (m, 2H), 2.41 (s, 3H), 2.30 (s, 3H), 2.21 (s, 3H).

3-Acetoamino-2,4-dimethyl-5-(4-pyridyl)furan and 2,4-dimethyl-3-methylaminocarbonyl-5-(4-pyridyl)furan To a stirred solution of 2,4-dimethyl-3-(1-hydroxylminoethyl)-5-(4-pyridyl)furan (0.23 g, 1 mM) in Et$_2$O (10 mL) was added phosphorus pentachloride (0.22 g, 1 mM) at room temperature, and the mixture was stirred overnight. The mixture was poured into saturated NaHCO$_3$ solution (50 mL), and partitioned. The aqueous layer was extracted with ethyl acetate (30 mL×2), the combined organic layers washed with water, brine, dried over MgSO$_4$, and concentrated in vacuo. The resulting residue was purified by flash chromatography eluting with CH$_2$Cl$_2$-EtOH to give 2,4-dimethyl-3-methylaminocarbonyl-5-(4-pyridyl)furan as the less polar product (0.04 g, 17% yield) and 3-acetoamino-2,4-dimethyl-5-(4-pyridyl)furan as the more polar product (0.15 g, 65% yield).

Less polar product;

mp: 195–197° C.

$^1$H—NMR (CDCl$_3$) δ 8.62-8.58 (m, 2H), 7.48-7.44 (m, 2H), 5.68 (br.s, 1H), 3.00 (d, J=4.8 Hz, 3H), 2.53 (s, 3H), 2.40 (s, 3H).

MS (FAB); 231 (M+H)$^+$

Anal. Calcd. for C$_{13}$H$_{14}$N$_2$O$_2$ 0.15H$_2$O: C, 67.02; H, 6.19; N, 12.02. Found: C, 67.31; H, 6.29; N, 11.62.

More polar product;

mp: 214–216° C.

$^1$H—NMR (CDCl$_3$) δ 8.57-8.53 (m, 2H), 7.48-7.43 (m, 2H), 6.77 (br.s, 1H), 2.29 (s, 3H), 2.21 (s, 3H), 2.17 (s, 3H).

MS (FAB); 231 (M+H)$^+$

Anal. Calcd. for C$_{13}$H$_{14}$N$_2$O$_2$: C, 67.81; H, 6.13; N, 12.17. Found: C, 67.98; H, 6.21; N, 12.11.

Example 6

4-Oxo-2-(4-pyridyl)-3,5,5-trimethyl-4,5,6,7-tetrahydrobenzofuran

4-Oxo-3,5,5-trimethyl-4,5,6,7-tetrahydrobenzofuran

The subtitle compound was prepared according to the procedure of example 2 using 4,4-dimethyl-1,3-cyclohexanedione instead of 1,3-cyclohexanedione in step 1.

$^1$H—NMR (CDCl$_3$) δ 7.07 (s, 1H), 2.84 (t, J=6.2 Hz, 2H), 2.19 (d, J=1.4 Hz, 3H), 1.98 (t, J=6.2 Hz, 2H), 1.17 (s, 6H).

2-Bromo-4-oxo-3,5,5-trimethyl-4,5,6,7-tetrahydrobenzofuran

The subtitle compound was prepared according to the procedure of example 2 using 4-oxo-3,5,5-trimethyl-4,5,6,7-tetrahydrobenzofuran instead of 3-methyl-4-oxo-4,5,6,7-tetrahydrobenzofuran in step 2.

4-Oxo-2-(4-pyridyl)-3,5,5-trimethyl-4,5,6,7-tetrahydrobenzofuran

The title compound was prepared according to the procedure of example 1 using 2-bromo-4-oxo-3,5,5-trimethyl-4,5,6,7-tetrahydrobenzofuran instead of 3-acetyl-5-bromo-2,4-dimethylfuran in step 2.

mp: 133–134° C.

$^1$H—NMR (CDCl$_3$) δ 8.64-8.61 (m, 2H), 7.52-7.48 (m, 2H), 2.95 (t, J=6.3 Hz, 2H), 2.55 (s, 3H), 2.03 (t, J=6.3 Hz, 2H), 1.21 (s, 6H).

MS (ESI) m/z: 256 (M+H)$^+$

Anal. Calcd. for C$_{16}$H$_{17}$NO$_2$: C, 75.27; H, 6.71; N, 5.49. Found: C, 75.06; H, 6.61; N, 5.89.

Example 7

4-Oxo-2-(4-pyridyl)-3,7,7-trimethyl-4,5,6,7-tetrahydrobenzofuran

4-Oxo-3,7,7-trimethyl-4,5,6,7-tetrahydrobenzofuran (step 1)

The subtitle compound was prepared according to the procedure of example 2 using 4,4-dimethyl-1,3-cyclohexanedione instead of 1,3-cyclohexanedione in step1.

$^1$H—NMR (CDCl$_3$) δ 7.06 (d, J=1.5 Hz, 1H), 2.54 (t, J=6.6 Hz, 2H), 2.18 (d, J=1.5 Hz, 3H), 2.00-1.94 (m, 2H), 1.35 (s, 6H).

2-Bromo-4-oxo-3,7,7-trimethyl-4,5,6,7-tetrahydrobenzofuran (step 2)

The subtitle compound was prepared according to the procedure of example 2 using 4-oxo-3,7,7-trimethyl-4,5,6,7-tetrahydrobenzofuran instead of 3-methyl-4-oxo-4,5,6,7-tetrahydrobenzofuran in step2.

4-Oxo-2-(4-pyridyl)-3,7,7-trimethyl-4,5,6,7-tetrahydrobenzofuran

The title compound was prepared according to the procedure of example 1 using 2-bromo-4-oxo-3,7,7-trimethyl-4,5,6,7-tetrahydrobenzofuran instead of 3-acetyl-5-bromo-2,4-dimethylfuran in step 2.

mp: 138–140° C.

$^1$H—NMR (CDCl$_3$) δ 8.63 (d, J=6.2 Hz, 1H), 7.50 (d, J=6.2 Hz, 2H), 2.59 (t, J=6.6 Hz, 2H), 2.55 (s, 3H), 2.02 (t, J=6.6 Hz. 2H), 1.44 (s, 6H)

MS (ESI) ra/z: 256 (M+H)$^+$

Anal. Calcd. for C$_{16}$H$_{17}$NO$_2$: C, 75.27; H, 6.71; N, 5.49, Found: C, 75.05; H. 6.59; N, 5.66.

Example 8

3-Methyl-4-oxo-2-(4-pyridyl)cyclohepteno(b)furan

3-Methyl-4-oxo-cyclohepteno(b)furan

The subtitle compound was prepared according to the procedure of example 2 using 1,3-cycloheptanedione instead of 1,3-cyclohexanedione in step1.

$^1$H—NMR (CDCl$_3$) δ 7.01 (s, 1H), 2.96 (t, J=6.5 Hz, 2H), 2.72 (t, J=6.5 Hz, 2H), 2.16 (s, 3H), 1.96-1.86 (m, 4H).

2-Bromo-3-methyl-4-oxo-cyclohepteno(b)furan

The subtitle compound was prepared according to the procedure of example 2 using 3-methyl-4-oxo-cyclohepteno(b)furan instead of 3-methyl-4-oxo-4,5,6,7-tetrahydrobenzofuran in step2.

3-Methyl-4-oxo-2-(4-pyridyl)cyclohepteno(b)furan

The title compound was prepared according to the procedure of example 1 using 2-bromo-3-methyl-4-oxo-cyclohepteno(b)furan instead of 3-acetyl-5-bromo-2,4-dimethylfuran in step 2.

mp: 82–83° C.

$^1$H—NMR (CDCl$_3$) δ 8.62 (dd, J=4.7 Hz, 1.8 Hz, 2H), 7.49 (dd, J=4.7 Hz, 1.8 Hz, 2H), 3.10-3.05 (m, 2H), 2.79-2.72 (m, 2H), 2.48 (s, 31H), 2.09-1.95 (m, 4H).

MS (ESI) m/z: 242 (M+H)$^+$

Anal. Calcd. for $C_{15}H_{15}NO_2$: C, 74.67; H, 6.27; N, 5.80. Found: C, 74.54; H, 6.14; N, 5.97.

Example 9

3-Acetyl-2-isobutyl-4-methyl-5-(4-pyridyl)furan hydrochloride 3-acetyl-5-bromo-2-isobutyl-4-methylfuran The subtitle compound was prepared according to the procedure of example 2 using 3-acetyl-2-isobutyl-4-methylfuran instead of 3-methyl-4-oxo-4,5,6,7-tetrahydrobenzofuran in step2.

3-Acetyl-2-isobutyl-4-methyl-5-(4-pyridyl)furan hydrochloride

The title compound was prepared according to the procedure of example 1 using 3-acetyl-5-bromo-2-isobutyl-4-methylfuran instead of 3-acetyl-5-bromo-2,4-dimethylfuran in step 2.

mp: 171–174° C.

$^1$H—NMR (CDCl$_3$) δ 8.71 (br. s, 2H), 8.01 (br. s, 2H), 2.91 (d, J=7.3 Hz, 2H), 2.62 (s, 3H), 2.54 (s, 3H), 2.21-2.12 (m, 1H), 1.03 (d, J=6.6 Hz, 6H).

MS (ESI) m/z: 258 (M')

Anal. Calcd. for $C_{16}H_{20}NO_2Cl$ 0.1H$_2$O: C, 65.01; H, 6.89; N, 4.74, Found: C, 64.78; H, 7.16; N, 5.00.

Example 10

6,7-Dihydro-3,6-dimethyl-2-(4-pyridyl)-furo[3,2-c]pyran-4-one 6,7-Dihydro-3,6-dimethyl-furo[3,2-c]pyran-4-one The subtitle compound was prepared according to the procedure of example 2 using 5,6-dihydro-4-hydroxy-6-methyl-2H-pyran-2-one instead of 1,3-cyclohexanedione in step1.

$^1$H—NMR (CDCl$_3$) δ 7.14 (s, 1H), 4.80-4.67 (m, 1H), 2.97-2.77 (m, 2H), 2.20 (d, J=1.5 Hz, 3H), 1.54 (d, J=6.2 Hz, 3H).

2-Bromo-6,7-dihydro-3,6-dimethyl-furo[3,2-c]pyran-4-one

The subtitle compound was prepared according to the procedure of example 2 using 6,7-dihydro-3,6-dimethyl-furo[3,2-c]pyran-4-one instead of 3-methyl-4-oxo-4,5,6,7-tetrahydrobenzofuran in step2.

$^1$H—NMR (CDCl$_3$) δ 4.79-4.70 (m, 1H), 2.98-2.80 (m, 2H), 216 (s, 3H), 1.54 (d, J=6.2 Hz, 3H).

6,7-Dihydro-3,6-dimethyl-2-(4-pyridyl)-furo[3,2-c]pyran-4-one

The title compound was prepared according to the procedure of example 1 using 2-bromo-6,7-dihydro-3,6-dimethyl-furo[3,2-c]pyran-4-one instead of 3-acetyl-5-bromo-2,4-dimethylfuran in step 2.

mp: 157–160° C.

$^1$H—NMR (CDCl$_3$) δ 8.67-8.64 (m, 2H), 7.52-7.49 (m, 2H), 4.85-4.74 (m, 1H), 3.10-2.94 (m, 2H), 2.55 (s, 3H), 1.59 (d, J=6.2 Hz, 3H).

MS (ESI) m/z: 234 (M+H)$^+$

Anal. Calcd. for $C_{14}H_{13}NO_3$ 0.35H$_2$O: C, 67.38; H, 5.53; N, 5.61, Found: C, 67.33; H, 5.26; N, 5.31.

Example 11

3-Ethyl-7,7-dimethyl-4-oxo-2-(4-pyridyl)-4,5,6,7-tetrahydrobenzofuran

3-Ethyl-7,7-dimethyl-4-oxo-4,5,6,7-tetrahydrobenzofuran (step 1)

The subtitle compound was prepared according to the procedure of example 2 using 1-hydroxy-2-butanone instead of acetol and 4,4-dimethyl-1,3-cyclohexanedione instead of 1,3-cyclohexanedione in step1.

$^1$H—NMR (CDCl$_3$) δ 7.06 (s, 1H), 2.69-2.51 (m, 4H), 1.96 (t, J=6.6 Hz, 2H), 1.35 (s, 6H), 1.18 (t, J=7.7 Hz, 3H).

2-Bromo-3-ethyl-7,7-dimethyl-4-oxo-4,5,6,7-tetrahydrobenzofuran (step 2)

The subtitle compound was prepared according to the procedure of example 2 using 3-ethyl-7,7-dimethyl-4-oxo-4,5,6,7-tetrahydrobenzofuran instead of 3-methyl-4-oxo-4,5,6,7-tetrahydrobenzofuran in step2.

$^1$H—NMR (CDCl$_3$) δ 2.60-2.51 (m, 4H), 1.96 (t, J=7.0 Hz, 2H), 1.36 (s, 6H), 1.13 (t, J=7.7 Hz, 3H).

4-Oxo-2-(4-pyridyl)-3,7,7-trimethyl-4,5,6,7-tetrahydrobenzofuran (Step 3)

The title compound was prepared according to the procedure of example 1 using 2-bromo-3-ethyl-7,7-dimethyl-4-oxo-4,5,6,7-tetrahydrobenzofuran instead of 3-acetyl-5-bromo-2,4-dimethylfuran in step 2.

mp: 86–88° C.

$^1$H—NMR (CDCl$_3$) δ 8.64 (dd, J=4.8 and 1.8 Hz, 2H), 7.50 (dd, J=4.8 and 1.8 Hz, 2H), 2.96 (q, J=7.3 Hz, 2H), 2.59 (t, J=6.3 Hz, 2H), 2.02 (t, J=6.3 Hz, 2H), 1.44 (s, 6H), 1.29 (t, J=7.3 Hz, 3H).

MS (ESI) m/z: 270 (M+H)$^+$

Anal. Calcd. for $C_{17}H_{19}NO_2$: C, 75.81; H, 7.11; N, 5.20. Found: C, 75.87; H, 7.22; N, 5.15.

Example 12

7,7-Dimethyl-3-phenyl-4-oxo-2-(4-pyridyl)-4,5,6,7-tetrahydrobenzofuran 7,7-Dimethyl-3-phenyl-4-oxo-4,5,6,7-tetrahydrobenzofuran (step 1)

The subtitle compound was prepared according to the procedure of example 2 using hydroxyacetophenone instead of acetol and 4,4-dimethyl-1,3-cyclohexanedione instead of 1,3-cyclohexanedione in step1.

$^1$H—NMR (CDCl$_3$) δ 7.62-7.57 (m, 2H), 7.40-7.30 (m, 4H), 2.63-2.57 (m, 2H), 2.02 (t, J=6.6 Hz, 2H), 1.41 (s, 6H).

2-Bromo-7,7-dimethyl-3-phenyl-4-oxo-4,5,6,7-tetrahydrobenzofuran (step 2)

The subtitle compound was prepared according to the procedure of example 2 using 7,7-dimethyl-3-phenyl-4-oxo4,5,6,7-tetrahydrobenzofuran instead of 3-methyl-4-oxo-4,5,6,7-tetrahydrobenzofuran in step2.

$^1$H—NMR (CDCl$_3$) δ 7.49-7.35 (m, 5H), 2.58 (t, J=6.6 Hz, 2H), 2.02 (t, J=6.6 Hz, 2H), 1.43 (s, 6H).

7,7-Dimethyl-3-phenyl-4-oxo-2-(4-pyridyl)-4,5,6,7-tetrahydrobenzofuran (Step 3)

The title compound was prepared according to the procedure of example 1 using 2-bromo-7,7-dimethyl-3-phenyl-4-oxo-4,5,6,7-tetrahydrobenzofuran instead of 3-acetyl-5-bromo-2,4-dimethylfuran in step 2.

mp: 156–157° C.

$^1$H—NMR (CDCl$_3$) δ 8.45 (dd. J=4.8 and 1.8 Hz. 2H), 7.43-7.34 (m, 5H), 7.23 (dd, J=4.8 and 1.8 Hz, 2H), 2.59 (t, J=6.9 Hz, 21H), 2.05 (t, J=6.9 Hz, 2H), 1.51 (s, 6H).

MS (ESI) m/z: 318 (M+H)$^+$

Example 13
2-Acetyl-4-methyl-3,5-di(4-pyridyl)thiophene

The title compound was prepared according to the procedure of Example 15 using 2-acetyl-3,5-dibromo-4-methylthiophene instead of 3-acetyl-2,5-dichloro-4-methylthiophene.

mp: 117–118° C.

IR ν 1660, 1600, 1410, 1370, 1290, 820 cm$^{-1}$ $^1$H—NMR (CDCl$_3$) δ 8.66 (dd, J=4.4 Hz, 1.8 Hz, 2H), 8.49 (dd, J=4.4 Hz, 1.5 Hz, 2H), 7.09 (dd, J=4.4 Hz, 1.5 Hz, 2H), 7.05 (dd, J=4.4 Hz, 1.5 Hz, 2H), 2.62 (s, 31H), 2.39 (s, 31H)

Anal. Calcd. for C$_{17}$H$_{14}$N$_2$OS: C, 69.36; H, 4.79; N, 9.52. Found: C, 69.19; H, 4.86; N, 9.29.

Example 14
2-Acetyl-3-methyl-4,5-di(4-pyridyl)thiophene

The title compound was prepared according to the procedure of Example 15 using 2-acetyl-4,5-dibromo-3-methylthiophene (Steinkopf et al, *Justus Liebigs Ann. Chem.*, 1938, 536, 135) instead of 3-acetyl-2,5-dichloro-4-methylthiophene.

mp: 140–142° C.

IR ν 1640, 1600, 1590, 1400, 1380, 1360, 1290, 820 cm$^{-1}$ $^1$H—NMR (CDCl$_3$) δ 8.76 (dd, J=4.4 Hz, 1.5 Hz, 2H), 8.72 (dd, J=4.4 Hz, 1.8 Hz, 2H), 7.41 (dd, J=4.4 Hz, 1.8 Hz, 2H), 7.23 (dd, J=4.4 Hz, 1.5 Hz, 2H), 2.15 (s, 3H), 2.03 (s, 3H)

Anal. Calcd. for C$_{17}$H$_{14}$N$_2$OS 0.2H$_2$O: C, 68.52; H, 4.87; N, 9.40, Found: C, 68.91; H, 4.65; N, 9.40.

Example 15
3-Acetyl-4-methyl-2,5-di(4-pyridyl)thiophene

3-Acetyl-2,5-dichloro4-methylthiophene was prepared according the method of Eric C. Bigham, U.S. Pat. No. 4,110,342 (1978). To a stirred solution of 3-acetyl-2,5-dichloro-4-methylthiophene (593 mg, 2.84 mmol) in DME (15 mL) were added 4-pyridineboronic acid (0.87 g, 7.09 mmol), water (5 mL), sodium bicarbonate (1.76 g 20.9 mmol) and bis(triphenylphosphine)-palladium(II)chloride (0.2 g, 0.28 mmol) at room temperature under nitrogen. The mixture was heated at reflux temperature for 8 hours. After cooling, 4-pyridineboronic acid (0.3 g, 2.44 mmol), sodium bicarbonate (0.6 g, 7.14 mmol) and bis(triphenylphosphine)-palladium(II)chloride (0.1 g, 0.14 mmol) were added to the reaction mixture. The mixture was heated at reflux temperature for additional 3 hours. After cooling, the reaction mixture was filtered through celite pad. The filtrate was extracted with ethyl acetate (100 mL×2), and the combined organic layers were washed with brine, dried over MgSO$_4$, and concentrated in vacuo. The resulting residue was purified by flash chromatography eluting with hexane-ethyl acetate (1:2) to provide the title product as a solid. Recrystallized from ethyl acetate gave the title product (468 mg, 56% yield).

mp: 137–138° C.

IR ν 1690, 1590, 1410, 1370, 1280, 990, 820, 720 cm$^{-1}$ $^1$H—NMR (CDCl$_3$) δ 8.72-8.66 (m, 4H), 7.40-7.32 (m, 4H), 2.32 (s, 3H), 2.25 (s, 3H)

Anal. Calcd. for C$_{17}$H$_{14}$N$_2$OS: C, 69.36; H, 4.79; N, 9.52. Found: C, 69.22; H, 4.68; N, 9.21.

Example 16
4-Oxo-2-(4-pyridyl)-4,5,6,7-tetrahydro-benzo(b)thiophene

The title compound was prepared according to the procedure of Example 15 using 2-bromo-4-oxo-4,5,6,7-tetrahydrobenzothiophene (Pinna, G. A. et al, *Eur. J. Med. Chem.*, 1994, 29, 447–454) instead of 3-acetyl-2,5-dichloro-4-methylthiophene.

mp: 156–158° C. (Recryst. fromEthyl Acetate-Hexane)

IR (KBr) ν 1660, 1590, 1420, 1400, 1240, 1190, 830, 820 cm$^{-1}$ $^1$H—NMR (CDCl$_3$) δ 8.61-8.59 (m, 2H), 7.79 (s, 1H), 7.44-7.42 (m, 2H), 3.08 (dd, J=5.9 and 6.2 Hz, 2H), 2.60 (dd, J=5.5 and 7.3 Hz, 2H), 2.31-2.22 (m, 2H).

Anal. Calcd for C$_{13}$H$_{11}$NOS: C, 68.10; H, 4.84; N, 6.11. Found: C, 67.89; H, 4.68; N, 5.83.

MS (El) m/z 229 (M$^+$).

Example 17
3-Acetyl-5-chloro-4-methyl-2-(4-pyridyl)thiophene

The title compound was obtained as a byproduct in Example 15. Alternatively the title compound was prepared according to the method of Example 15 using 1 equivalent of 4-pyridineboronic acid instead of 2 to 3 equivalent of 4-pyridineboronic acid.

mp: 60–61° C. (Recryst. from water- methanol)

IR (KBr) ν 1690, 1600, 1450, 1410, 1270, 1180, 820 cm$^{-1}$ $^1$H—NMR (CDCl$_3$) δ 8.67-8.65 (m, 2H), 7.28-7.26 (m, 2H), 2.21 (S, 3H), 2.18 (s, 3H).

Anal. Calcd for C$_{12}$H$_{10}$ClNOS; C, 57.26; H, 4.00; N, 5.56. Found: C, 57.40; H, 3.90; N, 5.20.

MS (El) m/z, 251 (M$^+$).

Example 18
3-Acetyl-2,4-dimethyl-5-(4-pyridyl)thiophene

2-Chloro-3,5-dimethylthiophene

A mixture of 2,4-dimethylthiophene (commercially available from Avocado Research Chemicals Ltd., 2.5 g, 22.3 mmol) and sulfulyl chloride (1.8 mL, 22.3 mmol) was heated at reflux temperature for 2 hours under nitrogen. After cooling, the mixture was purified by distillation (0.25 mmHg at 29° C.) to provide the title compound ( 0.90 g, 28% yield).

$^1$H—NMR (CDCl$_3$) δ 6.43 (d, J=0.7 Hz, 1H), 2.36 (d, J=1.1 Hz, 3H), 2.10 (s, 3H).

3-Acetyl-5-chloro-2,4-dimethylthiophene

To a stirred solution of 2-chloro-3,5-dimethylthiophene ( 0.9 g, 6.18 mmol) in petroleum ether (5 mL) was added acetyl chloride (0.9 mL, 12.4 mmol) and aluminum chloride (0.99 g, 7.42 mmol) at room temperature under nitrogen, and the mixture stirred for 1 day. The reaction mixture was poured into ice water (50 mL) and the whole was extracted with diethyl ether (70 mL×2). The combined organic layers were washed with brine, dried over MgSO$_4$, and concentrated in vacuo. The residue was purified by flash chromatography eluting with hexane-ethyl acetate (20:1) to provide the title product (0.85 g, 73% yield).

$^1$H—NMR (CDCl$_3$) δ 2.53 (s, 3H), 2.47 (s, 3H), 2.25 (s, 3H).

3-Acetyl-2,4-dimethyl-5-(4-pyridyl)thiophene

The title compound was prepared according to the procedure of Example 15 using 3-acetyl-5-chloro-2,4-dimethylthiophene instead of 3-acetyl-2,5-dichloro-4-methylthiophene.

mp: 80–81° C.

$^1$H—NMR (CDCl$_3$) δ 8.64 (dd, J=4.8 Hz, 1.8 Hz, 2H), 7.31 (dd, J=4.8 Hz, 1.8 Hz. 2H), 2.62 (s, 3H), 2.54 (s, 3H), 2.36 (s, 3H).

IR ν 1660, 1600, 1405, 1380, 1375, 1215, 820 cm$^{-1}$

Anal. Calcd. for C$_{13}$H$_{13}$NOS: C, 67.50 H, 5.66; N, 6.06, S, 13.86. Found: C, 67.92; H. 5.70; N, 6.46, S, 13.53.

Example 19

3-Acetyl-4-methyl-2-phenyl-5-(4-pyridyl)thiophene

3-Acetyl-5-chloro-4-methyl-2-phenylthiophene (step 1)

To a stirred solution of 3-acetyl-2,5-dichloro-4-methylthiophene (0.98 g, 4.69 mmol) in DME (15mL) were added benzeneboronic acid (0.69 g, 7.09 mmol), a saturated aqueous solution of sodium bicarbonate (5 mL) and bis(triphenylphosphine)palladium(II)chloride (0.39 g, 0.56 mmol) at room temperature under nitrogen. The mixture was heated at reflux temperature for 3 hours. The whole was extracted with diethyl ether (50 mL×2), and the combined organic layers were washed with brine, dried over $MgSO_4$, and concentrated in vacuo. The residue was purified by flash chromatography eluting with hexane-ethyl acetate (10:1) to provide the title product (916 mg, 78% yield).

$^1$H—NMR ($CDCl_3$) δ 7.45-7.33 (m, 5H), 2.22 (s, 3H), 2.05 (s, 3H)

3-Acetyl-4-methyl-2-phenyl-5-(4-pyridyl)thiophene (step 2)

The title compound was prepared according to the procedure of Example 15 using 3-acetyl-5-chloro-4-methyl-2-phenylthiophene instead of 3-acetyl-2,5-dichloro-4-methylthiophene.

mp: 111–112° C.

$^1$H—NMR (DMSO-4) δ 8.68 (d, J=4.8 Hz, 2H), 7.55-7.43 (m, 7H), 2.28 (s, 3H), 2.14 (s, 3H).

IR ν 1665, 1590, 1370, 820, 760, 700 $cm^{-1}$

Anal. Calcd. for $C_{18}H_{15}NOS$: C. 73.69 H, 5.15; N, 4.77, S, 10.93. Found: C, 73.56; H, 5.16; N, 4.79, S, 10.72.

Example 20

3-Methyl-4-oxo-2-(4-pyridyl)-4,5,6,7-tetrahydrobenzothiophene

A mixture of 4-(3-methylthiphen-2-yl)-4-oxobutylic acid and 4-(4-methylthiphen-2-yl)-4-oxobutylic acid A mixture of 4-(3-methylthiphen-2-yl)butylic acid and 4-(4-methylthiphen-2-yl)butylic acid was prepared according to the modified method of N. B. Chapman, *J. Chem. Soc. Perkin. Trans. I*, 3011 (1972). Aluminum chloride (37.4 g, 280 mmol) was added in portions over 20 minutes to a stirred suspension of succinic anhydride (14.0 g, 140 mmol) in $CH_2Cl_2$ (400 mL) at 20° C., and the mixture was stirred for 15 minutes. 3-Methylthiophene (12.5 g, 127 mmol) was added dropwise during 15 minutes, and the mixture was stirred for 1 hour at 40° C. After cooling, the mixture was poured into a mixture of ice (200 g) and concentrated HCl (200 mL). The mixture was kept at 45° C. for 10 minutes. After cooling, the aqueous layer was extracted with $CH_2Cl_2$ (100 mL×2), and the combined organic layers washed with brine, dried over $MgSO_4$, and concentrated in vacuo. The residue was purified by flash chromatography eluting with $CH_2Cl_2$-EtOH (10:1) to provide the title product (14.4 g, 57% yield) as a mixture of 1:1.

$^1$H—NMR ($CDCl_3$) δ 7.56 (d, J=5.1 Hz. 0.5H), 7.56 (s. 0.5H), 7.24 (s, 0.5H), 6.95 (d, J=5.1 Hz. 0.5H), 3.21 (q, j=6.6 Hz, 2H). 2.82-2.75 (m. 2H), 2.57 (s, 1.5H), 2.29 (s, 1.5H).

A mixture of 4-(3-methylthiphen-2-yl)butylic acid and 4-(4-methylthiphen-2-yl)butylic acid To a stirred solution of a mixture of 4-(3-methylthiphen-2-yl)-4-oxobutylic acid and 4-(4-methylthiphen-2-yl)-4-oxobutylic acid (14.2 g, 71.7 mmol), and potassium hydroxide (85% purity, 21.66 g, 328 mmol) was added dropwise hydrazine monohydrate (3.05 g, 61 mmol) at room temperature, and heated for 2 hours at 205° C. with removal of the distillate. After cooling, the reaction mixture was poured into a mixture of ice (150 g) and concentrated HCl (150 mL). The whole was extracted with diethyl ether (400 mL). The organic layer was washed with brine and concentrated in vacuo. The residue was purified by flash chromatography eluting with $CH_2Cl_2$-EtOH (1:0-10:1) to provide the title product (6.41 g, 49% yield).

$^1$H—NMR ($CDCl_3$) δ 7.03 (d, J=5.1 Hz, 0.5H), 6.78 (d, J=5.1 Hz, 0.5H), 6.70-6.68 (m, 0.5H), 6.61 (s, 0.5H), 2.87-2.77 (m, 2H), 2.45-2.39 (m, 2H), 2.20 (d, J=1.1 Hz, 1.5H), 2.15 (s, 1.5H), 2.05-1.91 (m, 2H).

3-Methyl-4-oxo-4,5,6,7-tetrahydrobenzothiophene

To a stirred solution of a mixture of 4-(3-methylthiphen-2-yl)butylic acid and 4-(4-methylthiphen-2-yl)butylic acid (4.2 g, 22.8 mmol) in acetic anhydride (40 mL) was added polyphosphoric acid (1.5 g) at room temperature, and the mixture was stirred for 5 minutes at 80° C. The reaction mixture was poured into ice water (200 mL), and the whole was extracted with diethyl ether (80 mL×2). The combined organic layers were washed with brine, dried over $MgSO_4$, and concentrated in vacuo. The residue was purified by flash chromatography eluting with hexane-ethyl acetate (8:1) to provide a mixture of the subtitle compound and 4-(3-methylthiophen-2-yl)butylic acid. The mixture was purified by NH-40C (Size C ; 37×300 mm, Yamazen CO.) eluting with hexane-ethyl acetate (5:1) to provide the title product (0.73 g, 19% yield).

$^1$H—NMR ($CDCl_3$) δ 6.64 (d, J=1.1 Hz, 1H), 3.05-2.98 (m, 2H), 2.58-2.50 (m, 2H), 2.44 (d, J=1.1 Hz, 3H), 2.24-2.13 (m, 2H).

2-Bromo-3-methyl-4-oxo-4,5,6,7-tetrahydrobenzothiophene

To a stirred solution of 3-methyl-4-oxo-4,5,6,7-tetrahydrobenzothiophene (500 mg, 3.01 mmol) in $CH_2Cl_2$ (15 mL) was added NBS (536 mg, 3.01 mmol) at room temperature, and the mixture stirred for 3 hours at room temperature. The reaction mixture was poured into water (50 mL) and the whole was extracted with diethyl ether (100 mL). The organic layer was washed with water (100 mL×2), brine, dried over $MgSO_4$, and concentrated in vacuo to provide the title product (686 mg, 93% yield).

$^1$H—NMR ($CDCl_3$) δ 2.94 (t, J=6.2 Hz, 2H), 2.59-2.51 (m, 2H), 2.39 (s, 3H), 2.18 (quint, 2H).

3-Methyl-4-oxo-2-(4-pyridyl)-4,5,6,7-tetrahydrobenzothiophene

The title compound was prepared according to the procedure of Example 15 using 2-bromo-3-methyl-4-oxo-4,5,6,7-tetrahydrobenzothiophene instead of 3-acetyl-2,5-dichloro-4-methylthiophene.

mp: 129–130° C.

$^1$H—NMR ($CDCl_3$) δ 8.68 (dd, J=4.8 Hz, 1.8 Hz, 2H), 7.32 (dd, J=4.8 Hz, 1.8 Hz, 2H), 3.07 (t, J=6.2 Hz, 2H), 2.64-2.57 (m, 2H), 2.54 (s, 3H), 2.29-2.17 (m, 2H).

IR ν 1660, 1590, 1400, 1180, 820 $cm^{-1}$

Anal. Calcd. for $C_{14}H_{13}NOS$: C, 69.11 H, 5.38; N, 5.76, S, 13.18. Found: C, 68.86; H, 5.24; N, 5.92, S, 12.92.

Example 21

2,5-Di(4-pyridyl)-3-(1-hydroxyethyl)-4-methylthiophene

To a stirred solution of 3-acetyl-4-methyl-2,5-di(4-pyridyl)thiophene (200 mg, 0.68 mmol) in MeOH (5 mmol) was added sodium borohydride (30 mg, 0.79 mmol) at 0° C., and the mixture was stirred for 2 hours. Water (5 mL) was added to the mixture. The whole was extracted with ethyl acetate (50 mL), the organic layer washed with brine, dried over $MgSO_4$, and concentrated in vacuo. The resulting residue was purified by flash chromatography eluting with $CH_2Cl_2$-MeOH (20:1) to provide the title product as a solid. Recrystallized from ethyl acetate gave the title product (130 mg, 75% yield).

mp: 155–157° C.

$^1$H—NMR (CDCl$_3$) δ 8.67-8.65 (m, 4H), 7.39-7.33 (m, 4H), 5.15 (q, J=7.0 Hz, 1H), 2.52 (s, 3H), 1.97 (s, 1H), 1.65 (d, J=7.0 Hz, 3H).

Anal. Calcd. for $C_{17}H_{16}N_2OS$ 0.25$H_2O$: C, 67.86 H, 5.53; N, 9.31. Found: C, 67.60; H, 5.52; N, 9.05.

Example 22

1,3-Di(4-pyridyl)-5,6-dihydro-4H-cyclopenta(c)thiophen-4-one 2.5-Dichloro-3-methylthiophene (step1)

To 3-methylthiophene (25 g, 255 mmol) was added dropwise sulfuryl chloride (45 mL, 560 mmol) over 3 hours at room temperature. After addition, the mixture was heated at reflux temperature for 2 hours and then fractionally distilled (bp 85° C., 10 mmHg) to give the subtitle compound (29.7 g, 70% yield).

$^1$H—NMR (CDCl$_3$) δ: 6.61 (s, 1H) 2.12 (s, 3H).

3-(Bromomethyl)-2,5-dichlorothiophene (step 2)

To a stirred solution of 2,5-dichloro-3-methylthiophene (25.8 g, 154 mmol) in carbon tetrachloride (47 mL) was added N-bromosuccinimide (27.5 g, 154 mmol) and benzoyl peroxide (310 mg, 1.28 mmol). The mixture was heated at reflux temperature for 8 hours. After cooling, the insolubles were filtered off. The filtrate was washed with aqueous sodium sulfite solution, dried over MgSO$_4$, and concentrated in vacuo. The residue was fractionally distilled under reduced pressure (bp 80° C., 0.5 mmHg) to give the subtitle compound (34.5 g, 91% yield).

$^1$H—NMR (CDCl$_3$) δ: 6.84 (s, 1H), 4.35 (s, 2H).

Diethyl 2-[(2,5-dichloro-3-thienyl)methyl]malonate (step 3)

To a stirred solution of sodium hydride (60% oil dispersion, 7.6 g, 190 mmol) in DMF (32 mL) was added a solution of diethyl malonate (35.2 g, 220 mmol) in THF (120 mL) at 0° C. and the mixture was stirred for 30 min at 0° C. To the mixture was added a solution of 3-(bromomethyl)-2,5-dichlorothiophene (26.9 g, 110 mmol) in THF (50 mL) at −35° C. over 1.5 hours. After stirring at −35° C. for 2 hours, the reaction mixture was poured into water and the whole extracted with ethyl acetate (200 mL×3). The combined organic layer was washed with water (200 mL), brine (200 mL), dried over MgSO$_4$ and concentrated in vacuo. Fractionally distillation of the residue under reduced pressure (bp 150° C., 1.0 mmHg) provided the subtitle compound (28.6 g, 80% yield).

$^1$H—NMR (CDCl$_3$) δ: 6.67 (s, 1H), 4.19 (q. J=7.1 Hz, 4H), 3.60 (t, J=7.7 Hz, 1H), 3.12 (d,J=7.7 Hz, 2H), 1.25 (t, J=7.1 Hz, 6H).

3-(2,5-Dichloro-3-thienyl)propanoic acid (step 4)

A solution of diethyl 2-[(2,5-dichloro-3-thienyl)methyl]malonate (36.5 g, 112 mmol) in ethanol (60 mL) and 10% aqueous sodium hydroxide solution (100 mL) was heated at reflux temperature for 3 hours. After cooling, ethanol was removed by evaporation. The aqueous residue was diluted with water and the resulting solution was made acidic (pH=2) with conc. hydrochloric acid. The whole was extracted with ethyl acetate (200 mL×3) and the combined organic layer was washed with brine (200 mL), dried over MgSO$_4$ and concentrated in vacuo to give brown solid (30.2 g), which was confirmed to be diacid by $^1$H—NMR. $^1$H—NMR (CDCl$_3$) d : 6.69 (s, 1H), 3.72 (t, J=7.5 Hz, 1H), 3.16 (d, J=7.5 Hz, 2H).] The diacid (30.2 g) was heated at 170° C. for 1 hour. The black residue was fractionally distilled under reduced pressure (bp 170° C., 0.5 mmHg) to afford the subtitle compound (18.4 g, 73% yield) as pale yellow solids.

$^1$H—NMR (CDCl$_3$) δ: 6.68 (s, 1H), 2.86 (t, J=7.2 Hz, 2H). 2.63 (t. J=7.2 Hz, 2H).

1,3-Dichloro-5,6-dihydro-4H-cyclopenta(c)thiophen-4-one (step 5)

To a stirred solution of 3-(2,5-dichloro-3-thienyl)propanoic acid (5.0 g, 24.2 mmol) in $CH_2Cl_2$ (50 mL) was added oxalyl chloride (3.5 g, 27.5 mmol) and the mixture was heated at reflux temperature for 1 hour. After cooling, volatiles were removed by evaporation. To a stirred solution of the acid chloride in $CH_2Cl_2$ (125 mL) was added aluminum chloride (4.0 g, 30 mmol) at room temperature. After stirring for 20 min, aluminum chloride (4.5 g, 33.7 mmol) was added. The mixture was stirred for additional 1 hour at room temperature. The reaction mixture was poured into ice-water and the whole extracted with dichloromethane (100 mL×3). The combined organic layer was washed with brine (100 mL), dried over MgSO$_4$ and concentrated in vacuo to give the subtitle compound as light yellow solids (4.52 g, 98% yield). The compound was used for next reaction without further purification.

$^1$H—NMR (CDCl$_3$) δ: 3.02-2.97 (m, 2H), 2.88-2.83 (m, 2H).

1.3-Di(4-pyridyl)-5,-dihydro-4H-cyclopenta(c)thiophen-4-one (step 6)

To a stirred solution of 1,3-dichloro-5,6-dihydro-4H-cyclopenta(c)thiophen-4-one (923 mg, 4.45 mmol) in dimethoxyethane (23 mL) was added 4-pyridineboronic acid (1.3 g, 10.6 mmol), saturated aqueous NaHCO$_3$ solution (7.5 mL), and bis(triphenylphosphine)palladium chloride (350 mg, 0.49 mmol) under nitrogen. The mixture was heated at reflux temperature for 36 hours. The reaction mixture was filtered through celite and the filtrate was extracted with ethyl acetate (100 mL×5). The combined organic layer was washed with brine (100 mL), dried over MgSO$_4$, and concentrated in vacuo. Chromatographic purification eluting with dichloromethane/methanol (25:1) and the subsequent recrystallization from ethyl acetate/hexane gave the title compound (645 mg, 50% yield) as yellow solids.

mp: 168–170° C.

MS (ESI) m/z: 293 (M+H)$^+$, 291 (M−H)$^-$ $^1$H—NMR (CDCl$_3$) δ 8.72-8.68 (m, 4H), 7.99-7.97 (m, 2H), 7.47-7.45 (m, 2H), 3.31-3.15 (m, 4H).

IR (KBr) 1705, 1593, 1452, 1411, 1286, 810, 777, 597, 567.

Anal. Calcd. for $C_{17}H_{12}N_2OS$; C, 69.84; H, 4.14; N, 9.58. Found; C, 69.46; H, 4.13; N, 9.33.

Example 23

2,5-Di(4-pyridyl)-3-methoxycarbonylthiophene

The title compound was prepared according to the procedure of Example 15 using methyl 2,5-dichlorothiophene carboxyrate instead of 3-acetyl-2,5-dichloro-4-methylthiophene.

mp: 133–135° C.

$^1$H—NMR (CDCl$_3$) δ 8.71-8.65 (m, 4H), 7.94 (s, 1H), 7.51-7.44 (m, 4H), 3.81 (s, 3H).

Anal. Calcd. for $C_{16}H_{12}N_2O_2S$ 0.2$H_2O$: C, 64.07 H, 4.17; N, 9.34. Found: C, 64.12; H, 4.23; N, 9.01.

Example 24

3-Acetyl-2,5-di(4-pyridyl)thiophene

The title compound was prepared according to the procedure of Example 15 using 3-acetyl-2,5-dichlorothiophene instead of 3-acetyl-2,5-dichloro-4-methylthiophene.

mp: 117–119° C.

$^1$H—NMR (CDCl$_3$) δ 8.72-8.66 (m, 4H), 7.82 (s, 1H), 7.54-7.41 (m, 4H), 2.40 (s, 3H).

Anal. Calcd. for $C_{16}H_{12}N_2OS$ 0.2H$_2$O+0.2 ethyl acetate: C, 66.91; H, 4.68; N, 9.29. Found: C, 66.87; H, 4.53; N, 9.13.

Example 25

2.5-Di(4-pyridyl)-3-(pyrrolidine-1-sulfonyl)thiophene

The title compound was prepared according to the procedure of Example 15 using 2,5-dichloro-3-(pyrrolidine-1-sulfonyl)thiophene instead of 3-acetyl-2,5-dichloro-4-methylthiophene.

mp: 193–195° C.

$^1$H—NMR (CDCl$_3$) δ 8.73-8.67 (m, 4H), 7.84 (s, 1H), 7.59 (dd, J=4.4, 1.5 Hz, 2H), 7.48 (dd, J=4.4, 1.5 Hz, 2H), 3.09 (t, J=7.0 Hz, 4H), 1.71 (t, J=7.0 Hz, 4H).

Anal. Calcd. for $C_{18}H_{17}N_3O_2S_2$ 0.25H$_2$O 0.3ethyl acetate: C, 57.31; H, 4.98; N, 10.44. Found: C, 57.59; H, 4.77; N, 10.05.

Example 26

2,5-Di(4-pyridyl)-3-ethyl-4-methylthiophene dihydrochloride 3-Ethyl-4-methylthiophene To a stirred solution of 3-bromo-4-methylthiophene (3.7 g, 20.9 mmol), bis(1,3-diphenylphosphinopropane)nickel (II)chloride (20 mg, 0.037 mmol) in diethyl ether (10 mL) was added 3M solution of methylmagnesium bromide in diethyl ether (9.0 mL, 27 mmol) at room temperature. The mixture was heated at reflux temperature for 12 hours. After cooling, 2N HCl solution was added, and the whole was extracted with diethyl ether (60 mL×2). The combined organic layers were washed with saturated NaHCO$_3$ solution, brine, dried over MgSO$_4$, and concentrated in vacuo to give colorless oil (2.37 g, 90% yield). The compound was used for next reaction without purification.

$^1$H—NMR (CDCl$_3$) δ 6.89 (s, 2H), 2.53 (q, J=7.3 Hz, 2H), 2.17 (s. 3H), 1.27 (t, J=7.3 Hz. 3H).

2.5-Dibromo-3-ethyl-4-methylthiophene

To a stirred solution of 3-ethyl-4-methylthiophene (631 mg, 5.0 mmol) in chloroform (5 mL) was added N-bromosuccinimide (NBS; 1.6 g, 8.9 mmol) at room temperature, and the mixture was stirred for 30 minutes. Water (5 mL) was added to the mixture. The whole was extracted with CH$_2$Cl$_2$ (50 mL), the organic layer washed with brine, dried over MgSO$_4$, and concentrated in vacuo to give light yellow solid (1.44 g, 99% yield). The compound was used for next reaction without purification.

$^1$H—NMR (CDCl$_3$) δ 2.57 (q, J=7.3 Hz, 2H), 2.14 (s, 3H), 1.07 (t, J=7.3 Hz, 3H). 2,5-Di(4-pyridyl)-3-ethyl-4-methylthiophene dihydrochloride The title compound was prepared according to the procedure of Example 15 using 2,5-dibromo-3-ethyl-4-methylthiophene instead of 3-acetyl-2,5-dichloro-4-methylthiophene. The HCl salt was obtained by the treatment of the free form with 10% methanolic HCl.

mp: 223–225° C.

$^1$H—NMR (CDCl$_3$) δ 8.67-8.65 (m, 4H), 7.41-7.37 (m, 4H), 2.71 (q, J=7.7 Hz, 2H), 2.35 (s, 3H), 1.25 (t, J=7.7 Hz, 3H).

Anal. Calcd. for $C_{17}H_{18}N_2Cl_2S$ 0.75H$_2$O: C, 55.66 H, 5.36; N, 7.64. Found: C, 55.64; H, 5.39; N, 7.55.

Example 27

4-Acetyl-3-methyl-2-(4-pyridyl)thiophene

2-Bromo-3-methyl-4-acetylthophene 4-Methyl-3-acetylthiophene [prepared according the method of Eric C. Bigham, U.S. Pat. No. 4,110,342 (1978).] (0.45 g), 50% aqueous solution of acetic acid (4 mL) and sodium acetate (0.29 g) were stirred vigorously. Bromine (0.51 g) was added over 15 minutes and the mixture was stirred for 18 hours. Water (50 mL) was added to the reaction mixture. The whole was extracted with Et$_2$O(50 mL×1), and the organic layer was washed with aqueous Na$_2$SO$_4$ solution, brine, dried over MgSO$_4$, and concentrated in vacuo. The resulting residue was purified by flash chromatography eluting with ethyl acetate-hexane (1:4) to give the subtitle compound (0.31 g).

$^1$H—NMR (CDCl$_3$) δ 7.95 (s, 1H). 2.55 (s, 3H). 2.4 (s, 3H).

4-Acetyl-3-methyl-2-(4-pyridyl)thiophene

The title compound was prepared according to the procedure of Example 15 using 2-bromo-3-methyl-4-acetylthophene instead of 3-acetyl-2,5-dichloro-4-methylthiophene.

mp: 87–87.5° C.

$^1$H—NMR (CDCl$_3$) δ 8.65–8.7 (m, 2H), 8.1 (s, 1H), 7.35–7.4 (m. 2H), 2.6 (s, 3H), 2.5 (s, 3H).

Anal. Calcd. for $C_{12}H_{11}NOS$: C, 66.33 H, 5.10; N, 6.45, Found: C, 66.73; H, 5.09; N, 6.51.

Example 28

3-Acetyl-2-(4-methoxyphenyl)-4-methyl-5-(4-pyridyl)thiophene hydrochloride

3-Acetyl-5-chloro-2-(4-methoxyphenyl)-4-methylthiophene

The subtitle compound was prepared according to the procedure of Example 19 using 4-(methoxy)benzeneboronic acid instead of benzeneboronic acid in step 1.

$^1$H—NMR (CDCl$_3$) δ 7.31-7.25 (m, 2H), 6.96-6.91 (m, 2H), 3.85 (s, 3H), 2.21 (s, 3H), 2.06 (s, 3H).

3-Acetyl-2-(4-methoxyphenyl)-4-methyl-5-(4-pyridyl)thiophene hydrochloride

The title compound was prepared according to the procedure of Example 15 using 3-acetyl-5-chloro-2-(4-methoxyphenyl)-4-methylthiophene instead of 3-acetyl-2,5-dichloro-4-methylthiophene. The HCl salt was obtained by the treatment of the free form with 10% methanolic HCl.

mp: 168–170° C.

$^1$H—NMR (CDCl$_3$) δ 8.67-8.65 (m, 2H), 7.38-7.34 (m, 4H), 6.99-6.95 (m, 2H), 3.86 (s, 3H), 2.33 (s, 3H), 2.14 (s, 3H).

Anal. Calcd. for $C_{19}H_{18}ClNO_2S$ 0.3H$_2$O: C, 62.48 H, 5.13; N, 3.83. Found: C, 62.38; H, 5.14; N, 3.88.

Example 29

3-Cyano-2,5-di(4-pyridyl)thiophene

3-Cyano-2,5-dibromothiophene

A mixture of 3-cyanothiophene (1 g, 9.16 mmol), bromine (4.5 g, 28.2 mmol) in acetic acid (12.5 mL) was heated at reflux temperature for 17 hours. After cooling, the mixture was poured into saturated sodium bisulfate solution (50 mL). The aqueous layer was extracted with CH$_2$Cl$_2$ (50 mL×3), the combined organic layers washed with brine, dried over MgSO$_4$, and concentrated in vacuo. The resulting residue was purified by flash chromatography eluting with hexane-ethyl acetate (20:1) to provide the subtitle product as a solid. (420 mg, 17% yield).

$^1$H—NMR (CDCl$_3$) δ 7.11 (s, 1H).

3-Cyano-2,5-di(4-pyridyl)thiophene

The title compound was prepared according to the procedure of Example 15 using 3-cyano-2,5-dibromothiophene instead of 3-acetyl-2,5-dichloro-4-methylthiophene.

mp: 205–207° C.

$^1$H—NMR (CDCl$_3$) δ 8.80-8.71 (m, 4H), 7.73-7.71 (m, 3H), 7.51-7.49 (m, 2H).

Anal. Calcd. for C$_{15}$H$_9$N$_3$S 0.2H$_2$O: C, 67.50 H, 3.55; N, 15.74. Found: C, 67.68; H, 3.67; N, 15.63.

Example 30

3-Acetyl-2-(4-chlorophenyl)-4-methyl-5-(4-pyridyl) thiophene hydrochloride

3-Acetyl-5-chloro-2-(4-chlorophenyl)-4-methylthiophene

The subtitle compound was prepared according to the procedure of Example 19 using 4-chlorobenzeneboronic acid instead of benzeneboronic acid in step 1.

$^1$H—NMR (CDCl$_3$) δ 7.42-7.26 (m, 4H), 2.21 (s, 3H), 2.08 (s, 3H).

3-Acetyl-2-(4-chlorophenyl)-4-methyl-5-(4-pyridyl) thiophene hydrochloride

The title compound was prepared according to the procedure of Example 15 using 3-acetyl-5-chloro-2-(4-chlorophenyl)-4-methylthiophene instead of 3-acetyl-2,5-dichloro-4-methylthiophene. The HCl salt was obtained by the treatment of the free form with 10% methanolic HCl.

mp: 165–167° C.

$^1$H—NMR (CDCl$_3$) δ 8.69-8.67 (m, 2H), 7.47-7.36 (m, 6H), 2.33 (s, 3H), 2.16 (s, 3H).

Anal. Calcd. for C$_{18}$H$_{15}$C$_{12}$NOS 0.2H$_2$O: C, 58.77 H, 4.22; N, 3.81. Found: C, 58.56; H, 4.15; N, 3.87.

Example 31

3-Acetyl-4-methyl-2-(4-trifluoromethylphenyl)-5-(4-pyridyl)thiophene hydrochloride 3-Acetyl-5-chloro-4-methyl-2-(4-trifluoromethylphenyl) thiophene The subtitle compound was prepared according to the procedure of Example 19 using 4-(trifluoromethyl) benzeneboronic acid instead of benzeneboronic acid in step 1.

$^1$H—NMR (CDCl$_3$) δ 7.68 (d, J=8.1 Hz, 2H), 7.49 (d, J=8.1 Hz, 2H), 2.22 (s, 3H), 2.11 (s, 3H).

3-Acetyl-4-methyl-2-(4-trifluoromethylphenyl)-5-(4-pyridyl)thiophene hydrochloride The title compound was prepared according to the procedure of Example 15 using 3-acetyl-5-chloro-4-methyl-2-(4-trifluoromethylphenyl)thiophene instead of 3-acetyl-2,5-dichloro-4-methylthiophene. The HCl salt was obtained by the treatment of the free form with 10% methanolic HCl.

mp: 185–187° C.

$^1$H—NMR (CDCl$_3$) δ 8.69 (dd, J=4,4, 1.5 Hz, 2H), 7.72 (d, J=8.1 Hz, 2H), 7.57 (d, J=8.1 Hz. 2H), 7.38 (dd, J=4,4, 1.5 Hz, 2H), 2.34 (s, 3H). 2.18 (s, 3H).

Anal. Calcd. for C$_{19}$H$_{15}$ClF$_3$NOS: C, 57.36 H, 3.80; N, 3.52. Found: C, 57.34; H, 3.79; N, 3.49.

Example 32

3-Acetyl-2-(4-fluorophenyl)-4-methyl-5-(4-pyridyl) thiophene

3-Acetyl-5-chloro-2-(4-fluorophenyl)-4-methyl thiophene

The subtitle compound was prepared according to the procedure of Example 19 using 4-fluorobenzeneboronic acid instead of benzeneboronic acid in step 1.

$^1$H—NMR (CDCl$_3$) δ 7.37-7.31 (m, 2H), 7.16-7.09 (m, 2H), 2.22 (s, 3H), 2.06 (s, 3H).

3-Acetyl-2-(4-fluorophenyl)-4-methyl-5-(4-pyridyl) thiophene

The title compound was prepared according to the procedure of Example 15 using 3-acetyl-5-chloro -2-(4-fluorophenyl) -4-methyl thiophene instead of 3-acetyl-2,5-dichloro-4-methylthiophene.

mp: 116–118° C.

$^1$H—NMR (CDCl$_3$) δ 8.67 (dd, J=4.4, 1.5 Hz, 2H), 7.45-7.36 (m, 4H), 7.15 (t, J=8.8 Hz, 2H), 2.33 (s, 3H), 2.13 (s, 3H).

Anal. Calcd. for C$_{18}$H$_{14}$FNOS: C, 69.43 H, 4.53; N, 4.50. Found: C, 69.40; H, 4.61; N, 4.57.

Example 33

3-Benzoyl-2,5-di(4-pyridyl)thiophene 2.5-Dichloro-N-methoxy-N-methyl-3-thiophenecarboxamide To a stirred solution of 2,5-dichloro-3-thiophenecarbonylchloride (1.08 g, 5.0 mmol) and pyridine (2 mL) in CH$_2$Cl$_2$ (10 mL) was added N,O-dimethylhydroxylamine hydrochloride (490 mg, 5.0 mmol) at room temperature, and the mixture was stirred for 18 hours. CH$_2$Cl$_2$ (10 mL) was added to the mixture. The combined organic layers were washed with 1N HCl solution, saturated NaHCO$_3$ solution, brine, dried over MgSO$_4$, and concentrated in vacuo to give light yellow oil (1.09 g, 91% yield). The compound was used for next reaction without purification.

$^1$H—NMR (CDCl$_3$) δ 6.91 (s, 1H), 3.61 (s, 3H), 3.33 (s, 3H). 3-Benzoyl-2,5-dichlorothiophene To a stirred solution of 2,5-dichloro-N-methoxy-N-methyl-3-thiophenecarboxamide (350 mg, 1.46 mmol) in THF (5 mL) was added 3M solution of phenylmagnesium bromide in diethyl ether (1.2 mL, 3.6 mmol) at –78° C., and the mixture was stirred for 4 hours at –30° C. Saturated ammonium chloride solution was added, and the whole was extracted with ethyl acetate (60 mL×2). The combined organic layers were washed with saturated NaHCO$_3$ solution, brine, dried over MgSO$_4$, and concentrated in vacuo. The resulting residue was purified by flash chromatography eluting with hexane-ethyl acetate (12:1) to provide the title product as a yellow oil. (212 mg. 56% yield).

$^1$H—NMR (CDCl$_3$) δ 7.85-7.79 (m, 2H), 7.65-7.58 (m, 1H). 7.53-7.46 (m, 2H), 6.98 (s, 1H).

3-Benzoyl-2,5-di(4-pyridyl)thiophene

The title compound was prepared according to the procedure of Example 15 using 3-benzoyl-2,5-dichlorothiophene instead of 3-acetyl-2,5-dichloro-4-methylthiophene.

mp: 168–170° C.

$^1$H—NMR (CDCl$_3$) δ 8.67 (dd, J=4.4, 1.8 Hz, 2H), 8.51 (dd, J=4.4, 1.8 Hz, 2H), 7.82-7.79 (m, 2H), 7.68 (s, 1H), 7.57-7.50 (m, 3H), 7.41-7.35 (m, 2H), 7.29-7.27 (m, 2H).

Anal. Calcd. for $C_{21}H_{14}N_2OS$ $0.1H_2O$: C, 73.28 H, 4.16; N, 8.14. Found: C, 73.26; H, 4.26; N, 8.13.

Example 34

2,5-Di(4-pyridyl)-4-methylthiophene-3-carbaldehyde 2,5-Dichloro-4-methylthiophene-3-carbaldehyde To a stirred solution of 2,5-dichloro-3-methylthiophene [prepared according to the method of *J. Amer. Chim. Soc.*, 1971, 333.] (11.8 g) in $CH_2Cl_2$ (200 mL) was added $TiCL_1$ (37.94 g) and dichloromethyl methyl ether (12.6 g) at $-10°$ C. After stirring for 4 hours, the reaction mixture was poured into ice-water and the whole was stirred vigorously for 30 minutes. The resulting mixture was extracted with $CH_2Cl_2$ (200 ml×1), and the organic layers was washed with saturated $NaHCO_3$ solution(100 mL×1), brine (100 mL×1), dried over $MgSO_4$, and concentrated in vacuo. The resulting residue was purified by distillation (bp : 140–145° C./10 mmHg) to provide the subtitle compound (11.75 g).

$^1$H—NMR ($CDCl_3$) δ 10.1 (s, 1H), 2.4 (s, 3H). 2.5-Di(4-pyridyl)-4-methylthiophene-3-carbaldehyde The title compound was prepared according to the procedure of Example 15 using 2,5-dichloro-4-methylthiophene-3-carbaldehyde instead of 3-acetyl-2,5-dichloro-4-methylthiophene.

mp:139–139.5° C.

$^1$H—NMR ($CDCl_3$) δ 10.0 (s, 1H), 8.7-8.8 (m, 4H), 7.35-7.44 (m, 4H), 2.58 (s, 3H).

Anal. Calcd. for $C_{16}H_{12}N_2OS$: C, 68.55 H, 4.31; N, 9.99. Found: C, 68.23; H, 4.54; N, 9.64.

Example 35

3-Acetyl-4-methyl-5-(4-pyridyl)-2-(3-thienyl)thiophene

3-Acetyl-5-chloro-4-methyl-2-(3-thienyl)thiophene

The subtitle compound was prepared according to the procedure of Example 19 using 3-thiopheneboronic acid instead of benzeneboronic acid in step 1

$^1$H—NMR ($CDCl_3$) δ 7.40 (dd, J=4.8, 2.9 Hz, 1H). 7.32 (dd, J=2.9. 1.5 Hz, 1H), 7.09 (dd, J=4.8, 1.5 Hz, 1H), 2.21 (s, 3H), 2.15 (s, 3H).

3-Acetyl-4-methyl-5-(4-pyridyl)-2-(3-thienyl)thiophene

The title compound was prepared according to the procedure of Example 15 using 3-acetyl-5-chloro-4-methyl-2-(3-thienyl)thiophene instead of 3-acetyl-2,5-dichloro-4-methylthiophene.

mp: 98–100° C.

$^1$H—NMR ($CDCl_3$) δ 8.67 (dd, J=4.4, 1.5 Hz, 2H), 7.43 (dd, J=4.8, 2.9 Hz, 1H), 7.38 (dd, J=4.8, 1.1 Hz, 1H), 7.36 (dd, J=4.4, 1.5 Hz, 2H), 7.17 (dd, J=4.8, 1.1 Hz, 1H), 2.32 (s, 3H), 2.23 (s, 3H).

Anal. Calcd. for $C_{16}H_{13}NOS_2$ $0.2H_2O$: C, 63.42 H, 4.46; N, 4.62. Found: C, 63.30; H, 4.44; N, 4.52.

Example 36

3-Acetyl-4-methyl-5-(4-pyridyl)-2-(4-methylthiophenyl)thiophene

3 -Acetyl-5-chloro-4-methyl-2-(4-methylthiophenyl)thiophene

The title compound was prepared according to the procedure of Example 19 using 4-(methylthio)benzene boronic acid instead of benzeneboronic acid in step 1.

$^1$H—NMR ($CDCl_3$) δ 7.26 (s, 4H), 2.52 (s, 3H), 2.21 (s, 3H). 2.09 (s, 3H).

3-Acetyl-4-methyl-5-(4-pyridyl)-2-(4-methylthiophenyl)thiophene

The title compound was prepared according to the procedure of Example 15 using 3-acetyl-5-chloro-4-methyl-2-(4-methylthiophenyl)thiophene instead of 3-acetyl-2,5-dichloro-4-methylthiophene.

mp: 106–108° C.

$^1$H—NMR ($CDCl_3$) δ 8.67 (dd, J=4.4, 1.5 Hz, 2H), 7.72-7.27 (m, 6H), 2.54 (s, 3H), 2.32 (s, 3H), 2.17 (s, 3H).

Anal. Calcd. for $C_{19}H_{17}NOS_2$ 0.1 hexane: C, 67.63 H, 5.33; N. 4.09. Found: C, 67.75; H, 5.20; N, 3.81.

Example 37

3-Acetyl-2-(4-morpholino)-5-(4-pyridyl)thiophene

3-Acetyl-5-chloro-2-(4-morpholino)thiophene

A mixture of 3-acetyl-2,5-dichlorothiophene (2 g, 10 mM) and morpholine (2 mL) was heated at 135° C. for 1 hour. After cooling, the residue was purified by flash chromatography eluting with ethyl acetate-hexane (1:5) to give the subtitile compound (2.3 g. 94% yield).

$^1$H—NMR ($CDCl_3$) δ 7.08 (s, 1H), 3.89-3.85 (m. 4H), 3.15-3.11 (m, 4H), 2.46 (s, 3H).

3-Acetyl-2-(4-morpholino)-5-(4-pyridyl)thiophene

The title compound was prepared according to the procedure of Example 15 using 3-acetyl-5-chloro-2-(4-morpholino)thiophene instead of 3-acetyl-2,5-dichloro-4-methylthiophene.

mp: 147–149° C.

$^1$H—NMR ($CDCl_3$) δ 8.58-8.55 (m, 2H), 7.68 (s, 1H), 7.39-7.36 (m, 2H), 3.94-3.90 (m, 4H), 3.30-3.26 (m, 4H), 2.55 (s, 3H).

MS (ESI) m/z: 289 (M+H)$^+$

Anal. Calcd. for $C_{15}H_{16}N_2O_2S$ $0.2H_2O$: C, 61.71 H, 5.66; N, 9.59. Found: C, 61.94; H, 5.26; N, 9.62.

Example 38

3-Acetyl-2-(4-methylpiperazin-1-yl)-5-(4-pyridyl)thiophene 3-Acetyl-5-chloro-2-(4-methylpiperazin-1-yl)thiophene The subtitle compound was prepared according to the procedure of Example 37 using N-methylpiperazine instead of morpholine.

$^1$H—NMR ($CDCl_3$) δ 7.06 (s, 1H), 3.18-3.14 (m, 4H), 2.63-2.58 (m, 4H), 2.47 (s, 3H), 2.35 (s, 3H).

3 -Acetyl-2-(4-methylpiperazin-1-yl)-5-(4-pyridyl)thiophene

The title compound was prepared according to the procedure of Example 15 using 3-acetyl-5-chloro-2-(4-methylpiperazin-1-yl)thiophene instead of 3-acetyl-2,5-dichloro-4-methylthiophene.

mp: 115–117° C.

$^1$H—NMR ($CDCl_3$) δ 8.57-8.53 (m, 2H), 7.67 (s, 1H), 7.38-7.35 (m, 2H), 3.33-3.29 (m, 4H), 2.67-2.63 (m, 4H), 2.54 (s, 3H), 2.38 (s, 3H).

MS (ESI) m/z: 302 (M+H)$^+$

Anal. Calcd. for $C_{16}H_{19}N_3OS$ $0.35H_2O$: C, 62.45 H, 6.45; N, 13.66. Found: C, 62.85; H, 6.13; N, 13.27.

Example 39

2,5-Di(4-pyridyl)-4-methylthiophene-3-carbaldehyde oxime dihydrochloride

A mixture of 2,5-di(4-pyridyl)-4-methylthiophene-3-carbaldehyde (0.14 g), hydroxylamine hydrochloride (0.04 g), and pyridine (0.04 mL) in MeOH (3 mL) was heated at reflux temperature for 16 hours. After cooling, the volatiles were removed by evaporation. The resulting residue was dissolved in 10% methanolic HCl (5 mL) and the solution was concentrated in vacuo again. The resulting solid was washed with water (50 mL) and $CH_2Cl_2$ (30 mL) to provide the title compound (0.045 g).

mp:258–261° C. (decomp.)

$^1$H—NMR (DMSO-$d_6$) δ 11.7–11.8 (br, 1H), 8.92-8.87 (m, 4H), 8.25 (s, 1H), 7.95–8.05 (m, 2H), 7.85–7.95 (m, 2H), 2.51 (s, 3H).

Anal. Calcd. for $C_{16}H_{13}N_3OS$ 2HCl 1.5$H_2O$: C, 48.61 H, 4.59; N, 10.63. Found: C, 48.47; H, 4.48; N, 10.36.

Example 40

3-Acetyl-2-(N-benzyl-N-methylamino)-5-(4-pyridyl) thiophene hydrochloride

3-Acetyl-2-(N-benzyl-N-methylamino)-5-chlorothiophene

The subtitle compound was prepared according to the procedure of Example 37 using N-methylbenzylamine instead of morpholine.

$^1$H—NMR (CDCl$_3$) δ 7.33-7.25 (m, 5H), 7.02 (s, 1H), 4.40 (s, 2H), 2.83 (s, 3H), 2.45 (s, 3H).

3-Acetyl-2-(N-benzyl-N-methylamino)-5-(4-pyridyl) thiophene hydrochloride The title compound as a free form was prepared according to the procedure of Example 15 using 3-acetyl-2-( N-benzyl-N-methylamino)-5-chlorothiophene instead of 3-acetyl-2,5-dichloro-4-methylthiophene. Treatment of the free form by 10% methanolic hydrochloride gave the title HCl salt.

mp: 199–202° C.

$^1$H—NMR (CDCl$_3$) δ 8.63 (d, J=6.1 Hz, 2H), 8.55 (s, 1H), 8.00 (d, J=6.1 Hz, 2H), 7.38-7.23 (m, 5H), 4.76 (s, 2H), 3.10 (s, 3H), 2.49 (s, 3H).

Anal. Calcd. for $C_{19}H_{18}N_2OS$ HCl: C, 62.96 H, 5.39; N, 7.73. Found: C, 62.78; H, 5.46; N, 7.77.

Example 41

1,3-Di(4-pyridyl)-4,5,6,7-tetrahydrobenzo(c)thiophen-4-one 4-(2.5-dichlorothiophen-3-yl)-4-ketobutylic acid To a stirred suspension of succinic anhydride (5 g, 50 mM) and aluminum chloride (15 g, 110 mM) in $CS_2$ (30 mL) was added dropwise a solution of 2,5-dichlorothiophene (7.65 g, 50 mM) in $CS_2$ (20 mL) at −30~ −10° C. under nitrogen. After stirring for 30 minutes at 0° C., the black mixture was poured into ice-water. The solution was made basic by 10% NaOH solution, and the whole was washed with $Et_2O$. The aqueous layer was made acidic by 2N. HCl solution, and the whole was extracted with ethyl acetate (200 mL×3), the combined organic layers washed with brine, dried over $MgSO_4$, and concentrated in vacuo to give the subtitle compound (3 g, 24% yield).

$^1$H—NMR (CDCl$_3$) δ 7.22 (s, 1H), 3.23 (t, J=6.3 Hz, 2H), 2.78 (t, J=6.3 Hz, 2H).

MS (EI) m/z: 252 (M$^+$)

4-(2,5-dichlorothiophen-3-yl) butylic acid

The mixture of 4-(2,5-dichlorothiophen-3-yl)-4-ketobutylic acid (2.53 g, 10 mM), hydrazine monohydrate (2 mL) and NaOH (2 g) in diethylene glycol (20 mL) was heated at 160° C. for 1 hour. After cooling, the mixture was made acidic by 2N HCl. The whole was extracted with ethyl acetate (100 mL×2), the combined organic layers washed with brine, dried over $MgSO_4$, and concentrated in vacuo. Chromatographic purification eluting with ethyl acetate gave the subtitle compound (0.45 g, 19% yield).

$^1$H—NMR (CDCl$_3$) δ 6.65 (s, 1H), 2.59 (t, J=7.4 Hz, 2H), 2.38 (t, i =7.4 Hz, 2H), 1.96-1.83 (m, 2H).

3-Dichloro-4,5,6,7-tetrahydrobenzo(c)thiophen-4-one

The subtitle compound was prepared according to the procedure of Example 22 using 4-(2,5-dichlorothiophen-3-yl)butylic acid instead of 3-(2,5-dichloro-3-thienyl) propanoic acid in step 5.

$^1$H—NMR (CDCl$_3$) δ 2.76 (t, J=6.1 Hz, 2H), 2.55 (t, J=6.1 Hz, 2H), 2.11-2.00 (m, 2H).

MS (EI) m/z: 221 (M$^+$)

1.3-Di(4-pyridyl)-4,5,6,7-tetrahydrobenzo(c)thiophen-4-one

The title compound was prepared according to the procedure of Example 22 using 1,3-dichloro-4,5,6,7-tetrahydrobenzo(c)thiophen-4-one instead of 1,3-dichloro-5,6-dihydro-4H-cyclopenta(c)thiophen-4-one in step 6.

mp: 157–160° C.

MS (ESI) m/z: 307 (M+H)

$^1$H—NMR (CDCl$_3$) δ 8.72-8.66 (m, 4H), 7.48 (d, J=6.1 Hz, 2H), 7.39 (d, J=6.1 Hz, 2H), 3.05 (t, J=5.9 Hz, 2H), 2.64 (t, J=5.9 Hz, 2H), 2.18-2.11 (m, 2H).

Anal. Calcd. for $C_{18}H_{14}N_2OS$ 0.2$H_2O$; C, 69.74; H, 4.68; N, 9.04. Found; C, 69.84; H, 4.62; N, 8.80.

Example 42

3-Acetyl-2-phenoxy-5-(4-pyridyl)thiophene

3-Acetyl-5-chloro-2-phenoxythiophene

A mixture of phenol (1.22 g, 13 mM) and NaH (60% oil dispersion, 0.52 g, 13 mM) in DMF (25 mL) was stirred for 40 minutes at room temperature. 3-Acetyl-2,5-dichlorothiophene (1.95 g, 10 mM) and copper (I) iodide (50 mg) was added to the above mixture, and the resulting mixture was heated at 130° C. for 1.5 hours. After cooling, the mixture was poured into water. The whole was extracted with ethyl acetate-hexane (1:1, 200 mL×1, 100 mL×1), and the combined organic layers washed with water, brine, dried over $MgSO_4$, and concentrated in vacuo. Chromatographic purification eluting with ethyl acetate-hexane (1:20) provided the subtitle compound (1.69 g. 67% yield) as a brown oil.

$^1$H—NMR (CDCl$_3$) δ 7.46-7.38 (m, 2H), 7.29-7.16 (m, 3H), 7.10 (s, 1H), 2.49 (s, 3H).

3-Acetyl-2-phenoxy-5-(4-pyridyl)thiophene

The title compound was prepared according to the procedure of Example 15 using 3-acetyl-5-chloro-2-phenoxythiophene instead of 3-acetyl-2,5-dichloro-4-methylthiophene.

mp: 103–105° C.

$^1$H—NMR (CDCl$_3$) δ 8.56-8.53 (m, 2H), 7.72 (s, 1H), 7.51-7.43 (m, 2H), 7.35-7.24 (m, 5H), 2.59 (s, 3H).

MS (ESI) m/z: 296 (M+H)$^+$

Anal. Calcd. for $C_{17}H_{13}NO_2S$: C, 69.13 H, 4.44; N, 4.74. Found: C, 68.73; H, 4.64; N, 4.70.

Example 43

2-Acetyl-3,4-dimethyl-5-(4-pyridyl)thieno[2,3-b] thiophene

The title compound was prepared according to the procedure of Example 15 using 2-acetyl-5-bromo-3,4-dimethylthieno[2,3 -b]thiophene (commercially available from Maybridge Chemical Co. Ltd.) instead of 3-acetyl-2, 5-dichloro-4-methylthiophene.

mp: 171–173° C.

MS (ESI) m/z 288 (M+H)$^+$ $^1$H—NMR (CDCl$_3$) δ 8.71-8.67 (m, 2H), 7.38-7.33 (m, 2H), 2.89 (s, 3H), 2.59 (s, 3H), 2.58 (s, 3H).

Anal. Calcd. for $C_{15}H_{13}NOS_2$; C, 62.69; H, 4.56; N, 4.87. Found; C, 62.77; H, 4.24; N, 5.02.

Example 44

3-Acetyl-2-13-(4-fluorophenoxy)phenoxyl-5-(4-pyridyl) thiophene hydrochloride

3-Acetyl-5-chloro-2-{3-(4-fluorophenoxy)phenoxy}-thiophene

The subtitle compound was prepared according to the procedure of Example 42 using 3-(4-fluorophenoxy)phenol instead of phenol.

$^1$H—NMR (CDCl$_3$) δ 7.36-7.29 (m, 2H), 7.11-7.00 (m, 4H), 6.89-6.77 (m, 3H), 2.46 (s, 3H).

3-Acetyl-2-{3-(4-fluorophenoxy)phenoxy}-5-(4-pyridyl) thiophene hydrochloride

The title compound as a free form was prepared according to the procedure of Example 15 using 3-acetyl-5-chloro-2-{-3 -(4-fluorophenoxy)phenoxy}-thiophene instead of 3-acetyl-2,5-dichloro-4-methylthiophene. Treatment of the free form by 10% methanolic HCl gave the title salt.

mp: 251–253° C.

$^1$H—NMR (DMSO-d$_6$) δ 8.76 (d. J=5.6 Hz, 2H), 8.37 (s, 1H), 8.18 (d, J=5.6 Hz, 2H), 7.55 (t, J=8.2 Hz, 1H), 7.32-7.13 (m, 6H), 7.02-6.98 (m, 1H), 2.56 (s, 3H). MS (ESI) m/z: 406 (M+H)$^+$

Anal. Calcd. for C$_{23}$H$_{16}$NO$_3$FS HCl: C, 62.51 H, 3.88; N, 3.17. Found: C, 62.23; H, 3.64; N, 3.45.

Example 45 and 46

1-Chloro-3-(4-pyridyl)-4,5,6,7-tetrahydrobenzo(c)thiophen-4-one and 3-Methanesulfonyl-1-(4-pyridyl)4,5,6,7-tetrahydrobenzo(c)thiophen-4-one The title compounds were prepared according to the procedure of Example 15 using 1-chloro-3-methylsulfonyl-4,5,6,7-tetrahydrobenzo(c)thiophen-4-one (commercially available from Maybridge Chemical Co. Ltd.) instead of 3-acetyl-2,5-dichloro-4-methylthiophene.

3-Methanesulfonyl-1-(4-pyridyl)-4,5,6,7-tetrahydrobenzo(c)thiophen-4-one mp: 194–197° C.

MS (El) mz: 307 (M$^+$)

$^1$H—NMR (CDCl$_3$) δ 8.76-8.72 (m, 2H), 7.39-7.34 (m, 2H), 3.57 (s, 3H), 3.00 (t, J=6.1 Hz, 2H), 2.73 (t, J=6.3 Hz, 2H), 2.17-2.10 (m, 2H).

Anal. Calcd. for C$_{14}$H$_{13}$NO$_3$S$_2$ 0.2H$_2$0; C, 54.07; H, 4.34; N, 4.50. Found; C, 54.11; H, 4.36; N, 4.55.

1-Chloro-3-(4-pyridyl)-4,5,6,7-tetrahydrobenzo(c)thiophen-4-one mp: 93–95° C.

MS (EI) m/z: 262, 263

$^1$H—NMR (CDCl$_3$) δ 8.66-8.62 (m, 2H), 7.44-7.40 (m, 2H), 2.84 (t, J=6.1 Hz, 2H), 2.57 (t, J=6.1 Hz, 2H), 2.17-2.05 (m, 2H).

Anal. Calcd. for C$_{13}$H$_{10}$ClNOS; C, 59.20; H, 3.82; N, 5.31. Found; C, 59.51; H, 3.73; N, 5.38.

Example 47

3-Methylthio-1-(4-pyridyl)-4,5,6,7-tetrahydrobenzo(c)thiophen-4-one

The title compound was prepared according to the procedure of Example 15 using 1-bromo-3-methylthio-4,5,6,7-tetrahydrobenzo(c)thiophen-4-one (commercially available from Maybridge Chemical Co. Ltd.) instead of 3-acetyl-2,5-dichloro-4-methylthiophene.

mp: 115–116° C.

$^1$H—NMR (CDCl$_3$) δ 8.65-8.62 (m, 2H), 7.34-7.31 (m, 2H), 2.99 (t, J=6.1 Hz, 2H), 2.64 (s, 3H), 2.60 (t, J=6.3 Hz, 2H), 2.11–2.00 (m, 2H).

Anal. Calcd. for C$_{14}$H$_{13}$NOS$_2$; C, 61.06; H, 4.76; N, 5.09. Found; C, 60.85; H, 4.86; N, 5.58.

Example 48

[2,5-Di-(4-pyridyl)3-thienyl]butan-3-one (2.5-Dichloro-3-thienyl)butan-3-one

To a stirred solution of 3-(2,5-dichloro-3-thienyl) propanoic acid (0.225 g) in Et$_2$O (5 mL) was added 1.05M MeLi in Et$_2$O (2.0 mL) at 0° C. under nitrogen. After stirring at 0° C. for 30 minutes, the mixture was warmed to room temperature and stirred for 1 hour. The reaction was quenched by the addition of phosphate buffer solution (pH=7), and the resulting mixture was extracted with Et$_2$O (30 mL). The organic layer was washed with water, brine, dried over MgSO$_4$, and concentrated in vacuo. Chromatographic purification of the residue eluting with hexane-ethyl acetate (4:1) to give the title compound (0.173 g).

$^1$H—NMR (CDCl$_3$) δ 6.65 (s, 1H), 2.65–2.82 (m, 4H), 2.16 (s, 3H). [2,5-Di-(4-pyridyl)3-thienyl]butan-3-one The title compound was prepared according to the procedure of Example 15 using (2,5-dichloro-3-thienyl)butan-3-one instead of 3-acetyl-2,5-dichloro-4-methylthiophene.

mp: 162–163° C.

$^1$H—NMR (CDCl$_3$) δ 8.67–8.70 (m, 2H), 8.60-8.64 (m, 2H), 7.45–7.48 (m, 2H), 7.38–7.41 (m, 3H), 3.03 (t. J=8 Hz, 2H), 2.79 (t, J=8 Hz, 2H), 2.16 (s, 3H).

Anal. Calcd. for C$_{18}$H$_{16}$N$_2$OS 0.15H$_2$O: C, 69.49. H, 5.28; N, 9.00. Found: C, 69.77; H,4.92; N, 8.61.

Example 49

N,N-Dimethyl-3-[2,5-di-(4-pyridyl)3-thienyl]propionamide N,N-Dimethyl-3-(2,5-di-chloro-3-thienyl)propionamide To a stirred solution of oxalyl chloride (1 mL) in CH$_2$Cl$_2$ (3 mL) was added 3-(2,5-dichloro-3-thienyl)propanoic acid (0.2 g) in CH$_2$Cl$_2$ (2 mL) under nitrogen. The resulting mixture was heated at reflux temperature for 1 hour. After cooling, volatiles were removed by evaporation to give the corresponding acid chloride, which was used for next reaction without further purification.

To a stirred 2M solution of dimethylamine in THF (4 mL) was added the crude acid chloride in CH$_2$Cl$_2$ (5 mL) under nitrogen. After stirring for 1 hour, water (20 mL) was added to the reaction mixture and the whole was extracted with CH$_2$Cl$_2$ (20 mL). The organic layer was washed with brine, dried over MgSO$_4$, and concentrated in vacuo. The residue was purified by flash chromatography eluting with hexane-ethyl acetate (3:1) to give title compound (0.20 g).

$^1$H—NMR (CDCl$_3$) δ 6.71 (s, 1H), 2.97 (s, 3H), 2.96 (s, 3H), 2.87 (t, J=8 Hz, 2H), 2.54 (t, J=8 Hz, 2H).

N,N-Dimethyl-3-[2,5-di-(4-pyridyl)3-thienyl]propionamide

The title compound was prepared according to the procedure of Example 15 using N-dimethyl-3-(2,5-di-chloro-3-thienyl)propionamide instead of 3-acetyl-2,5-dichloro-4-methylthiophene.

mp: 166.5–167° C.

$^1$H—NMR (CDCl$_3$) δ 8.60–8.69(m, 4H), 7.41–7.48 (m, 5H), 3.13 (t, J=8 Hz, 2H), 2.96 (s, 3H), 2.95 (s, 3H), 2.62 (t, J=8 Hz, 2H).

Anal. Calcd. for C$_{19}$H$_{19}$N$_3$OS: C, 67.63 H, 5.68; N, 12.45. Found: C, 67.55; H, 5.92; N, 12.35.

Example 50

3-Acetyl-2-(1-piperidino)-5-(4-pyridyl)thiophene 3-Acetyl-5-chloro-2-(1-piperidino)thiophene The subtitle compound was prepared according to the procedure of Example 37 using piperidine instead of morpholine.

$^1$H—NMR (CDCl$_3$) δ 7.05 (s, 1H), 3.05-3.00 (m, 4H), 2.48 (s, 3H), 1.81-1.72 (m, 4H), 1.63–1.55 (m, 2H).

3-Acetyl-2-(1-piperidino)-5-(4-pyridyl)thiophene

The title compound was prepared according to the procedure of Example 15 using 3-acetyl-5-chloro-2-(1-piperidino)thiophene instead of 3-acetyl-2,5-dichloro-4-methylthiophene.

mp: 82–84° C.

$^1$H—NMR (CDCl$_3$) δ 8.56-8.52 (m, 2H), 7.67 (s, 1H), 7.37-7.33 (m, 2H), 3.24-3.18 (m, 4H), 2.54 (s. 3H), 1.86-1.76 (m, 4H), 1.69-1.62 (m, 2H).

MS (ESI) m/z: 287 (M+H)$^+$

Anal. Calcd. for C$_{16}$H$_{18}$N$_2$OS: C, 67.10 H, 6.33; N, 9.78. Found: C, 67.21; H, 6.49; N, 9.46.

Example 51

Ethyl 3-[2,5-di-(4-pyridyl)3-thienyl]propionate dihydrochloride

Ethyl 3-(2,5-di-chloro-3-thienyl)propionate

To a stirred solution of oxalyl chloride (1 mL) in CH$_2$Cl$_2$ (2 mL) was added 3-(2,5-dichloro-3-thienyl)propanoic acid (0.2 g) in CH$_2$Cl$_2$ (3 mL) under nitrogen. The resulting mixture was heated at reflux temperature for 1 hour. After cooling, volatiles were removed by evaporation to give the corresponding acid chloride, which was used for next reaction without further purification. To a stirred absolute ethanol (5 mL) was added the crude acid chloride in CH$_2$Cl$_2$ (5 mL) under nitrogen. After stirring for 1 hour, water (30 mL) was added to the reaction mixture and the whole was extracted with CH$_2$Cl$_2$ (30 mL). The organic layer was washed with saturated NaHCO$_3$ solution, brine, dried over MgSO$_4$, and concentrated in vacuo. The residue was purified by flash chromatography eluting with hexane-ethyl acetate (1:1) to give the subtitle compound (0.17 g).

$^1$H—NMR (CDCl$_3$) δ 6.767 (s, 1H), 4.14 (q, J=7 Hz, 2H), 2.84 (t, J=8 Hz, 2H), 2.55 (t, J=8 Hz, 2H), 1.25 (t, J=7 Hz, 3H).

Ethyl 3-[2,5-di-(4-pyridyl)3-thienyl]propionate dihydrochloride

The title compound was prepared according to the procedure of Example 15 using ethyl 3-(2,5-di-chloro-3-thienyl)propionate instead of 3-acetyl-2,5-dichloro-4-methylthiophene.

The crude product (purified by column chromatography on silica(CH$_2$Cl$_2$-ethyl acetate-MeOH=1:1:0.06)) was dissolved in 10% methanolic HCl (1 mL) and the solution was concentrated in vacuo. The resulting solid was recrystallized from EtOH-diisopropyl ether to give the title compound (0.053 g).

mp: 205–208° C. (decomp.).

$^1$H—NMR (DMSO-d$_6$) δ 8.87–8.91(m, 4H), 8.33 (s, 1H), 8.22 (br. d, 2H), 7.97 (br. d, 2H),4.03 (q, J=7 Hz, 2H), 3.06 (t, J=8Hz, 2H), 2.82 (t, J 8 Hz, 2H), 1.13 (t, J=7 Hz, 3H).

Anal. Calcd. for C$_{19}$H$_{18}$N$_2$O$_2$S 2HCl 0.75H$_2$O: C, 53.71 H, 5.10; N, 6.59. Found: C, 53.66; H, 5.26; N, 6.49.

Example 52

N-Methyl-{2,5-di(4-pyridyl)thiophen-3-yl}carboxamide

N-Methyl-(2,5-dichlorothiophen-3-yl)carboxamide

To a stirred solution of 2,5-dichloro-3-thenoyl chloride (commercially available from Maybridge Chemical Co. Ltd. 1.07 g, 5 mM) in CH$_2$Cl$_2$ (5 mL) was added 40% aqueous solution of methylamine (1 mL) at room temperature. After stirring overnight, the mixture was poured into CH$_2$Cl$_2$ (50 mL). The whole was washed with water (40 mL), brine (40 mL), dried over MgSO$_4$, and concentrated in vacuo. The resulting solid was triturated with Et$_2$O-hexane to give the subtitle compound (0.54 g, 51% yield).

$^1$H—NMR (CDCl$_3$) δ 7.22 (s, 2H), 3.00 (s, 3H), 2.98 (s, 3H).

N-Methyl-{5-chloro-2-(4-pyridyl)thiophen-3-yl}carboxamide

The subtitle compound was prepared according to the procedure of Example 15 using N-methyl-(2,5-dichlorothiophen-3-yl)carboxamide instead of 3-acetyl-2,5-dichloro-4-methylthiophene.

mp: 174–177° C.

MS (ESI) m/z: 253 (M+H)$^+$ $^1$H—NMR (CDCl$_3$) δ 8.68-8.62 (m, 2H), 7.39-7.33 (m. 2H), 7.15 (s, 1H), 5.53 (br.s, 1H), 2.85 (d, J=4.9 Hz, 3H).

Anal. Calcd. for C$_{11}$H$_9$ClN$_2$OS; C, 52.28; H, 3.59; N, 11.08. Found; C, 52.14; H, 3.72; N, 10.93.

N-Methyl-{2,5-di(4-pyridyl)thiophen-3-yl}carboxamide

The title compound was prepared according to the procedure of Example 15 using N-methyl-{5-chloro-2-(4-pyridyl)thiophen-3-yl}carboxamide instead of 3-acetyl-2,5-dichloro4-methylthiophene.

mp: 197–199° C.

MS (ESI) m/z: 296 (M+H)$^+$, 294 (M–H)$^+$ $^1$H—NMR (CDCl$_3$) δ 8.72-8.63 (m, 4H), 7.71 (s, 1H), 7.49-7.44 (m, 4H), 5.60 (br.s, 1H), 2.90 (d, J=4.9 Hz, 3H).

Anal. Calcd. for C$_{16}$H$_{13}$N$_3$OS 0.4H$_2$O; C, 63.51; H, 4.60; N, 13.89. Found; C, 63.73; H, 4.48; N, 13.78.

Example 53

3-(2-Fluorophenyl)-1-(4-pyridyl)-5,6-dihydro-4H-cyclopenta(c)thiophene-4-one

1-Chloro-3-(2-fluorophenyl)-5,6-dihydro-4H-cyclopenta (c)thiophene-4-one (step 1)

To a stirred solution of 1,3-dichloro-5,6-dihydro-4H-cyclopenta(c)thiophene-4-one (250 mg, 1.21 mmol) in DME (7.5 mL) was added 2-fluorobenzeneboronic acid (177 mg, 1.27 mmol), saturated aqueous NaHCO$_3$ solution (2.5 mL) and bis(triphenylphosphine)palladium(II)chloride (100 mg, 0.14 mmol) at room temperature under nitrogen. The mixture was heated at reflux temperature for 8 hours. The whole was extracted with ethyl acetate (50 mL×2), and the combined organic layers were washed with brine, dried over MgSO$_4$, and concentrated in vacuo. The residue was purified by flash chromatography eluting with hexane-ethyl acetate (10:1) to provide the subtitle compound (118 mg, 37% yield).

$^1$H—NMR (CDCl$_3$) δ 8.21-8.14 (m, 1H), 7.39-7.10 (m, 3H), 3.07-2.80 (m, 4H). 3-(2-Fluorophenyl)-1-(4-pyridyl)-5,6-dihydro-4H-cyclopenta(c)thiophene-4-one (step 2)

To a stirred solution of 1-chloro-3-(2-fluorophenyl)-5,6-dihydro-4H-cyclopenta(c)thiophene-4-one (118 mg, 0.443 mmol) in DME (7.5 mL) was added 4-pyridineboronic acid (130 mg, 1.06 mmol), saturated aqueous NaHCO$_3$ solution (2.5 mL) and bis(triphenylphosphine)palladium(II)chloride (100 mg, 0.14 mmol) at room temperature under nitrogen. The mixture was heated at reflux temperature for 20 hours. The whole was extracted with ethyl acetate (50 mL×2), and the combined organic layers were washed with brine, dried over MgSO$_4$, and concentrated in vacuo. The residue was purified by flash chromatography eluting with hexane-ethyl acetate (1:1) to provide the title product (125 mg, 91% yield).

mp: 133–135° C.

$^1$H—NMR (CDCl$_3$) δ 8.66 (dd, J=4.6, 1.6 Hz, 2H), 8.15 (dt, J=7.7, 1.8 Hz, 1H), 7.71-7.16 (m, 5H), 3.28-3.11 (m, 4H).

Anal. Calcd. for C$_{18}$H$_{12}$FNOS 0.1hexane+0.3H$_2$O: C, 69.08 H, 4.36; N, 4.33. Found: C, 69.28; H, 4.35; N, 3.94.

Example 54

1-Chloro-3-(4-pyridyl)-5,6-dihydro-4H-cyclopenta(c)thiophene-4-one

The title compound was prepared according to the method of Example 53 using 4-pyridineboronic acid instead of 2-fluorobenzeneboronic acid in step 1.

mp: 163–165° C.

¹H—NMR (CDCl₃) δ 8.67 (dd, J=4.5, 1.6 Hz, 2H), 7.86 (dd, J=4.5, 1.6 Hz, 2H), 3.12-3.06 (m, 2H), 2.97-2.91 (m, 2H).

Anal. Calcd. for $C_{12}H_8ClNOS$ 0.1ethyl acetate: C, 57.61 H, 3.43; N, 5.42. Found: C, 57.96; H, 3.66; N, 5.16.

Example 55

O-Acetyl-2,5-di(4-pyridyl)-4-methylthiophene-3-carbaldehyde oxime

To a stirred solution of 2,5-di(4-pyridyl)-4-methylthiophene-3-carbaldehyde oxime (0.145 g) in CH₂Cl₂ (3 mL) was added acetic anhydride (0.3 mL). The mixture was heated at reflux temperature for 2 hours. Acetic anhydride (1.0 mL) was additionally added to the reaction mixture, and the mixture was heated at reflux temperature for 2 hours. After cooling, the reaction mixture was poured into saturated aqueous NaHCO₃ solution (10 mL), and partitioned. The aqueous layer was extracted with CH₂Cl₂ (20 mL×1), the combined organic layers washed with brine, dried over MgSO₄, and concentrated in vacuo. The residue was purified by flash chromatography eluting with ethyl acetate-CH₂Cl₂-methanol (1:1:0.1) to give the solid, which was recrystallized from isopropyl alchol-isoproyl ether to give title compound (0.085 g).

mp: 124–125° C.

¹H—NMR (CDCl₃) δ 8.71–8.75 (m, 4H), 8.38 (s, 1H), 7.34–7.41 (m, 4H), 2.60 (s, 3H), 2.23 (s, 3H).

Anal. Calcd. for $C_{18}H_{15}N_3O_2S$: C, 64.08 H, 4.48; N, 12.45. Found: C, 63.94; H, 4.26; N, 12.47.

Example 56

3-Acetyl-2-(2-fluorophenoxy)-5-(4-pyridyl)thiophene

3-Acetyl-5-chloro-2-(2-fluorophenoxy)thiophene

The subtitle compound was prepared according to the procedure of Example 42 using 2-fluorophenol instead of phenol.

¹H—NMR (CDCl₃) δ 7.35-6.80 (m, 5H), 2.54 (d, J=0.5 Hz,. 3H).

3-Acetyl-2-(2-fluorophenoxy)-5-(4-pyridyl)thiophene

The title compound was prepared according to the procedure of Example 15 using 3-acetyl-5-chloro-2-(2-fluorophenoxy)thiophene instead of 3-acetyl-2,5-dichloro-4-methylthiophene.

mp: 93–96° C.

¹H—NMR (CDCl₃) δ 8.56-8.52 (m, 2H), 7.71 (s, 1H), 7.39-7.20 (m, 6H), 2.64 (s, 3H).

MS (ESI) m/z: 314 (M+H)⁺

Anal. Calcd. for $C_{17}H_{12}NO_2FS$: C, 65.16 H, 3.86; N, 4.47. Found: C, 64.91; H, 3.91; N, 4.35.

Example 57

3-Acetyl-2-(2,5-difluorophenoxy)-5-(4-pyridyl)thiophene

3-Acetyl-5-chloro-2-(2,5-difluorophenoxy)thiophene

The subtitle compound was prepared according to the procedure of Example 42 using 2,5-difluorophenol instead of phenol.

¹H—NMR (CDCl₃) δ 7.27-6.90 (m, 4H), 2.50 (d, J=0.8 Hz, 3H).

3-Acetyl-2-(2,5-difluorophenoxy)-5-(4-pyridyl)thiophene

The title compound was prepared according to the procedure of Example 15 using 3-acetyl-5-chloro-2-(2,5-difluorophenoxy)thiophene instead of 3-acetyl-2,5-dichloro-4-methylthiophene.

mp: 119–121° C.

¹H—NMR (CDCl₃) δ 8.60-8.53 (m, 2H), 7.71 (s, 1H), 7.34-7.21 (m, 31H), 7.10-7.00 (m, 2H), 2.60 (s, 3H).

MS (ESI) m/z: 332 (M+H)⁺

Anal. Calcd. for $C_{17}H_{11}NO_2F_2S$ 0.1H₂O: C, 61.29 H, 3.39; N, 4.20. Found: C, 61.12; H, 3.63; N, 3.87.

Example 58

3-(4-Fluorophenyl)-1-(4-pyridyl)-5,6-dihydro-4H-cyclopenta(c)thiophene-4-one

1-Chloro-3-(4-fluorophenyl)-5,6-dihydro-4H-cyclopenta(c)thiophene-4-one

The subtitle compound was prepared according to the procedure of Example 53 using 4-fluorobenzeneboronic acid instead of 2-fluorobenzeneboronic acid in step 1.

¹H—NMR (CDCl₃) δ 7.98-7.90 (m, 2H), 7.13-7.06 (m, 2H), 3.07-2.86 (m, 4H).

3-(4-Fluorophenyl)-1-(4-pyridyl)-5,6-dihydro-4H-cyclopenta(c)thiophene-4-one

The title compound was prepared according to the procedure of Example 15 using 1-chloro-3-(4-fluorophenyl)-5,6-dihydro-4H-cyclopenta(c)thiophene-4-one instead of 3-acetyl-2,5-dichloro-4-methylthiophene.

mp: 193–195° C.

¹H—NMR (CDCl₃) δ 8.66 (dd, J=4.6, 1.6 Hz, 2H), 8.10-8.05 (m, 2H), 7.43 (dd, J=4.6, 1.6 Hz, 2H), 7.14 (t, J=8.6 Hz, 2H), 3.26-3.11 (m, 4H).

Anal. Calcd. for $C_{18}H_{12}FNOS$ 0.3H₂O: C, 68.69 H, 4.03; N, 4.45. Found: C, 68.34; H, 4.12; N, 4.09.

Example 59

2,5-Di(4-pyridyl)-3-thiophenecarboxamide

A mixture of 3-cyano-2,5-di(4-pyridyl)thiophene (40 mg, 0.152 mmol), potassium hydroxide (25 mg, 0.446 mmol) in 2-methyl-2-propanol (2 mL) was heated at reflux temperature for 2 hours. After cooling, the mixture was poured into water. The precipitates were collected by filtration, and dried under reduced pressure to give the title compound (30 mg, 70% yield).

mp: 240–242° C.

¹H—NMR (DMSO-d₆) δ 8.63 (d, J=5.1 Hz, 4H), 8.02 (s, 1H), 7.91 (s, 1H), 7.68 (dd, J=4.6, 1.6 Hz, 2H), 7.58 (s, 1H), 7.55 (dd, J=4.6, 1.6 Hz, 2H).

Anal. Calcd. for $C_{15}H_{11}N_3OS$ 0.75H₂O: C, 61.10 H, 4.27; N, 14.25. Found: C, 61.46; H, 4.45; N, 14.41.

Example 60

3-(Isopropyloxycarbonyl)-2,5-di(4-pyridyl)thiophene 3-(Isopropyloxycarbonyl)-2,5-dichlorothiophene The subtitle compound was prepared according to the procedure of Example 52 using 2-propanol instead of methylamine in step 1.

¹H—NMR (CDCl₃) δ 7.18 (s, 1H), 5.24-5.13 (m, 1H), 1.34 (d, J=6.3 Hz, 6H).

3-(Isopropyloxycarbonyl)-2,5-di(4-pyridyl)thiophene

The title compound was prepared according to the procedure of Example 15 using 3-(isopropyloxycarbonyl)-2,5-dichlorothiophene instead of 3-acetyl-2,5-dichloro-4-methylthiophene.

mp: 139–142° C.

MS (ESI) m/n: 325 (M+H)⁺

¹H—NMR (CDCl₃) δ 8.71-8.64 (m, 4H), 7.92 (s, 1H), 7.51-7.47 (m, 2H), 7.46-7.42 (m, 2H), 5.19-5.07 (m, 1H), 1.21 (d., J=6.3 Hz, 6H).

Anal. Calcd. for $C_{18}H_{16}N_2O_2S$ 0.2H₂O; C, 65.91; H, 5.04; N, 8.54. Found; C, 65.94; H, 5.23; N, 8.38.

Example 61

O-Methyl-20 -di(4-pyridyl)-4-methylthiophene-3-carbaldehyde oxime dihydrochloride A mixture of 2,5-di(4-pyridyl)-4-methylthiophene-3-carbaldehyde (0.15 g), methoxylamine hydrochloride (0.054 g), pyridine (0.2 mL), and MeOH (5 mL) was heated at reflux temperature for 8 hours. After cooling, volatiles were removed by evaporation. The residue was dissolved in $CH_2Cl_2$ (500 mL) and the whole washed with water, dried over $MgSO_4$, and concentrated in vacuo. The resulting residue was dissolved in 10% methanolic HCl and the solution was concentrated in vacuo again. The resulting solid was recrystallized with EtOH-diisopropyl ether to provide the title compound (0.091 g) as a mixture of E- and Z- form (3.5:1).

mp: 136–139° C.

$^1$H—NMR (DMSO-$d_6$) δ: 8.8–8.9 (m, 4H), 8.30 (s, 1H), 7.9–8.05 (m, 4H), 3.89 (s, 2.331H), 3.73 (s, 0.67H), 2.52 (s, 2.331H), 2.34 (s, 0.67H).

Anal. Calcd. for $C_{17}H_{15}N_3OS$ 2HCl 2.3$H_2O$: C, 48.19 H, 5.14; N, 9.92. Found: C, 48.38; H, 5.21; N, 9.95.

Example 62

3-Acetyl-2-(4-fluorophenoxy)-5-(4-pyridyl)thiophene

3-Acetyl-5-chloro-2-(4-fluorophenoxy)thiophene

The subtitle compound was prepared according to the procedure of Example 42 using 4-fluorophenol instead of phenol.

$^1$H—NMR (CDCl$_3$) δ 7.20-7.10 (m, 4H), 7.09 (s, 1H), 2.49 (s, 3H).

3-Acetyl-2-(2-fluorophenoxy)-5-(4-pyridyl)thiophene

The title compound was prepared according to the procedure of Example 15 using 3-acetyl-5-chloro-2-(4-fluorophenoxy)thiophene instead of 3-acetyl-2,5-dichloro-4-methylthiophene.

mp: 147–149° C.

$^1$H—NMR (CDCl$_3$) δ 8.55 (dd, J=4.6 and 1.6 Hz, 2H), 7.71 (s, 1H), 7.32-7.12 (m, 6H), 2.59 (s, 31H).

MS (ESI) m/z: 314 (M+H)$^+$

Anal. Calcd. for $C_{17}H_{12}NO_2FS$: C, 65.16 H, 3.86; N, 4.47. Found: C, 64.98; H, 4.10; N, 4.40.

Example 63

1-(4-Pyridyl)-3-(3-pyridyl)-5,6-dihydro-4H-cyclopenta(c)thiophene-4-one

1-Chloro-3-(3-pyridyl)-5,6-dihydro-4H-cyclopenta(c)thiophene-4-one

The subtitle compound was prepared according to the procedure of Example 53 using 3-pyridineboronic acid instead of 2-fluorobenzeneboronic acid in step 1.

$^1$H—NMR (CDCl$_3$) δ 8.99 (d, J=2.3 Hz. 1H), 8.59 (d. J=4.9 Hz. 1H), 8.41 (d, J=8.1 Hz, 1H), 7.35 (dd. J=8.1, 4.9 Hz, 1H), 3.08-2.88 (m. 4H).

1-(4-Pyridyl)-3-(3-pyridyl)-5,6-dihydro-4H-cyclopenta(c)thiophene-4-one

The title compound was prepared according to the procedure of Example 15 using 1-chloro-3-(3-pyridyl)-5,6-dihydro-4H-cyclopenta(c)thiophene-4-one instead of 3-acetyl-2,5-dichloro-4-methylthiophene.

mp: 214–216° C.

$^1$H—NMR (CDCl$_3$) δ 9.12 (d, J=2.0 Hz, 1H), 8.68 (dd, J=4.6, 1.6 Hz, 2H), 8.63 (dd, J=4.8, 1.3 Hz, 1H), 8.56-8.52 (m, 1H), 7.46 (dd, J=4.6, 1.6 Hz, 2H), 7.41 (dd, J=7.9, 4.8 Hz, 1H), 3.30-3.14 (m, 4H).

Anal. Calcd. for $C_{17}H_{12}N_2OS$ 0.1$H_2O$: C, 69.41 H, 4.18; N, 9.52. Found: C, 69.17; H, 4.46; N, 9.28.

Example 64

3-Difluoromethyl-2,5-di(4-pyridyl)-4-methylthiophene

To a stirred solution of diethylaminosulfer trifluoride (DAST, 0.7 g) in $CH_2Cl_2$ (5 mL) was added 2,5-di(4-pyridyl)-4-methylthiophene-3 -carbaldehyde (0.122 g) at 0° C. under nitrogen. The resulting mixture was stirred at room temperature for 3 hours. The reaction mixture was poured into ice water and the whole was extracted with $CH_2Cl_2$ (30 mL×1). The organic layer was washed with brine, dried over $MgSO_4$, and concentrated in vacuo. The residue was purified by flash chromatography eluting with ethyl acetate-$CH_2Cl_2$-MeOH (1:1:0.02) to give the solid, which was recrystallized from diisoplopanol-diisopropyl ether to provide the title compound (0.032 g).

mp: 132.5–132.7° C.

$^1$H—NMR (CDCl$_3$) δ 8.69–8.74 (m, 4H), 7.35–7.39 (m, 4H), 6.63 (t, J=54Hz, 1H), 2.49 (s. 3H).

Anal. Calcd. for $C_{16}H_{16}F_2N_2S$: C, 63.56, H, 4.00; N, 9.27. Found: C, 63.32; H, 4.39; N, 9.21.

Example 65

2,5-Di(4-pyridyl)-3-fluoromethyl-4-methylthiophene

3-Hydroxymethyl-2,5-di(4-pyridyl)-4-methylthiophene

To a stirred solution of 2,5-di(4-pyridyl)-4-methylthiophene-3-carbaldehyde (0.145 g) in methanol (10 mL) was added sodium borohydride (0.11 g) at 0° C. The mixture was stirred at room temperature for 30 minutes. Phosphate buffer was added to the reaction mixture and MeOH was removed by evaporation. The residue was extracted with ethyl acetate (30 mL×2). The combined organic layers were washed with brine, dried over $MgSO_4$, and concentrated in vacuo. The resulting residue was purified by flash chromatography eluting with ethyl acetate-$CH_2Cl_2$—MeOH (1:1:0.04) to give the subtitle compound (0.170 g).

$^1$H—NMR (CDCl$_3$) δ 8.66-8.70 (m, 4H), 7.49-7.51 (m, 2H), 7.38–7.40 (m, 2H), 4.67 (s, 2H), 2.45 (s, 3H).

2,5-Di(4-pyridyl)-3-fluoromethyl-4-methylthiophene

To a stirred solution of diethylaminosulfer trifluoride (DAST, 0.06 mL) in $CH_2Cl_2$ (5 mL) was added 3-hydroxymethyl-2,5-di(4-pyridyl)-4-methylthiophene (0.144 g) at 0° C. under nitrogen. The resulting mixture was stirred at room temperature for 1 hour. DAST (0.06 mL) was additionally added to the reaction mixture, and the mixture was stirred at room temperature for 1 hour. The reaction mixture was poured into ice-water and the whole was extracted with $CH_2Cl_2$ (50 mL). The organic layer was washed with brine, dried over $MgSO_4$, and concentrated in vacuo. The residue was purified by flash chromatography eluting with ethyl acetate-$CH_2Cl_2$ (1:1). The resulting solid was recrystallized from diisoplopanol-diisopropyl ether to give the title compound (0.056 g).

mp: 148–148.5° C.

$^1$H—NMR (CDCl$_3$) δ 8.68–8.73 (m, 4H), 7.43-7.45 (m, 2H), 7.38–7.41 (m, 2H), 5.33 (d, J=49 Hz, 2H), 2.44 (d, J=1Hz, 3H).

Anal. Calcd. for $C_{16}H_{13}N_2FS$: C, 67.58, H, 4.61; N. 9.85. Found: C, 67.47; H, 4.70; N, 9.63.

Example 66

1-(4-Pyridyl)-3-(4-trifluoromethylphenyl)-5,6-dihydro-4H-cyclopenta(c)thiophene-4-one 1-Chloro-3-(4-trifluoromethylphenyl)-5.6 -dihydro-4H-cyclopenta(c)thiophene-4-one The subtitle compound was prepared according to the procedure of Example 53 using 4-(trifluoromethyl)benzeneboronic acid instead of 2-fluorobenzeneboronic acid in step 1.

¹H—NMR (CDCl₃) δ 8.06 (d, J=8.1 Hz, 2H), 7.66 (d, J=8.1 Hz, 2H), 3.11-2.89 (m, 4H).

1-(4-Pyridyl)-3-(4-trifluoromethylphenyl)-5,6-dihydro-4H-cyclopenta(c)thiophene-4-one The title compound was prepared according to the procedure of Example 15 using 1-chloro-3-(4-trifluoromethylphenyl)-5,6-dihydro-4H-cyclopenta(c)thiophene-4-one instead of 3-acetyl-2,5-dichloro-4-methylthiophene.

mp: 158–160° C.

¹H—NMR (CDCl₃) δ 8.66 (d, J=4.6 Hz, 2H), 8.16 (d, J=8.1 Hz, 2H), 7.67 (d, J=8.1 Hz, 2H), 7.42 (d, J=4.6 Hz, 2H), 3.24-3.09 (m, 4H).

Anal. Calcd. for $C_{19}H_{12}F_3NOS$: C, 63.50 H. 3.37; N, 3.90. Found: C, 63.18; H, 3.64; N, 3.88.

Example 67

1-(4-Fluorophenyl)-3-(4-pyridyl)-5,6-dihydro-4H-cyclopenta(c)thiophene-4-one

To a stirred solution of 1-chloro-3-(4-pyridyl)-5,6-dihydro-4H-cyclopenta(c)thiophene-4-one (70 mg, 0.28 mmol) in DME (4 mL) was added4-fluorobenzeneboronic acid (100 mg, 0.71 mmol), saturated aqueous NaHCO₃ solution (2 mL) and bis(triphenylphosphine)palladium(II) chloride (200 mg, 0.28 mmol) at room temperature under nitrogen. The mixture was heated at reflux temperature for 8 hours. The whole was extracted with ethyl acetate (50 mL×2), and the combined organic layers were washed with brine, dried over MgSO₄, and concentrated in vacuo. The residue was purified by flash chromatography eluting with hexane-ethyl acetate (1:1) to provide the title product (20 mg, 23% yield).

mp: 155–157° C.

¹H—NMR (CDCl₃) δ 8.67 (d, J=6.1 Hz, 2H), 7.98 (d, J=6.1 Hz, 2H), 7.55 (dd, J=8.7, 5.1 Hz, 2H), 7.16 (t, J=8.4 Hz, 2H), 3.19-3.09 (m, 4H).

Anal. Calcd. for $C_{18}H_{12}FNOS$ 0.25hexane 0.5H₂O: C, 68.90 H, 4.89; N, 4.12. Found: C, 69.21; H, 4.79; N, 3.79.

Example 68

3-(N-Benzyl-N-methylamino)-1-(4-pyridyl)-5,6-dihydro-4H-cyclopenta(c)thiophene-4-one 3-(N-Benzyl-N-methylamino)-1-chloro-5,6-dihydro-4H-cyclopenta(c)thiophene-4-one A mixture of 1,3-dichloro-5,6-dihydro-4H-cyclopenta(c)thiophene-4-one (250 mg, 1.21 mmol) in N-benzylmethylamine (2 mL) was heated at 120° C. for 1 hour. After cooling, water (10 mL) was added to the mixture. The whole was extracted with CH₂Cl₂ (20 mL×2), and the combined organic layers were washed with brine, dried over MgSO₄, and concentrated in vacuo. The residue was purified by flash chromatography eluting with hexane-ethyl acetate (10:1) to provide the subtitle compound (259 mg, 74% yield).

¹H—NMR (CDCl₃) δ 7.36-7.21 (m, 5H), 5.05 (s, 2H), 3.04 (s, 3H), 2.93-2.69 (m, 4H).

3-(N-Benzyl-N-methylamino)-1-(4-pyridyl)-5,6-dihydro-4H-cyclopenta(c)thiophene-4-one The title compound was prepared according to the procedure of Example 15 using 3-(N-benzyl-N-methylamino)-1-chloro-5,6-dihydro-4H-cyclopenta(c)thiophene-4-one instead of 3-acetyl-2,5-dichloro-4-methylthiophene.

mp: 145–147° C.

¹H—NMR (CDCl₃) δ 8.48 (dd, J=4.6, 1.6 Hz, 2H), 7.37-7.22 (m, 5H), 7.19 (dd, J=4.6, 1.6 Hz, 2H), 5.20 (s, 2H), 3.16 (s, 3H), 3.11-2.95 (m, 4H).

Anal. Calcd. for $C_{20}H_{18}N_2OS$ 0.1H₂O: C, 71.44 H, 5.46; N, 8.33. Found: C, 71.33; H, 5.52; N. 8.17.

Example 69

[2,5-Di(4-pyridyl)-4-methylthiophen-3-yl]methylhydroxylamine trihydrochloride

N,O-Di-tert-butoxycarbonyl-[2,5-Di(4-pyridyl)-4-methylthiophen-3-yl]methylhydroxylamine To a stirred solution of 3-hydroxymethyl-2,5-di(4-pyridyl)-4-methylthiophene (0.282 g), triphenylphosphine (0.446 g), and N,O-di-(tert-butoxycarbonyl)hydroxylamine (0.224 g), in THF (20 mL) was added diethylazodicarboxylate (0.296 g) under nitrogen. After stirring for 23 hours, the reaction mixture was poured into water (50 mL) and the whole was extracted with CH₂Cl₂ (100 mL). The organic layer was washed with brine, dried over MgSO₄, and concentrated in vacuo. The residue was purified by flash chromatography eluting with ethyl acetate-CH₂Cl₂-MeOH (1:1:0.04). The resulting product was purified by column chromatography on silica(NH-silica gel, FUJI SILISIA CHEMICAL LTD. DM203 5)(ethyl acetate-CH₂Cl₂—MeOH=1:1:0.04) to give the subtitle compound (0.17 g)

¹H—NMR (acetone-d₆) δ 8.66–8.69 (m, 4H), 7.47–7.54 (m, 4H), 4.84 (br, 2H), 2.42 (s, 3H), 1.47 (s, 9H),1.33 (s, 9H).

2,5-Di(4-pyridyl)-4-methylthiophen-3-ylmethylhydroxylamine trihydrochloride

To a stirred solution of N,O-di-tert-butoxycarbonyl-[2,5-di(4-pyridyl)-4-methylthiophen-3-yl]methylhydroxylamine (0.16 g) in CH₂Cl₂ (15 mL) was added trifluoroacetic acid (0.5 mL) and the mixture watered for 2 hours at room temperature. Trifluoroacetic acid (3 mL) was additionally added to the reaction mixture, and stirred for 2 hours. Saturated aqueous NaHCO₃ solution was added to the reaction mixture and the whole was extracted with CH₂Cl₂ (100 mL×2). The combined organic layers were washed with brine, dried over MgSO₄, and concentrated in vacuo. The residue was purified by flash chromatography eluting with ethyl acetate-CH₂Cl₂ (1:1). The crude product was dissolved in 10% methanolic HCl (1 mL) and the volatiles were removed by evaporation. The resulting solid was recrystallized from diisopropyl ether to give the title compound (0.031 g).

mp:219–222° C. (decomp.)

¹H—NMR (DMSO-d₆) δ 8.88–8.92 (m, 4H), 8.00 (d, J=6.0 Hz, 2H), 7.95 (d, J=6.0 Hz, 2H), 4.47 (s, 2H), 2.55 (s, 3H).

Anal. Calcd. for $C_{16}H_{15}N_3OS$ 3HCl H₂O: C, 45.24, H, 4.75; N, 9.89. Found: C, 45.33; H, 4.80; N, 9.96.

Example 70

3-[2,5-di-(4-pyridyl)3-thienyl]propionamide 3-(2,5-di-chloro-3-thienyl)propionamide To a stirred solution of oxalyl chloride (1 mL) in CH₂Cl₂ (2 mL) was added 3-(2,5-dichloro-3-thienyl)propanoic acid (0.15 g) in CH₂Cl₂ (3 mL) under nitrogen. The resulting mixture was heated at reflux temperature for 1 hour. After cooling, volatiles were removed by evaporation to give the corresponding acid chloride, which was used for next reaction without further purification. To a stirred solution of 1,1,1,3,3,3-hexamethyldisilazane (0.4 mL) in CH₂Cl₂ (3 mL) was added the acid chloride in CH₂Cl₂ (5 ml) under nitrogen and the mixture was stirred for 2 hours. MeOH (2 mL) was added to the reaction mixture and the whole was stirred for 5 minutes. The resulting mixture was washed with 2N HCl solution, brine, dried over MgSO₄, and concentrated in vacuo. The residue was purified by flash chromatography eluting with ethyl acetate-methanol (100:1) to give the subtitle compound (0.115 g).

¹H—NMR (CDCl₃) δ: 6.70 (s, 1H), 5.36 (br, 2H), 2.88 (t, J=8 Hz, 2H), 2.46 (t, J=8 Hz, 2H).

3-[2,5-di-(4-pyridyl)3-thienyl]propionamide

The title compound was prepared according to the procedure of Example 15 using 3-(2,5-dichloro-3-thienyl) propionamide instead of 3-acetyl-2,5-dichloro-4-methylthiophene.

mp: 196–196.5° C.

1H—NMR (CDCl₃) δ 8.67–8.70(m, 2H), 8.60-8.63 (m, 2H), 7.40–7.48 (m, 5H), 5.34 (br, 2H), 3.13(t, J=8 Hz, 2H), 2.56 (t, J=8 Hz, 2H).

Anal. Calcd. for $C_{17}H_{15}N_3OS$: C, 66.00, H, 4.89; N, 13.58. Found: C, 65.78; H, 4.95; N, 13.54.

In addition, the chemical structures of the compounds prepared in the above Working Examples are summarized in the following Table.

TABLE (I')

| Ex.# | X | R¹ | R³ | R² |
|---|---|---|---|---|
| 1 | O | methyl | acetyl | methyl |
| 2 | O | —(CH₂)₃—C(O)— | | methyl |
| 3 | O | phenyl | acetyl | methyl |
| 4 | O | methyl | acetamino | methyl |
| 5 | O | methyl | methylaminocarbonyl | methyl |
| 6 | O | —(CH₂)₂—C(CH₃)₂—C(O)— | | methyl |
| 7 | O | —C(CH₃)₂—(CH₂)₂—C(O)— | | methyl |
| 8 | O | —(CH₂)₄—C(O)— | | methyl |
| 9 (hydrochloride) | O | isobutyl | acetyl | methyl |
| 10 | O | —CH₂—CH(CH₃)—O—C(O)— | | methyl |
| 11 | O | —C(CH₃)₂—(CH₂)₂—C(O)— | | ethyl |
| 12 | O | —C(CH₃)₂—(CH₂)₂—C(O)— | | phenyl |
| 13 | S | acetyl | 4-pyridyl | methyl |
| 14 | S | acetyl | methyl | 4-pyridyl |
| 15 | S | 4-pyridyl | acetyl | methyl |
| 16 | S | —(CH₂)₃—C(O)— | | H |
| 17 | S | chloro | methyl | acetyl |
| 18 | S | methyl | acetyl | methyl |
| 19 | S | phenyl | acetyl | methyl |
| 20 | S | —(CH₂)₃—C(O)— | | methyl |
| 21 | S | 4-pyridyl | CH₃—CH(OH)— | methyl |
| 22 | S | 4-pyridyl | —C(O)—(CH₂)₂— | |
| 23 | S | 4-pyridyl | CH₃O—C(O)— | H |
| 24 | S | 4-pyridyl | acetyl | H |
| 25 | S | 4-pyridyl | pyrrolidine-1-S(O₂)— | H |
| 26 (dihydrochloride) | S | 4-pyridyl | ethyl | methyl |
| 27 | S | H | acetyl | methyl |
| 28 (hydrochloride) | S | 4-methoxyphenyl | acetyl | methyl |
| 29 | S | 4-pyridyl | cyano | H |
| 30 (hydrochloride) | S | 4-chlorophenyl | acetyl | methyl |
| 31 (hydrochloride) | S | 4-trifluorophenyl | acetyl | methyl |
| 32 | S | 4-fluorophenyl | acetyl | methyl |
| 33 | S | 4-pyridyl | phenyl-C(O)— | H |
| 34 | S | 4-pyridyl | H(O)C— | methyl |
| 35 | S | 3-thienyl | acetyl | methyl |
| 36 | S | 4-CH₃S-phenyl | acetyl | methyl |
| 37 | S | 4-morpholino | acetyl | H |
| 38 | S | 4-methylpiperazinyl | acetyl | H |
| 39 (dihydrochloride) | S | 4-pyridyl | HO—N=C— | methyl |
| 40 (hydrochloride) | S | N-benzyl-N-methylamino | acetyl | H |
| 41 | S | 4-pyridyl | —(CH₂)₃—C(O)— | |
| 42 | S | phenoxy | acetyl | H |
| 43 | S | —S—C(acetyl)=C(CH₃)— | | methyl |
| 44 | S | 3-(4-fluorophenoxy)-phenoxy | acetyl | H |
| 45 | S | chloro | —(CH₂)₃—C(O)— | |
| 46 | S | CH₃—S(O)₂— | —C(O)—(CH₂)₃— | |

TABLE-continued (I')

| Ex.# | X | R¹ | R³ | R² |
|---|---|---|---|---|
| 47 | S | CH₃S— | —C(O)—(CH₂)₃— | |
| 48 | S | 4-pyridyl | CH₃—C(O)—(CH₂)₂— | H |
| 49 | S | 4-pyridyl | (CH₃)₂N—C(O)—(CH₂)₂— | H |
| 50 | S | 1-piperidino | acetyl | H |
| 51 (dihydrochloride) | S | 4-pyridyl | ethoxy-C(O)—(CH₂)₂— | H |
| 52 | S | 4-pyridyl | methylamino-C(O)— | H |
| 53 | S | 2-fluorophenyl | —C(O)—(CH₂)₂— | |
| 54 | S | chloro | —(CH₂)₂—C(O)— | |
| 55 | S | 4-pyridyl | CH₃—C(O)—O—N═C— | methyl |
| 56 | S | 2-fluorophenoxy | acetyl | H |
| 57 | S | 2,5-difluorophenoxy | acetyl | H |
| 58 | S | 4-fluorophenyl | —C(O)—(CH₂)₂— | |
| 59 | S | 4-pyridyl | H₂N—C(O)— | H |
| 60 | S | 4-pyridyl | isopropoxy-C(O)— | H |
| 61 (dihydrochloride) | S | 4-pyridyl | CH₃O—N═C— | methyl |
| 62 | S | 4-fluorophenoxy | acetyl | H |
| 63 | S | 3-pyridyl | —C(O)—(CH₂)₂— | |
| 64 | S | 4-pyridyl | difluoromethyl | methyl |
| 65 | S | 4-pyridyl | fluoromethyl | methyl |
| 66 | S | 4-CF3-phenyl | —C(O)—(CH₂)₂— | |
| 67 | S | 4-fluorophenyl | —C(O)—(CH₂)₂— | |
| 68 | S | N-benzyl-N-methylamino | —C(O)—(CH₂)₂— | |
| 69 (trihydrochloride) | S | 4-pyridyl | HO—NH—CH₂— | methyl |
| 70 | S | 4-pyridyl | H₂N—C(O)—(CH₂)₂— | H |

What is claimed is:

1. A compound of the formula:

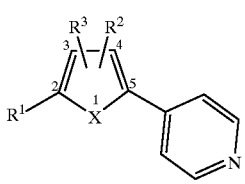

or a pharmaceutically effective salts thereof, wherein X is oxygen or sulfur, $R^1$ is 4-pyridyl optionally substituted with $C_{1-4}$ alkyl, $C_{1-4}$ alkylthio, $C_{1-4}$ alkoxy, hydroxy, trifluoromethyl, fluoro or chloro;

$R^2$ is hydrogen, chloro, fluoro, $C_{1-4}$ alkyl, phenyl, pyridyl or $C_{1-4}$ alkyl-C(O)—; and $R^3$ is $C_{1-4}$ alkyl-fluoro-$C_{1-4}$ alkyl, difluoro-$C_{1-4}$ alkyl, cyano, $C_{1-4}$ alkyl-O—C(O)-$C_{1-4}$ alkyl, $C_{1-4}$ alkyl-O—C(O)—, $H_2N$—C(O)—, $H_2N$—C(O)-$C_{1-4}$ alkyl, $C_{1-4}$ alkyl-NH—C(O)—, $C_{1-4}$ alkyl-C(O)—O—N═CH—, $C_{1-4}$ alkyl-O—N═CH—, HO—NH—$C_{1-4}$ alkyl, HO—N═C—, pyrrolyl—S(O)₂—, phenyl-C(O)—, formyl, $C_{1-4}$ alkyl-C(O)—, phenyl, pyridyl, $C_{1-4}$ alkyl-NH—C(O)— or $C_{1-4}$ alkyl-C(O)—NH-.

2. A compound according to claim 1, wherein:

$R^2$ is hydrogen, methyl, ethyl, acetyl, pyridyl or phenyl; and $R^3$ is methyl, ethyl, pyridyl, acetyl, propanoyl, acetamino, methylaminocarbonyl, 1-hydroxyethyl, methoxycarbonyl, pyrrolinine-1-sulfonyl, cyano, phenyl-C(O)—, formyl, HO—N═C—, $CH_3$—C(O)-$(CH_2)_2$—, $(CH_3)_2N$—C(O)-$(CH_2)_2$—, ethoxy-C(O)-$(CH_2)_2$—, methylamino-C(O)—, $CH_3$—C(O)—O—N═CH—, $H_2N$—C(O)—, isopropoxy-C(O)—, $CH_3O$—N═CH—, difluoromethyl, fluoromethyl, HO—NH—$CH_2$— or $H_2N$—C(O)-$(CH_2)_2$-.

3. A compound according to claim 2, wherein $R^2$ is hydrogen, methyl, ethyl or acetyl; and $R^3$ is methyl, ethyl, pyridyl, acetyl or propanoyl.

4. A compound according to claim 1, selected from the group consisting of:

2,5-di(4-pyridyl)-3-(1-hydroxyethyl)-4-methylthiophene;

2,5-di(4-pyridyl)-3-methoxycarbonylthiophene;

3-acetyl-2,5-di(4-pyridyl)thiophene;

2,5-di(4-pyridyl)-3-(pyrrolidine-1-sulfonyl)thiophene;

2,5-di(4-pyridyl)-3-ethyl-4-methylthiophene dihydrochloride;

3-cyano-2,5-di(4-pyridyl)thiophene;

3-benzoyl-2,5-di(4-pyridyl)thiophene;

2,5-di(4-pyridyl)-4-methylthiophene-3-carbaldehyde;

2,5-di(4-pyridyl)-4-methylthiophene-3-carbaldehyde oxime dihydrochloride;

ethyl 3-[2,5-di-(4-pyridyl)3-thienyl]propionate dihydrochloride;

N-methyl-{2,5-di(4-pyridyl)thiophen-3-yl}carboxamide;

O-acethyl-2,5-di(4-pyridyl)-4-methylthiophene-3-carbaldehyde oxime;

2,5-di(4-pyridyl)-3-thiophenecarboxamide;

3-(isopropyloxycarbonyl)-2,5-di(4-pyridyl)thiophene;

O-methyl-2,5-di(4-pyridyl)-4-methylthiophene-3-carbaldehyde oxime dihydrochloride;

3-difluoromethyl-2,5-di(4-pyridyl)-4-methylthiophene;

2,5-di(4-pyridyl)-3-fluoromethyl-4-methylthiophene;

2,5-di(4-pyridyl)-4-methylthiophen-3-yl]methylhydroxylamine trihydrochloride; and 3-[2,5-di-(4-pyridyl)3-thienyl]propionamide.

5. A compound according to claim 4, being one of the following:

3-acetyl-4-methyl-2,5-di(4-pyridyl)thiophene;

2,5-di(4-pyridyl)-3-methoxycarbonylthiophene;

3-acetyl-2,5-di(4-pyridyl)thiophene;

2,5-di(4-pyridyl)-3-ethyl-4-methylthiophene dihydrochloride;

3-benzoyl-2,5-di(4-pyridyl)thiophene;

2,5-di(4-pyridyl)-4-methylthiophene-3-carbaldehyde;

2,5-di(4-pyridyl)-4-methylthiophene-3-carbaldehyde oxime dihydrochloride;

(2,5-di-(4-pyridyl)3-thienyl)butan-3-one;

N,N-dimethyl-3-[2,5-di-(4-pyridyl)3-thienyl]propionamide;

O-acetyl-2,5-di(4-pyridyl)-4-methylthiophene-3-carbaldehyde oxime;

3-(isopropyloxycarbonyl)-2,5-di(4-pyridyl)thiophene;

O-methyl-2,5-di(4-pyridyl)-4-methylthiophene-3-carbaldehyde oxime dihydrochloride;

3-difluoromethyl-2,5-di(4-pyridyl)-4-methylthiophene;

2,5-di(4-pyridyl)-3-fluoromethyl-4-methylthiophene;

(2,5-di(4-pyridyl)-4-methylthiophen-3-yl)methylhydroxylamine trihydrochloride; and 3-[2,5-di-(4-pyridyl)3-thienyl]propionamide.

6. A pharmaceutical composition for the treatment of a cytokine-mediated or CAM-mediated disorder or condition in a mammal, which comprises an amount of the compound of claim 1, or a pharmaceutically effective sale thereof, that is effective in treating such disorder or condition, and a pharmaceutically acceptable carrier.

7. A method for treating a disorder or condition, the treatment of which can be effected or facilitated by reducing or inhibiting a cytokine mediator or CAM mediator of said disorder or condition in a mammal, comprising administering to a mammal in need of such treatment an amount of a compound of claim 1, or a pharmaceutically effective salt thereof, that is effective in treating such disorder or condition.

8. The compound 3-acetyl-4-methyl-2,5-di(4-pyridyl)thiophene.

* * * * *